(12) United States Patent
Carballido Herrera et al.

(10) Patent No.: US 8,999,708 B2
(45) Date of Patent: Apr. 7, 2015

(54) ANTI-IL12Rβ1 ANTIBODIES AND THEIR USE IN TREATING AUTOIMMUNE AND INFLAMMATORY DISORDERS

(71) Applicants: Jose M. Carballido Herrera, Allschwil (CH); Stefan Hartle, Jesenwang (DE); Christoph Heusser, Oberwil (CH); Ingo Klagge, Neuried (DE); Andrea Polzer, Munich (DE); Christoph Schwaerzler, St. Louis (FR); Gabriela Wochnik-Veltrup, Eching a.A. (DE)

(72) Inventors: Jose M. Carballido Herrera, Allschwil (CH); Stefan Hartle, Jesenwang (DE); Christoph Heusser, Oberwil (CH); Ingo Klagge, Neuried (DE); Andrea Polzer, Munich (DE); Christoph Schwaerzler, St. Louis (FR); Gabriela Wochnik-Veltrup, Eching a.A. (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/045,383

(22) Filed: Oct. 3, 2013

(65) Prior Publication Data
US 2014/0099708 A1  Apr. 10, 2014

Related U.S. Application Data

(62) Division of application No. 13/252,721, filed on Oct. 4, 2011, now Pat. No. 8,574,573.

(60) Provisional application No. 61/389,916, filed on Oct. 5, 2010.

(51) Int. Cl.
| | |
|---|---|
| C07K 16/28 | (2006.01) |
| C07H 21/04 | (2006.01) |
| C12N 5/10 | (2006.01) |
| C12N 15/13 | (2006.01) |
| C12N 9/02 | (2006.01) |
| C12Q 1/66 | (2006.01) |

(52) U.S. Cl.
CPC .......... *C12N 9/0069* (2013.01); *C07K 16/2866* (2013.01); *C12Q 1/66* (2013.01); *C07K 2317/33* (2013.01); *C07K 2317/34* (2013.01); *C07K 2317/55* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,853,721 A | 12/1998 | Gately et al. |
| 6,046,012 A | 4/2000 | Chizzonite et al. |
| 2002/0025317 A1 | 2/2002 | Leung et al. |

FOREIGN PATENT DOCUMENTS

| | | |
|---|---|---|
| WO | 2010/027767 A1 | 3/2010 |
| WO | 2010/112458 A1 | 10/2010 |

OTHER PUBLICATIONS

Presky et al., "Analysis of the multiple interactions between IL-12 and the high affinity IL-12 receptor complex," Journal of Immunology 160(5):2174-2179 (Mar. 1, 1998).
Wark et al., "Latest technologies for the enhancement of antibody affinity," Advanced Drug Delivery Reviews 58 (5-6):657-670 (Aug. 7, 2006).
Hoogenboom H.R., "Designing and optimizing library selection strategies for generating high-affinity antibodies," Trends in Biotechnology 15(2):62-70 (Feb. 1, 1997).
Steidl et al., "In vitro affinity maturation of recombinant antibodies by combination of pre-selected CDR-library pools," IP.COM Journal, IP.COM Inc., Oct. 16, 2007.
Hanes et al., "Picomolar Affinity Antibodies from a Fully Synthetic Naive Library Selected and Evolved by Ribosome Display," Nature Biotechnology 18(12):1287-1292 (Dec. 1, 2000).
Presta, L.G., "Engineering Antibodies for Therapy," Current Pharmaceutical Biotechnology 3(3):237-256 (Jan. 1, 2002).
Hezareh et al., "Effector function activities of a panel of mutants of a broadly neutralizing antibody against human immunodeficiency virus type 1," Journal of Virology 75(24):12161-12168 (Dec. 1, 2001).
Chapman, Andrew, "PEGylated antibodies and antibody fragments for improved therapy: A review," Advanced Drug Delivery Reviews 54(4):531-545 (Jun. 17, 2002).
Altare et al., "Interleukin-12 receptor beta1 deficiency in a patient with abdominal tuberculosis," Journal of Infectious Diseases 184(2):231-236 (Jul. 15, 2001).
Fieschi et al., "A novel form of complete IL-12/IL-23 receptor beta1 deficiency with cell surface-expressed nonfunctional receptors," Blood 104(7):2095-2101 (Oct. 1, 2004).
Lilic et al., "Deregulated production of protective cytokines in response to *Candida albicans* infection in patients with chronic mucocutaneous candidiasis," Infection and Immunity 71(10):5690-5699 (Oct. 2003).
Barrie et al., "The interleukin-12 family of cytokines: Therapeutic targets for inflammatory disease mediation," Clinical and Applied Immunology Reviews 5:225-240 (2005).
Anderson et al., "Interluekin-12 to interleukin 'infinity': the rationale for future therapeutic cytokine targeting," Springer Semin Immun 27:425-442 (2006).
Ding et al., "ABT-874, a fully human monoclonal anti-IL-12/IL-23 antibody for the potential treatment of autoimmune diseases," Current Opinion in Investigational Drugs 9(5):515-522 (2008).

(Continued)

*Primary Examiner* — Marianne P Allen

(57) ABSTRACT

The present invention relates to antibodies that specifically bind to IL12Rβ1, the non-signal transducing chain of both the heterodimeric IL12 and IL23 receptors. The invention more specifically relates to specific antibodies that are IL12 and IL23 receptor antagonists capable of inhibiting IL12/IL18 induced IFNγ production of blood cells and compositions and methods of use for said antibodies to treat pathological disorders that can be treated by inhibiting IFNγ production, IL12 and/IL23 signaling, such as rheumatoid arthritis, psoriasis or inflammatory bowel diseases or other autoimmune and inflammatory disorders.

16 Claims, No Drawings

(56) References Cited

OTHER PUBLICATIONS

Vandenbroeck et al., "Inhibiting cytokines of the interleukin-12 family: recent advances and novel challenges," Journal of Pharmacy and Pharmacology 56:145-160 (2004).

Reddy et al., "Modulation of CLA, IL-12R, CD40L, and IL-2Ralpha expression and inhibition of IL-12-and IL-23- induced cytokine secretion by CNTO 1275," Cellular Immunology 247:1-11 (2007).

Abhinandan, et al. "Analysis and improvements to Kabat and Structurally Correct Numbering of Antibody Variable Domains", Molecular Immunology 45:3832-3839 (2008).

ANTI-IL12Rβ1 ANTIBODIES AND THEIR USE IN TREATING AUTOIMMUNE AND INFLAMMATORY DISORDERS

RELATED APPLICATIONS

This application is a Divisional of U.S. application Ser. No. 13/252,721 filed Oct. 4, 2011, which claims priority to U.S. Provisional Application No. 61/389,916 filed Oct. 5, 2010, the contents of each of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Nov. 17, 2011 is named 54362.txt and is 139,264 bytes in size.

BACKGROUND OF THE INVENTION

The present invention relates to antibodies that specifically bind to IL12Rβ1, the non-signal transducing chain of both the heterodimeric IL12 and IL23 receptors.

The invention more specifically relates to specific antibodies that are IL12 and IL23 receptor antagonists capable of inhibiting IL12/IL18 induced IFNγ production of blood cells and compositions and methods of use for said antibodies to treat pathological disorders that can be treated by inhibiting IFNγ production, IL12 and/IL23 signaling, such as rheumatoid arthritis, psoriasis or inflammatory bowel diseases or other autoimmune and inflammatory disorders.

The IL12 receptor beta 1 (IL12Rβ1) chain is known as a potential therapeutic target for the treatment of Th1/Th17 mediated disorders, such as psoriasis and other autoimmune and inflammatory disorders. Psoriasis is a common chronic inflammatory skin disease characterized by hyper-proliferation of the epidermal layer and a prominent infiltrate of dendritic cells and T cells. T cells play a key role in the pathological reactions occurring in the skin by secreting type 1 cytokines (including IFN-γ and TNF-α) and that induce keratinocyte hyperproliferation, angiogenesis and neutrophil infiltration.

Two cytokines that are thought to be important in the development of Th1 immune responses in psoriasis are interleukin-12 (IL12) and interleukin-23 (IL23). Both cytokines are produced by antigen-presenting cells, such as macrophages and dendritic cells, and function by activating T cells and natural killer cells. IL12 and IL23 are members of a heterodimeric family of soluble cytokines that are comprised of p35/p40 protein subunits in IL12 and p19/p40 protein subunits in IL23. The p40 subunit of either cytokine binds to the transmembrane IL12 receptor β1 (IL12Rβ1) that is found on the surface of immune cells. Interruption of the IL12 p40/IL12Rβ1 interaction may prevent the biological activity of both IL12 and IL23 (Presky et al., J. Immunol. 160 (1998): 2174-79, Parham et al., J. Immunol. 168 (2002): 5699-5708.).

Several inflammatory and autoimmune diseases including psoriasis are linked to exacerbated Th1 and/or Th17 responses. Many of them are currently treated either with general immuno-suppressants or very selectively acting biologicals such as anti-TNF-α antibodies that are not effective in all patients. These were found to increase the risk for infections and to become ineffective after repeated treatment. Therefore, there is an unmet medical need for treatments with increased safety profiles and simultaneous capacity to induce long-term remission or cure of the disease.

A neutralizing antibody to IL12p40 successfully abolished psoriatic lesions in mice, even when administered after transfer of the T cell subset that induced the psoriasis-like condition (Hong et al., J. Immunol. 162.12 (1999): 7480-91.). An anti-IL12p40 antibody targeting both IL12 and IL23 is currently in clinical trials for Psoriasis (Kauffman et al. J. Invest Dermatol. 123.6 (2004): 1037-44, Papp et al. Lancet. 371.9625 (2008): 1675-84, Kimball et al. Arch. Dermatol. 144.2 (2008): 200-07), Crohn's Disease (Sandborn et al., Gastroenterology. 135.4 (2008): 1130-41) and Multiple Sclerosis (Segal et al., Lancet Neurol. 7.9 (2008): 796-804). Targeting IL12Rβ1 and hence, differentiation and maintenance of Th1 and Th17 cell populations as well as the IL12 and IL23 mediated inflammatory cytokine production by these cells, offers an opportunity for an improved therapeutic agent.

U.S. Pat. No. 6,046,012 refers to IL12Rβ1 and antibodies binding to anti-IL12Rβ1 in general. Anti-mouse IL12Rβ1 monoclonal antibodies are also commercialized by Becton Dickinson (Cat#551455).

However, to date, there is no description in the art of binding molecules to human IL12Rβ1 showing highly potent IL12Rβ1 antagonistic activity, for use in the treatment of autoimmune and inflammatory disorders, such as psoriasis, rheumatoid arthritis or Crohn's disease. Only indirect evidence by targeting the respective interaction partner (IL12p40) validates the pathway.

Therefore, in one aspect, the invention provides an antibody, or a protein comprising an antigen-binding portion of said antibody, that binds both to the IL12 receptor and the IL23 receptor, characterized in that the antibody or protein specifically binds to IL12Rβ1 polypeptide of SEQ ID NO:89.

In one specific embodiment, the isolated antibody or protein of the invention, comprises either (a) a variable heavy chain amino acid sequence comprising HCDR1 of SEQ ID NO:1, HCDR2 of SEQ ID NO:2, HCDR3 of SEQ ID NO:3 and a variable light chain amino acid sequence comprising LCDR1 of SEQ ID NO:4, LCDR2 of SEQ ID NO:5 and LCDR3 of SEQ ID NO:6;

(b) a variable heavy chain amino acid sequence comprising HCDR1 of SEQ ID NO:7, HCDR2 of SEQ ID NO:8, HCDR3 of SEQ ID NO:9 and a variable light chain amino acid sequence comprising LCDR1 of SEQ ID NO:10, LCDR2 of SEQ ID NO:11 and LCDR3 of SEQ ID NO:12;

(c) a variable heavy chain amino acid sequence comprising HCDR1 of SEQ ID NO:13, HCDR2 of SEQ ID NO:14, HCDR3 of SEQ ID NO:15 and a variable light chain amino acid sequence comprising LCDR1 of SEQ ID NO:16, LCDR2 of SEQ ID NO:17 and LCDR3 of SEQ ID NO:18;

(d) a variable heavy chain amino acid sequence comprising HCDR1 of SEQ ID NO:19, HCDR2 of SEQ ID NO:20, HCDR3 of SEQ ID NO:21 and a variable light chain amino acid sequence comprising LCDR1 of SEQ ID NO:22, LCDR2 of SEQ ID NO:23 and LCDR3 of SEQ ID NO:24;

(e) a variable heavy chain amino acid sequence comprising HCDR1' of SEQ ID NO:25, HCDR2' of SEQ ID NO:26, HCDR3' of SEQ ID NO:27 and a variable light chain amino acid sequence comprising LCDR1' of SEQ ID NO:28, LCDR2' of SEQ ID NO:29 and LCDR3' of SEQ ID NO:30;

(f) a variable heavy chain amino acid sequence comprising HCDR1' of SEQ ID NO:31, HCDR2' of SEQ ID NO:32, HCDR3' of SEQ ID NO:33 and a variable light chain amino acid sequence comprising LCDR1' of SEQ ID NO:34, LCDR2' of SEQ ID NO:35 and LCDR3' of SEQ ID NO:36;

(g) a variable heavy chain amino acid sequence comprising HCDR1' of SEQ ID NO:37, HCDR2' of SEQ ID NO:38, HCDR3' of SEQ ID NO:39 and a variable light chain amino acid sequence comprising LCDR1' of SEQ ID NO:40, LCDR2' of SEQ ID NO:41 and LCDR3' of SEQ ID NO:42;

(h) a variable heavy chain amino acid sequence comprising HCDR1' of SEQ ID NO:43, HCDR2' of SEQ ID NO:44, HCDR3' of SEQ ID NO:45 and a variable light chain amino acid sequence comprising LCDR1' of SEQ ID NO:46, LCDR2' of SEQ ID NO:47 and LCDR3' of SEQ ID NO:48; or, (i) a variable heavy chain ($V_H$) and a variable light chain ($V_L$) amino acid sequence where each of the CDRs share at least 60, 70, 80, 90, 95 or 100 percent sequence identity with the corresponding CDR sequence of at least one antibody or protein described in (a)-(h) above, and said antibody or protein binds to the IL12Rβ1 polypeptide of SEQ ID NO:89 with a $K_D$ of 1 nM or less, 100 pM or less, or 10 pM or less and inhibits IL12 and/or IL23 binding to IL12Rβ1 polypeptide as measured in an in vitro competitive binding assay.

In another aspect the invention provides an isolated antibody or protein with an antigen-binding portion of an antibody which (i) binds to an epitope of the human IL12Rbeta1 polypeptide of SEQ ID NO:89, wherein the epitope: a) is comprised within amino acid residues 416 to 429 of the human IL12Rbeta1 polypeptide of SEQ ID NO:89; or b) comprises at least one, two, three, four, five, six, seven, eight, or nine or more of the amino acid residues as defined in a) listed above; or c) comprises the amino acid residues as defined in a) listed above.

In one embodiment there is provided an isolated antibody or protein with an antigen-binding portion of an antibody which (i) binds to an epitope of the human IL12Rbeta1 polypeptide of SEQ ID NO:89, wherein the epitope: a) is comprised within amino acid residues 416 to 429 of the human IL12Rbeta1 polypeptide of SEQ ID NO:89; or b) comprises at least one, two, three, four, five, six, seven, eight, or nine or more of the amino acid residues as defined in a) listed above; or c) comprises the amino acid residues as defined in a) listed above, and/or (ii) competes with an antibody which binds the epitope defined in (i) above.

In another embodiment there is provided an isolated antibody or protein with an antigen-binding portion of an antibody which (i) binds to an epitope of the human IL12Rbeta1 polypeptide of SEQ ID NO:89 as measured using amide Hydrogen/Deuterium exchange Mass Spectrometry, wherein the epitope: a) is comprised within amino acid residues 416 to 429 of the human IL12Rbeta1 polypeptide of SEQ ID NO:89; or b) comprises at least one, two, three, four, five, six, seven, eight, or nine or more of the amino acid residues as defined in a) listed above; or c) comprises the amino acid residues as defined in a) listed above, and/or (ii) competes with an antibody which binds the epitope defined in (i) above.

In another embodiment there is provided an isolated antibody or protein with an antigen-binding portion of an antibody which (i) binds to an epitope of the human IL12Rbeta1 polypeptide of SEQ ID NO:89, wherein the epitope: a) is comprised within amino acid residues 416 to 429 of the human IL12Rbeta1 polypeptide; or b) comprises at least one, two, three, four, five, six, seven, eight, or nine or more of the amino acid residues as defined in a) listed above; or c) comprises the amino acid residues as defined in a) listed above, and/or (ii) competes with an antibody which binds the epitope defined in (i) above, wherein said antibody or protein binds to the IL12Rbeta1 polypeptide of SEQ ID NO:89 with a KD of 1 nM or less and inhibits IL12 and/or IL23 binding to the IL12Rbeta1 polypeptide of SEQ ID NO:89 as measured in an in vitro competitive binding assay.

In another embodiment there is provided an isolated antibody or protein with an antigen-binding portion of an antibody which (i) binds to an epitope of the human IL12Rbeta1 polypeptide of SEQ ID NO:89 as measured using amide Hydrogen/Deuterium exchange Mass Spectrometry, wherein the epitope: a) is comprised within amino acid residues 416 to 429 of the human IL12Rbeta1 polypeptide; or b) comprises at least one, two, three, four, five, six, seven, eight, or nine or more of the amino acid residues as defined in a) listed above; or c) comprises the amino acid residues as defined in a) listed above, and/or (ii) competes with an antibody which binds the epitope defined in (i) above, wherein said antibody or protein binds to the IL12Rbeta1 polypeptide of SEQ ID NO:89 with a KD of 1 nM or less and inhibits IL12 and/or IL23 binding to the IL12Rbeta1 polypeptide of SEQ ID NO:89 as measured in an in vitro competitive binding assay.

In another embodiment there is provided an isolated antibody or a protein with an antigen-binding portion of an antibody, wherein said antibody or protein binds to an epitope within residues 416 to 429 of the human IL12Rbeta1 polypeptide of SEQ ID NO:89 and/or competes with an antibody or a protein with an antigen-binding portion of an antibody that binds to an epitope within residues 416 to 429 of the human IL12Rbeta1 polypeptide of SEQ ID NO:89.

In another embodiment there is provided an isolated antibody or a protein with an antigen-binding portion of an antibody, wherein said antibody or protein binds to an epitope within residues 416 to 429 of the human IL12Rbeta1 polypeptide of SEQ ID NO:89 as measured using amide Hydrogen/Deuterium exchange Mass Spectrometry, and/or competes with an antibody or a protein with an antigen-binding portion of an antibody that binds to an epitope within residues 416 to 429 of the human IL12Rbeta1 polypeptide of SEQ ID NO:89.

In another embodiment there is provided an isolated antibody or a protein with an antigen-binding portion of an antibody, wherein said antibody or protein binds to an epitope within residues 416 to 429 of the human IL12Rbeta1 polypeptide of SEQ ID NO:89 and/or competes with an antibody or a protein with an antigen-binding portion of an antibody that binds to an epitope within residues 416 to 429 of the human IL12Rbeta1 polypeptide of SEQ ID NO:89, wherein said antibody or protein binds to the IL12Rbeta1 polypeptide of SEQ ID NO:89 with a KD of 1 nM or less and inhibits IL12 and/or IL23 binding to the IL12Rbeta1 polypeptide of SEQ ID NO:89 as measured in an in vitro competitive binding assay.

In another embodiment there is provided an isolated antibody or a protein with an antigen-binding portion of an antibody, wherein said antibody or protein binds to an epitope within residues 416 to 429 of the human IL12Rbeta1 polypeptide of SEQ ID NO:89 as measured using amide Hydrogen/Deuterium exchange Mass Spectrometry and/or competes with an antibody or a protein with an antigen-binding portion of an antibody that binds to an epitope within residues 416 to 429 of the human IL12Rbeta1 polypeptide of SEQ ID NO:89, wherein said antibody or protein binds to the IL12Rbeta1 polypeptide of SEQ ID NO:89 with a KD of 1 nM or less and inhibits IL12 and/or IL23 binding to the IL12Rbeta1 polypeptide of SEQ ID NO:89 as measured in an in vitro competitive binding assay.

In another embodiment there is provided an isolated antibody or a protein with an antigen-binding portion of an antibody, wherein said antibody or protein binds to an epitope within residues 416 to 429 of the IL12Rbeta1 polypeptide of SEQ ID NO:89 and/or competes with an antibody which binds within residues 416 to 429 of the IL12Rbeta1 polypeptide of SEQ ID NO:89.

In another embodiment there is provided an isolated antibody or a protein with an antigen-binding portion of an antibody, wherein said antibody or protein binds within residues 416 to 429 of the IL12Rbeta1 polypeptide of SEQ ID NO:89 as measured using amide Hydrogen/Deuterium exchange Mass Spectrometry and/or competes with an antibody which binds within residues 416 to 429 of the IL12Rbeta1 polypeptide of SEQ ID NO:89.

In another embodiment there is provided an isolated antibody or a protein with an antigen-binding portion of an antibody, wherein said antibody or protein binds to an epitope within residues 416 to 429 of the IL12Rbeta1 polypeptide of SEQ ID NO:89 and/or competes with an antibody which binds within residues 416 to 429 of the IL12Rbeta1 polypeptide of SEQ ID NO:89, wherein said antibody or protein binds to the IL12Rbeta1 polypeptide of SEQ ID NO:89 with a KD of 1 nM or less and inhibits IL12 and/or IL23 binding to the IL12Rbeta1 polypeptide of SEQ ID NO:89 as measured in an in vitro competitive binding assay.

In another embodiment there is provided an isolated antibody or a protein with an antigen-binding portion of an antibody which binds to at least one amino acid residue within residues 416 to 429 of the IL12Rbeta1 polypeptide of SEQ ID NO:89 and/or competes with an antibody which binds to at least one amino acid residue within residues 416 to 429 of the IL12Rbeta1 polypeptide of SEQ ID NO:89.

In another embodiment there is provided an isolated antibody or a protein with an antigen-binding portion of an antibody which binds to at least one amino acid residue within residues 416 to 429 of the IL12Rbeta1 polypeptide of SEQ ID NO:89 as measured using amide Hydrogen/Deuterium exchange Mass Spectrometry and/or competes with an antibody which binds to at least one amino acid residue within residues 416 to 429 of the IL12Rbeta1 polypeptide of SEQ ID NO:89.

In the embodiments described herein, epitope binding may be determined using amide Hydrogen/Deuterium exchange Mass Spectrometry or other conventional epitope mapping techniques known in the art.

In the embodiments described herein, antibody competition can be measured using a Biacore or Elisa-based cross-blocking assay, as described herein, or using other cross-blocking assays known in the art.

In preferred embodiments the antibody or protein with an antigen-binding portion of an antibody binds to human IL12Rbeta1 at an epitope as defined in above.

Antibodies or proteins with an antigen-binding portion of an antibody falling within the scope of the invention can be identified by (i) screening for specificity for the human IL12Rbeta1 polypeptide of SEQ ID NO:89; (ii) optionally determining the affinity of the antibody; (iii) optionally assessing inhibition of IL12 and/or IL23 binding to the IL12Rbeta1 polypeptide of SEQ ID NO:89 as measured in an in vitro competitive binding assay; and (iv) optionally assessing binding to or within the epitope defined by amino acid residues 416 to 429 of the human IL12Rbeta1 polypeptide of SEQ ID NO:89 using amide Hydrogen/Deuterium exchange Mass Spectrometry or other conventional epitope mapping techniques known in the art, and/or assessing competition with an antibody which binds the epitope as defined above using a Biacore or Elisa-based cross-blocking assay, as described herein, or using other cross-blocking assays known in the art. After screening step (i) antibodies or proteins falling within the scope of the invention may be identified by performing one, or two, or three or four of the following steps: (a) determining the affinity of the antibody; (b) assessing inhibition of IL12 and/or IL23 binding to the IL12Rbeta1 polypeptide of SEQ ID NO:89 as measured in an in vitro competitive binding assay; (c) assessing binding to or within the epitope defined by amino acid residues 416 to 429 of the human IL12Rbeta1 polypeptide of SEQ ID NO:89 using amide Hydrogen/Deuterium exchange Mass Spectrometry or other conventional epitope mapping techniques known in the art, and (d) assessing competition with an antibody which binds the epitope as defined above using a Biacore or Elisa-based cross-blocking assay, as described herein, or using other cross-blocking assays known in the art.

Antibodies or proteins with an antigen-binding portion of an antibody falling within the scope of the invention can be identified by (i) screening for specificity for the human IL12Rbeta1 polypeptide of SEQ ID NO:89; (ii) determining the affinity of the antibody; (iii) assessing inhibition of IL12 and/or IL23 binding to the IL12Rbeta1 polypeptide of SEQ ID NO:89 as measured in an in vitro competitive binding assay; and (iv) optionally assessing binding to or within the epitope defined by amino acid residues 416 to 429 of the human IL12Rbeta1 polypeptide of SEQ ID NO:89 using amide Hydrogen/Deuterium exchange Mass Spectrometry or other conventional epitope mapping techniques known in the art, and/or assessing competition with an antibody which binds the epitope as defined above using a Biacore or Elisa-based cross-blocking assay, as described herein, or using other cross-blocking assays known in the art.

Antibodies or proteins with an antigen-binding portion of an antibody falling within the scope of the invention can be identified by (i) screening for specificity for the human IL12Rbeta1 polypeptide of SEQ ID NO:89; (ii) determining the affinity of the antibody; (iii) assessing inhibition of IL12 and/or IL23 binding to the IL12Rbeta1 polypeptide of SEQ ID NO:89 as measured in an in vitro competitive binding assay; and (iv) assessing binding to or within the epitope defined by amino acid residues 416 to 429 of the human IL12Rbeta1 polypeptide of SEQ ID NO:89 using amide Hydrogen/Deuterium exchange Mass Spectrometry or other conventional epitope mapping techniques known in the art, and/or assessing competition with an antibody which binds the epitope as defined above using a Biacore or Elisa-based cross-blocking assay, as described herein, or using other cross-blocking assays known in the art.

Antibodies or proteins with an antigen-binding portion of an antibody falling within the scope of the invention can be identified by (i) screening for specificity for the human IL12Rbeta1 polypeptide of SEQ ID NO:89; and (ii) assessing binding to or within the epitope defined by amino acid residues 416 to 429 of the human IL12Rbeta1 polypeptide of SEQ ID NO:89 using amide Hydrogen/Deuterium exchange Mass Spectrometry or other conventional epitope mapping techniques known in the art, and/or assessing competition with an antibody which binds the epitope as defined above using a Biacore or Elisa-based cross-blocking assay, as described herein, or using other cross-blocking assays known in the art.

In one specific embodiment, the isolated antibody or protein inhibits IL12 dependent IFN-γ production in human blood cells with an $IC_{50}$ around 1 nM, 100 pM or 10 pM or less.

The isolated antibody or protein according to the invention may be a fully human or humanized antibody. In one embodiment, it comprises a mutant or chemically modified amino acid Fc region, wherein said mutant or chemical modification confers no or decreased ADCC activity to said antibody when compared to a corresponding antibody with wild type Fc region. In a specific embodiment, it is a mutant silent IgG1 antibody.

In another embodiment, the antibody or protein of the invention essentially consists of a pegylated antigen-binding portion of an antibody which specifically binds to IL12Rβ1 polypeptide (SEQ ID NO:89).

In another embodiment, the antibody or protein of the invention comprises a variable heavy chain region of an antibody ($V_H$) with a polypeptide sequence having at least 95 or 100 percent sequence identity to at least one of SEQ ID NO:49, SEQ ID NO:51, SEQ ID NO:53 and SEQ ID NO:55.

In another embodiment, the antibody or protein of the invention comprises a variable light chain region of an antibody ($V_L$) with a polypeptide sequence having at least 95 or 100 percent sequence identity to at least one of SEQ ID NO:50, SEQ ID NO:52, SEQ ID NO:54 and SEQ ID NO:56.

In a specific embodiment, an antibody according to the invention is selected from the group consisting of:
(a) mAb1 consisting of a heavy chain amino acid sequence of SEQ ID NO:57 and a light chain amino acid sequence of SEQ ID NO:69;
(b) mAb2 consisting of heavy chain amino acid sequence of SEQ ID NO:61 and light chain amino acid sequence of SEQ ID NO:69;
(c) mAb3 consisting of heavy chain amino acid sequence of SEQ ID NO:65 and light chain amino acid sequence of SEQ ID NO:69;
(d) mAb4 consisting of heavy chain amino acid sequence of SEQ ID NO:58 and light chain amino acid sequence of SEQ ID NO:70;
(e) mAb5 consisting of heavy chain amino acid sequence of SEQ ID NO:62 and light chain amino acid sequence of SEQ ID NO:70;
(f) mAb6 consisting of heavy chain amino acid sequence of SEQ ID NO:66 and light chain amino acid sequence of SEQ ID NO:70;
(g) mAb7 consisting of heavy chain amino acid sequence of SEQ ID NO:59 and light chain amino acid sequence of SEQ ID NO:71;
(h) mAb8 consisting of heavy chain amino acid sequence of SEQ ID NO:63 and light amino acid chain sequence of SEQ ID NO:71;
(i) mAb9 consisting of heavy chain amino acid sequence of SEQ ID NO:67 and light chain amino acid sequence of SEQ ID NO:71;
(j) mAb10 consisting of heavy chain sequence of SEQ ID NO:60 and light chain sequence of SEQ ID NO:72;
(k) mAb11 consisting of heavy chain sequence of SEQ ID NO:64 and light chain sequence of SEQ ID NO:72; or,
(l) mAb12 consisting of heavy chain sequence of SEQ ID NO:68 and light chain sequence of SEQ ID NO:72;
(m) mAb13 consisting of heavy chain sequence of SEQ ID NO:90 and light chain sequence of SEQ ID NO:69;
(n) mAb14 consisting of heavy chain sequence of SEQ ID NO:91 and light chain sequence of SEQ ID NO:70;
(o) mAb15 consisting of heavy chain sequence of SEQ ID NO:92 and light chain sequence of SEQ ID NO:71; and,
(p) mAb16 consisting of heavy chain sequence of SEQ ID NO:93 and light chain sequence of SEQ ID NO:72.

In another embodiment, the antibody or binding protein of the invention is cross-blocked from binding to IL12Rβ1 by at least one of the antibodies mAb1-mAb16 defined above. Alternatively, the isolated antibody or binding protein of the invention may be selected among that which cross-blocks at least one of the antibodies mAb1-mAb16 from binding to IL12Rβ1.

The invention further relates to the use of said antibody or protein of the invention, in particular mAb1 to mAb16 antibodies, for use as a medicament, more preferably, for the treatment of a pathological disorder that is mediated by IL12Rβ1 or that can be treated by inhibiting IFNγ production, IL12 and/or IL23 signaling. In one specific embodiment, the antibodies or proteins of the invention may be used for the treatment of autoimmune and inflammatory disorders, such as rheumatoid arthritis, psoriasis or inflammatory bowel diseases.

The invention also encompasses pharmaceutical compositions comprising said antibody or proteins, in combination with one or more of a pharmaceutically acceptable excipient, diluent or carrier. In one specific embodiment, the pharmaceutical composition additionally comprises one or more other active ingredients.

In one specific embodiment, said pharmaceutical composition is a lyophilisate. In another specific embodiment, the pharmaceutical composition is a liquid formulation comprising a therapeutically acceptable amount of an antibody or protein of the invention, preferably prepared as a pre-filled syringe.

The invention also relates to the means for producing the antibodies or proteins of the invention. Such means include nucleic acid molecules encoding at least the heavy and/or light variable region(s) of the antibody or protein of the invention or cloning expression vectors comprising such nucleic acids, in particular, for the recombinant production of an antibody or protein according to the invention, for example, mAb1-mAb16, in a host cell. In a specific embodiment, such cloning or expression vector comprises at least one nucleic acid selected from the group consisting of SEQ ID NOs:73-88 and SEQ ID NOs:94-97. In another embodiment, it comprises either at least the following coding sequences of heavy and light chain sequences of any one of mAb1 to mAb16, operatively linked to suitable promoter sequences:
(a) mAb1: SEQ ID NO:73 and SEQ ID NO:85;
(b) mAb2: SEQ ID NO:77 and SEQ ID NO:85;
(c) mAb3: SEQ ID NO:81 and SEQ ID NO:85;
(d) mAb4: SEQ ID NO:74 and SEQ ID NO:86;
(e) mAb5: SEQ ID NO:78 and SEQ ID NO:86;
(f) mAb6: SEQ ID NO:82 and SEQ ID NO:86;
(g) mAb7: SEQ ID NO:75 and SEQ ID NO:87;
(h) mAb8: SEQ ID NO:79 and SEQ ID NO:87;
(i) mAb9: SEQ ID NO:83 and SEQ ID NO:87;
(j) mAb10: SEQ ID NO:76 and SEQ ID NO:88;
(k) mAb11: SEQ ID NO:80 and SEQ ID NO:88;
(l) mAb12: SEQ ID NO:84 and SEQ ID NO:88;
(m) mAb13: SEQ ID NO:94 and SEQ ID NO:85;
(n) mAb14: SEQ ID NO:95 and SEQ ID NO:86;
(o) mAb15: SEQ ID NO:96 and SEQ ID NO:87; or,
(p) mAb16: SEQ ID NO:97 and SEQ ID NO:88.

The invention further relates to a host cell comprising one or more cloning or expression vectors as described above and to the process for the production of an antibody or protein of the invention, in particular mAb1-mAb16, said process comprising culturing the host cell, purifying and recovering said antibody or protein.

In order that the present invention may be more readily understood, certain terms are first defined. Additional definitions are set forth throughout the detailed description.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" or "signaling activity" refers to a biochemical causal relationship generally initiated by a protein-protein interaction such as binding of a growth factor to a receptor, resulting in transmission of a signal from one portion of a cell to another portion of a cell. In general, the transmission involves specific phosphorylation of one or more tyrosine, serine, or threonine residues on one or more proteins in the series of reactions causing signal transduction. Penultimate processes typically include nuclear events, resulting in a change in gene expression.

The term IL12Rβ1 or IL12 receptor beta 1 refers to human IL12Rβ1 as defined in SEQ ID NO: 89, unless otherwise described.

The term p40 refers to human p40 subunit of human IL12 cytokine as defined in SEQ ID NO: 99, unless otherwise described.

The term p35 refers to human p35 subunit of human IL12 cytokine as defined in SEQ ID NO:100, unless otherwise described.

The term p19 refers to human p19 subunit of human IL23 cytokine as defined in SEQ ID NO:101, unless otherwise described.

The term "antibody" as referred to herein includes whole antibodies and any antigen binding fragments (i.e., "antigen-binding portion") or single chains thereof.

A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antigen portion"), as used herein, refers to full length or one or more fragments of an antibody that retain the ability to specifically bind to an antigen (e.g., a portion of IL12Rβ1). It has been shown that the antigen-binding function of an antibody can be performed by fragments of a full-length antibody. Examples of binding fragments encompassed within the term "antigen-binding portion" of an antibody include a Fab fragment, a monovalent fragment consisting of the $V_L$, $V_H$, $C_L$ and CH1 domains; a F(ab)$_2$ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated complementarity determining region (CDR), or any fusion proteins comprising such antigen-binding portion.

Furthermore, although the two domains of the Fv fragment, $V_L$ and $V_H$, are coded for by separate genes, they can be joined, using recombinant methods, by a synthetic linker that enables them to be made as a single chain protein in which the $V_L$ and $V_H$ regions pair to form monovalent molecules (known as single chain Fv (scFv); see e.g., Bird et al., 1988 Science 242:423-426; and Huston et al., 1988 Proc. Natl. Acad. Sci. 85:5879-5883). Such single chain antibodies are also intended to be encompassed within the term "antigen-binding portion" of an antibody. These antibody fragments are obtained using conventional techniques known to those of skill in the art, and the fragments are screened for utility in the same manner as are intact antibodies.

An "isolated antibody", as used herein, refers to an antibody that is substantially free of other antibodies having different antigenic specificities (e.g., an isolated antibody that specifically binds to IL12Rβ1 is substantially free of antibodies that specifically bind to other antigens than IL12Rβ1). An isolated antibody that specifically binds to IL12Rβ1 may, however, have cross-reactivity to other antigens, such as IL12Rβ1 molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutant versions of human germline sequences or antibody containing consensus framework sequences derived from human framework sequences analysis, for example, as described in Knappik, et al. (2000. J Mol Biol 296, 57-86).

The human antibodies of the invention may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human sequences.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM, IgE, IgG such as IgG1 or IgG4) that is provided by the heavy chain constant region genes.

The phrases "an antibody recognizing an antigen" and "an antibody specific for an antigen" are used interchangeably herein with the term "an antibody which binds specifically to an antigen".

As used herein, an antibody or a protein that "specifically binds to IL12Rβ1 polypeptide" is intended to refer to an antibody or protein that binds to human IL12Rβ1 polypeptide with a $K_D$ of 100 nM or less, 10 nM or less, 1 nM or less, 100 pM or less, or 10 pM or less. An antibody that "cross-reacts with an antigen other than IL12Rβ1" is intended to refer to an antibody that binds that antigen with a $K_D$ of 10 nM or less, 1 nM or less, or 100 pM or less. An antibody that "does not cross-react with a particular antigen" is intended to refer to an antibody that binds to that antigen, with a $K_D$ of 100 nM or greater, or a $K_D$ of 1 μM or grater, or a $K_D$ of 10 μM or greater. In certain embodiments, such antibodies that do not cross-react with the antigen exhibit essentially undetectable binding against these proteins in standard binding assays.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction.

The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, or using a biosensor system such as a Biacore® system. An assay for measuring anti-IL12Rβ1 antibody $K_D$ with the Biacore® system is described in the Examples below.

As used herein, the term "Affinity" refers to the strength of interaction between antibody and antigen at single antigenic sites. Within each antigenic site, the variable region of the antibody "arm" interacts through weak non-covalent forces with the antigen at numerous sites; the more interactions, the stronger the affinity.

As used herein, the term "Avidity" refers to an informative measure of the overall stability or strength of the antibody-antigen complex. It is controlled by three major factors: antibody epitope affinity; the valence of both the antigen and antibody; and the structural arrangement of the interacting parts. Ultimately these factors define the specificity of the antibody, that is, the likelihood that the particular antibody is binding to a precise antigen epitope.

As used herein, an antibody or protein that inhibits IL12 and/or IL23 binding to IL12Rβ1 polypeptide is intended to refer to an antibody or protein that inhibits IL12 and/or IL23 binding to IL12Rβ1 polypeptide with an $IC_{50}$ of 10 nM or less, preferably with an $IC_{50}$ of 1 nM or less, more preferably with an $IC_{50}$ of 100 pM, or less, as measured in an in vitro competitive binding assay such as Bioveris™ assay. Such assay is described in more details in the examples below.

As used herein, the term "IL12R antagonist" is intended to refer to an antibody or protein that inhibits IL12Rβ1 induced signaling activity in the presence of IL12 in a human cell assay such as the IL12 dependent IFNγ production assay in human blood cells. Such assay is described in more details in the examples below. In some embodiments, the antibodies or proteins of the invention inhibit IL12 dependent IFNγ production as measured in a human blood cell assay at an $IC_{50}$ of 10 nM or less, 1 nM or less, or 100 pM or less. Such assay is described in more details in the examples below.

As used herein, the term "IL23R antagonist" is intended to refer to an antibody that inhibits IL12Rβ1 induced signaling activity in the presence of IL23 in a human cell assay such as the IL23 dependent IFNγ production assay in human blood cell. Such assay is described in more details in the examples below. In some embodiments, the antibodies or binding protein of the invention inhibit IL23 IFNγ production as measured in a human blood cell assay at an $IC_{50}$ of 10 nM or less, 1 nM or less, or 100 pM or less. Such assay is described in more details in the examples below.

As used herein, an antibody with "no agonistic activity" is intended to refer to an antibody that does not significantly increase IL12Rβ1 mediated signaling activity in the absence of IL12 in a cell-based assay, such as the IL12 IFNγ production assay in human blood cell. Such assay is described in more details in the examples below.

As used herein, an antibody or protein that inhibits IL12 ex vivo IFNγ production in whole blood cell is intended to refer to an antibody or protein that decreases IL12 ex vivo IFNγ production to a level below 10% of the control level with an anti-IL12Rβ1 mAb plasma level above 10 μg/ml. In some embodiments, it refers to antibodies or proteins that completely abolish IL12 ex vivo IFNγ production in primate blood cell with anti-IL12Rβ1 mAb plasma levels above 10 μg/ml. Such assays are described in more details in the examples below.

As used herein, the term "ADCC" or "antibody dependent cell cytotoxicity" activity refers to cell depleting activity. ADCC activity can be measured by the ADCC assay as described in more details in the Examples below.

As used herein, the term "selectivity" for an antibody or protein of the invention refers to an antibody or protein that binds to a certain target polypeptide but not to closely related polypeptides.

As used herein, the term "high affinity" for an antibody refers to an antibody having a $K_D$ of 1 nM or less for a target antigen. As used herein, the term "subject" includes any human or nonhuman animal.

The term "nonhuman animal" includes all vertebrates, e.g., mammals and non-mammals, such as nonhuman primates, sheep, dogs, cats, horses, cows, chickens, amphibians, reptiles, etc.

As used herein, the term, "optimized" means that a nucleotide sequence has been altered to encode an amino acid sequence using codons that are preferred in the production cell or organism, generally a eukaryotic cell, for example, a cell of *Pichia*, a cell of *Trichoderma*, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in CHO mammalian cells, however optimized expression of these sequences in other eukaryotic cells is also envisioned herein. The amino acid sequences encoded by optimized nucleotide sequences are also referred to as optimized.

As used herein, the percent identity between the two sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described below.

The percent identity between two amino acid sequences can be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. Alternatively, the percent identity between two amino acid sequences can be determined using the Needleman and Wunsch (J. Mol, Biol. 48:444-453, 1970) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6.

The percent identity between two nucleotide amino acid sequences may also be determined using for example algorithms such as the BLASTN program for nucleic acid sequences using as defaults a word length (W) of 11, an expectation (E) of 10, M=5, N=4, and a comparison of both strands.

The terms "cross-block", "cross-blocked" and "cross-blocking" are used interchangeably herein to mean the ability of an antibody or other binding agent to interfere with the binding of other antibodies or binding agents to IL12Rβ1 in a standard competitive binding assay.

The ability or extent to which an antibody or other binding agent is able to interfere with the binding of another antibody or binding molecule to IL12Rβ1, and therefore whether it can be said to cross-block according to the invention, can be determined using standard competition binding assays. One suitable assay involves the use of the Biacore technology (e.g. by using the BIAcore 3000 instrument (Biacore, Uppsala, Sweden)), which can measure the extent of interactions using surface plasmon resonance technology. Another assay for measuring cross-blocking uses an ELISA-based approach. Further details on these methods are given in the Examples.

According to the invention, a cross-blocking antibody or other binding agent according to the invention binds to IL12Rβ1 in the described BIAcore cross-blocking assay such that the recorded binding of the combination (mixture) of the antibodies or binding agents is between 80% and 0.1% (e.g. 80% to 4%) of the maximum theoretical binding, specifically between 75% and 0.1% (e.g. 75% to 4%) of the maximum theoretical binding, and more specifically between 70% and 0.1% (e.g. 70% to 4%), and more specifically between 65% and 0.1% (e.g. 65% to 4%) of maximum theoretical binding (as defined above) of the two antibodies or binding agents in combination An antibody is defined as cross-blocking in the ELISA assay as described in the Examples, if the solution phase anti-IL12Rβ1 antibody is able to cause a reduction of between 60% and 100%, specifically between 70% and 100%, and more specifically between 80% and 100%, of the IL12Rβ1 detection signal (i.e. the amount of IL12Rβ1 bound by the coated antibody) as compared to the IL12Rβ1 detection signal obtained in the absence of the solution phase anti-IL12Rβ1 antibody (i.e. the positive control wells).

Recombinant Antibodies

Antibodies of the invention include the human recombinant antibodies mAb1-mAb16, isolated and structurally characterized by their full length heavy and light chain amino acid sequences as described in the Table 1 below:

TABLE 1

Full length heavy and light chain amino acid sequences of mAb1-mAb16

| Antibody | Full Length Heavy Chain Amino acid sequence | Full Length Light Chain Amino acid sequence |
| --- | --- | --- |
| mAb1 | SEQ ID NO: 57 | SEQ ID NO: 69 |
| mAb2 | SEQ ID NO: 61 | SEQ ID NO: 69 |
| mAb3 | SEQ ID NO: 65 | SEQ ID NO: 69 |
| mAb4 | SEQ ID NO: 58 | SEQ ID NO: 70 |
| mAb5 | SEQ ID NO: 62 | SEQ ID NO: 70 |
| mAb6 | SEQ ID NO: 66 | SEQ ID NO: 70 |
| mAb7 | SEQ ID NO: 59 | SEQ ID NO: 71 |
| mAb8 | SEQ ID NO: 63 | SEQ ID NO: 71 |
| mAb9 | SEQ ID NO: 67 | SEQ ID NO: 71 |
| mAb10 | SEQ ID NO: 60 | SEQ ID NO: 72 |
| mAb11 | SEQ ID NO: 64 | SEQ ID NO: 72 |
| mAb12 | SEQ ID NO: 68 | SEQ ID NO: 72 |
| mAb13 | SEQ ID NO: 90 | SEQ ID NO: 69 |
| mAb14 | SEQ ID NO: 91 | SEQ ID NO: 70 |
| mAb15 | SEQ ID NO: 92 | SEQ ID NO: 71 |
| mAb16 | SEQ ID NO: 93 | SEQ ID NO: 72 |

The corresponding variable regions, $V_H$ and $V_L$ amino acid sequences of such isolated antibodies mAb1-mAb16 of the invention are shown in the Table 2 below.

TABLE 2

Variable heavy and light chain amino acid sequences of mAb1-mAb16

| Antibody | Variable Heavy Chain Amino acid sequence | Variable Light Chain Amino acid sequence |
| --- | --- | --- |
| mAb1, mAb2, mAb3, mAb13 | SEQ ID NO: 49 | SEQ ID NO: 50 |
| mAb4, mAb5, mAb6, mAb14 | SEQ ID NO: 51 | SEQ ID NO: 52 |
| mAb7, mAb8, mAb9, mAb15 | SEQ ID NO: 53 | SEQ ID NO: 54 |
| mAb10, mAb11, mAb12, mAb16 | SEQ ID NO: 55 | SEQ ID NO: 56 |

Other antibodies of the invention include those having amino acids that have been mutated by amino acid deletion, insertion or substitution, yet have at least 60, 70, 80, 90, 95 or 100 percent identity in the CDR regions with the CDR regions depicted in the sequences described above. In some embodiments, the antibody of the invention is a mutant variant of any one of mAb1-mAb16, wherein said mutant variant antibody include mutant amino acid sequences wherein no more than 1, 2, 3, 4 or 5 amino acids have been mutated by amino acid deletion, insertion or substitution in the CDR regions when compared with the CDR regions depicted in the sequences described above.

Full length light and heavy chains nucleotide coding sequences of mAb1-mAb16 are shown in the Table 3 below.

TABLE 3

Full length heavy and light chain DNA coding sequences

| Antibody | Full Length Heavy Chain DNA coding sequence | Full Length Light Chain DNA coding sequence |
|---|---|---|
| mAb1 | SEQ ID NO: 73 | SEQ ID NO: 85 |
| mAb2 | SEQ ID NO: 77 | SEQ ID NO: 85 |
| mAb3 | SEQ ID NO: 81 | SEQ ID NO: 85 |
| mAb4 | SEQ ID NO: 74 | SEQ ID NO: 86 |
| mAb5 | SEQ ID NO: 78 | SEQ ID NO: 86 |
| mAb6 | SEQ ID NO: 82 | SEQ ID NO: 86 |
| mAb7 | SEQ ID NO: 75 | SEQ ID NO: 87 |
| mAb8 | SEQ ID NO: 79 | SEQ ID NO: 87 |
| mAb9 | SEQ ID NO: 83 | SEQ ID NO: 87 |
| mAb10 | SEQ ID NO: 76 | SEQ ID NO: 88 |
| mAb11 | SEQ ID NO: 80 | SEQ ID NO: 88 |
| mAb12 | SEQ ID NO: 84 | SEQ ID NO: 88 |
| mAb13 | SEQ ID NO: 94 | SEQ ID NO: 85 |
| mAb14 | SEQ ID NO: 95 | SEQ ID NO: 86 |
| mAb15 | SEQ ID NO: 96 | SEQ ID NO: 87 |
| mAb16 | SEQ ID NO: 97 | SEQ ID NO: 88 |

Other nucleic acids encoding antibodies of the invention include nucleic acids that have been mutated by nucleotide deletion, insertion or substitution, yet have at least 60, 70, 80, 90, 95 or 100 percent identity to the CDR corresponding coding regions depicted in the sequences described above or in Tables 4 and 5 below.

In some embodiments, it include variant nucleic acids wherein no more than 1, 2, 3, 4 or 5 nucleotides have been changed by nucleotide deletion, insertion or substitution in the CDR coding regions with the CDR coding regions depicted in the sequences described above or in Tables 4 and 5 below.

For antibodies that bind to the same epitope, the $V_H$, $V_L$, full length light chain, and full length heavy chain sequences (nucleotide sequences and amino acid sequences) can be "mixed and matched" to create other anti-IL12Rβ1 binding molecules of the invention. IL12Rβ1 binding of such "mixed and matched" antibodies can be tested using the binding assays described above or other conventional binding assays (e.g., ELISAs). When these chains are mixed and matched, a $V_H$ sequence from a particular $V_H/V_L$ pairing should be replaced with a structurally similar $V_H$ sequence. Likewise a full length heavy chain sequence from a particular full length heavy chain/full length light chain pairing should be replaced with a structurally similar full length heavy chain sequence. Likewise, a $V_L$ sequence from a particular $V_H/V_L$ pairing should be replaced with a structurally similar $V_L$ sequence. Likewise a full length light chain sequence from a particular full length heavy chain/full length light chain pairing should be replaced with a structurally similar full length light chain sequence. Accordingly, in one aspect, the invention provides an isolated recombinant antibody having: a heavy chain variable region comprising an amino acid sequence selected from the group consisting of SEQ ID NOs: 49, 51, 53 and 55; and a light chain variable region comprising an amino acid sequence selected from the group consisting of SEQ ID NOs: 50, 52, 54 and 56; wherein said heavy and light chain regions are selected such that the antibody specifically binds to IL12Rβ1.

Examples of the amino acid sequences of the $V_H$ CDR1s (also called HCDR1 or HCDR1' depending of the CDR definition that is used), $V_H$ CDR2s (also called HCDR2 or HCDR2' depending of the CDR definition that is used), $V_H$ CDR3s (also called HCDR1 or HCDR1' depending of the CDR definition that is used), $V_L$ CDR1s (also called LCDR1 or LCDR1' depending of the CDR definition that is used), $V_L$ CDR2s (also called LCDR2 or LCDR2' depending of the CDR definition that is used), $V_L$ CDR3s (also called HCDR3 or HCDR3' depending of the CDR definition that is used) of some antibodies according to the invention are shown in Tables 4 and 5 below.

In Table 4, the CDR regions of some antibodies of the invention are delineated using the Kabat system (Kabat, E. A., et al., 1991 Sequences of Proteins of Immunological Interest, Fifth Edition, U.S. Department of Health and Human Services, NIH Publication No. 91-3242, see also Zhao&Lu, 2009, Molecular Immunology 47: 694-700)

For the ease of reading, when CDR regions are delineated according to Kabat definition, they are called hereafter HCDR1, HCDR2, HCDR3, LCDR1, LCDR2, LCDR3 respectively.

TABLE 4

CDR regions of mAb1 to mAb16 according to Kabat definition

| Original antibody | HCDR1 | HCDR2 | HCDR3 | LCDR1 | LCDR2 | LCDR3 |
|---|---|---|---|---|---|---|
| mAb1, mAb2, mAb3, mAb13 | SEQ ID NO: 1 | SEQ ID NO: 2 | SEQ ID NO: 3 | SEQ ID NO: 4 | SEQ ID NO: 5 | SEQ ID NO: 6 |
| mAb4, mAb5, mAb6, mAb14 | SEQ ID NO: 7 | SEQ ID NO: 8 | SEQ ID NO: 9 | SEQ ID NO: 10 | SEQ ID NO: 11 | SEQ ID NO: 12 |
| mAb7, mAb8, mAb9, mAb15 | SEQ ID NO: 13 | SEQ ID NO: 14 | SEQ ID NO: 15 | SEQ ID NO: 16 | SEQ ID NO: 17 | SEQ ID NO: 18 |
| mAb10, mAb11, mAb12, mAb16 | SEQ ID NO: 19 | SEQ ID NO: 20 | SEQ ID NO: 21 | SEQ ID NO: 22 | SEQ ID NO: 23 | SEQ ID NO: 24 |

In Table 5, the CDR regions of some antibodies of the invention are delineated using the Chothia system, Al-Lazikani et al. 1997. J. Mol. Biol. 273, 927-948). For ease of reading, when the CDR regions are delineated according to Chothia definition, they are called hereafter HCDR1', HCDR2', HCDR3', LCDR1', LCDR2', LCDR3' respectively.

TABLE 5

CDR regions from mAb1 to mAb16 according to Chothia definition

| Original antibody | HCDR1' | HCDR2' | HCDR3' | LCDR1' | LCDR2' | LCDR3' |
|---|---|---|---|---|---|---|
| mAb1, mAb2, mAb3, mAb13 | SEQ ID NO: 25 | SEQ ID NO: 26 | SEQ ID NO: 27 | SEQ ID NO: 28 | SEQ ID NO: 29 | SEQ ID NO: 30 |
| mAb4, mAb5, mAb6, mAb14 | SEQ ID NO: 31 | SEQ ID NO: 32 | SEQ ID NO: 33 | SEQ ID NO: 34 | SEQ ID NO: 35 | SEQ ID NO: 36 |
| mAb7, mAb8, mAb9, mAb15 | SEQ ID NO: 37 | SEQ ID NO: 38 | SEQ ID NO: 39 | SEQ ID NO: 40 | SEQ ID NO: 41 | SEQ ID NO: 42 |
| mAb10, mAb11, mAb12, mAb16 | SEQ ID NO: 43 | SEQ ID NO: 44 | SEQ ID NO: 45 | SEQ ID NO: 46 | SEQ ID NO: 47 | SEQ ID NO: 48 |

Given that each of these antibodies can bind to IL12Rβ1 and that antigen-binding specificity is provided primarily by the CDR1, 2 and 3 regions, the $V_H$ CDR1, 2 and 3 sequences and $V_L$ CDR1, 2 and 3 sequences can be "mixed and matched" (i.e., CDRs from different antibodies can be mixed and matched, each antibody containing a $V_H$ CDR1, 2 and 3 and a $V_L$ CDR1, 2 and 3 create other anti-IL12Rβ1 binding molecules of the invention). IL12Rβ1 binding of such "mixed and matched" antibodies can be tested using the binding assays described above and in the Examples or other conventional assays (e.g., ELISAs). When $V_H$ CDR sequences are mixed and matched, the CDR1, CDR2 and/or CDR3 sequence from a particular $V_H$ sequence should be replaced with a structurally similar CDR sequence(s). Likewise, when $V_L$ CDR sequences are mixed and matched, the CDR1, CDR2 and/or CDR3 sequence from a particular $V_L$ sequence should be replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences shown herein for monoclonal antibodies of the present invention.

In one embodiment, an isolated recombinant antibody, or a protein comprising an antigen binding region thereof, has: a heavy chain variable region CDR1 comprising an amino acid sequence selected from the group consisting of SEQ ID NOs: 1, 7, 13 and 19; a heavy chain variable region CDR2 comprising an amino acid sequence selected from the group consisting of SEQ ID NOs: 2, 8, 14 and 20; a heavy chain variable region CDR3 comprising an amino acid sequence selected from the group consisting of SEQ ID NOs: 3, 9, 15 and 21; a light chain variable region CDR1 comprising an amino acid sequence selected from the group consisting of SEQ ID NOs: 4, 10, 16 and 22; a light chain variable region CDR2 comprising an amino acid sequence selected from the group consisting of SEQ ID NOs: 5, 11, 17 and 23; and a light chain variable region CDR3 comprising an amino acid sequence selected from the group consisting of SEQ ID NOs: 6, 12, 18 and 24; wherein said CDR regions are selected so that the antibody or protein of the invention specifically binds to IL12Rβ1.

In another embodiment, an isolated recombinant antibody, or a protein comprising an antigen binding region thereof has: a heavy chain variable region HCDR1' comprising an amino acid sequence selected from the group consisting of SEQ ID NOs: 25, 31, 37 and 43; a heavy chain variable region HCDR2' comprising an amino acid sequence selected from the group consisting of SEQ ID NOs: 26, 32, 38 and 44; a heavy chain variable region HCDR3' comprising an amino acid sequence selected from the group consisting of SEQ ID NOs: 27, 33, 39 and 45; a light chain variable region LCDR1' comprising an amino acid sequence selected from the group consisting of SEQ ID NOs: 28, 34, 40 and 46; a light chain variable region LCDR2' comprising an amino acid sequence selected from the group consisting of SEQ ID NOs: 29, 35, 41 and 47; and a light chain variable region LCDR3' comprising an amino acid sequence selected from the group consisting of SEQ ID NOs: 30, 36, 42 and 48; wherein said CDR regions are selected so that the antibody or protein of the invention specifically binds to IL12Rβ1.

In certain embodiments, the antibody or protein of the invention comprises either (a) a variable heavy chain amino acid sequence comprising HCDR1 of SEQ ID NO:1, HCDR2 of SEQ ID NO:2, HCDR3 of SEQ ID NO:3 and a variable light chain amino acid sequence comprising LCDR1 of SEQ ID NO:4, LCDR2 of SEQ ID NO:5 and LCDR3 of SEQ ID NO:6;

(b) a variable heavy chain amino acid sequence comprising HCDR1 of SEQ ID NO:7, HCDR2 of SEQ ID NO:8, HCDR3 of SEQ ID NO:9 and a variable light chain amino acid sequence comprising LCDR1 of SEQ ID NO:10, LCDR2 of SEQ ID NO:11 and LCDR3 of SEQ ID NO:12;

(c) a variable heavy chain amino acid sequence comprising HCDR1 of SEQ ID NO:13, HCDR2 of SEQ ID NO:14, HCDR3 of SEQ ID NO:15 and a variable light chain amino acid sequence comprising LCDR1 of SEQ ID NO:16, LCDR2 of SEQ ID NO:17 and LCDR3 of SEQ ID NO:18;

(d) a variable heavy chain amino acid sequence comprising HCDR1 of SEQ ID NO:19, HCDR2 of SEQ ID NO:20, HCDR3 of SEQ ID NO:21 and a variable light chain amino acid sequence comprising LCDR1 of SEQ ID NO:22, LCDR2 of SEQ ID NO:23 and LCDR3 of SEQ ID NO:24;

(e) a variable heavy chain amino acid sequence comprising HCDR1' of SEQ ID NO:25, HCDR2' of SEQ ID NO:26, HCDR3' of SEQ ID NO:27 and a variable light chain amino acid sequence comprising LCDR1' of SEQ ID NO:28, LCDR2' of SEQ ID NO:29 and LCDR3' of SEQ ID NO:30;

(f) a variable heavy chain amino acid sequence comprising HCDR1' of SEQ ID NO:31, HCDR2' of SEQ ID NO:32, HCDR3' of SEQ ID NO:33 and a variable light chain amino acid sequence comprising LCDR1' of SEQ ID NO:34, LCDR2' of SEQ ID NO:35 and LCDR3' of SEQ ID NO:36;

(g) a variable heavy chain amino acid sequence comprising HCDR1' of SEQ ID NO:37, HCDR2' of SEQ ID NO:38, HCDR3' of SEQ ID NO:39 and a variable light chain amino acid sequence comprising LCDR1' of SEQ ID NO:40, LCDR2' of SEQ ID NO:41 and LCDR3' of SEQ ID NO:42; or, (h) a variable heavy chain amino acid sequence comprising HCDR1' of SEQ ID NO:43, HCDR2' of SEQ ID NO:44, HCDR3' of SEQ ID NO:45 and a variable light chain amino acid sequence comprising LCDR1' of SEQ ID NO:46, LCDR2' of SEQ ID NO:47 and LCDR3' of SEQ ID NO:48.

As used herein, a human antibody comprises heavy or light chain variable regions or full length heavy or light chains that are "the product of" or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, an antibody or protein of the invention has full length heavy and light chain amino acid sequences; full length heavy and light chain nucleotide sequences, variable region heavy and light chain nucleotide sequences, or variable region heavy and light chain amino acid sequences, or all 6 CDR regions amino acid sequences or nucleotide coding sequences that are homologous to the amino acid or nucleotide sequences of the antibodies mAb1-mAb16 described above, in particular in Table 1, and wherein the antibodies or proteins of the invention retain the desired functional properties of the original mAb1-mAb16 antibodies.

Desired functional properties of the original mAb1-mAb16 antibodies may be selected from the group consisting of:

(i) the binding affinity to IL12Rβ1 (specific binding to IL12Rβ1), for example, a $K_D$ being 1 nM or less, 100 pM or less, or 10 pM or less, as measured in the Biacore assay described in the Examples;

(ii) competitive inhibition of IL12 or IL23 binding to IL12Rβ1, for example, an $IC_{50}$ being 10 nM or less, or 1 nM or less, or 100 pM or less, as measured in an IL12 or IL23 in vitro competitive binding assay as described in the Examples;

(iii) IL12 and/or IL23 dependent inhibition of IFNγ production in human blood cell, for example, an $IC_{50}$ being 10 nM or less, or 1 nM or less, or 100 pM or less, as measured in an IL12 or IL23 dependent IFNγ production in human blood cell assay as described in the Examples;

(iv) IL12 dependent inhibition of ex vivo IFN-γ production in primate blood cells;

(v) cross-reactivity with cynomolgous IL12Rβ1 polypeptide of SEQ ID NO:98;

(vi) suitable properties for drug development, in particular, it does not aggregate at in a formulation at high concentration, i.e., above 50 mg/ml; and, (vii) it has no or low ADCC activity.

For example, the invention relates to homologous antibodies of mAb1-mAb16 (or a binding protein comprising an antigen binding portion thereof), comprising a variable heavy chain ($V_H$) and a variable light chain ($V_L$) sequences where the CDR sequences, i.e. the 6 CDR regions; HCDR1, HCDR2, HCDR3, LCDR1, LCDR2, LCDR3 or HCDR1', HCDR2', HCDR3', LCDR1', LCDR2', LCDR3', share at least 60, 70, 90, 95 or 100 percent sequence identity to the corresponding CDR sequences of at least one antibody of mAb1-mAb16, wherein said homologous antibody or binding protein specifically binds to IL12Rβ1, and the antibody or binding protein exhibits at least one of the following functional properties: it inhibits IL12 and IL23 binding to IL12Rβ1, it inhibits IL12 dependent IFNγ production in human blood cells, it inhibits IL23 dependent IFNγ production in human blood cells, or it inhibits IL12 ex vivo IFN-γ production in primate blood cells. In a related specific embodiment, the homologous antibody or binding protein binds to IL12Rβ1 with a $K_D$ of 1 nM or less and inhibits IL12 and/or IL23 binding to IL12Rβ1 as measured in an in vitro competitive binding assay such as Bioveris™ assay with an $IC_{50}$ of 1 nM or less. The CDRs of mAb1-mAb16 are defined in the above Tables 4 and 5.

The invention further relates to homologous antibodies of mAb1-mAb16 (or a binding protein comprising an antigen binding portion thereof) comprising a heavy chain variable region and a light chain variable region that are at least 80%, 90%, or at least 95% or 100% identical to the corresponding heavy and light chain variable regions of any one of mAb1-mAb16 antibodies; the homologous antibody or binding protein specifically binds to IL12Rβ1, and it exhibits at least one of the following functional properties: it inhibits IL12 and IL23 binding to IL12Rβ1, it inhibits IL12 dependent IFNγ production in human blood cell, it inhibits IL23 dependent IFNγ production in human blood cells, or it inhibits IL12 ex vivo IFN-γ production in primate blood cells. In a related specific embodiment, the homologous antibody or binding protein binds to IL12Rβ1 with a $K_D$ of 1 nM or less and inhibits IL12 and/or IL23 binding to IL12Rβ1 as measured in an in vitro competitive binding assay such as Bioveris™ assay with an $IC_{50}$ of 1 nM or less. The $V_H$ and $V_L$ amino acid sequences of mAb1-mAb16 are defined in the above table 2.

In another example, the invention relates to homologous antibodies of mAb1-mAb16 (or a binding protein comprising an antigen binding portion thereof) comprising a full length heavy chain and a full length light chain, wherein: the variable heavy chain is encoded by a nucleotide sequence that is at least 80%, at least 90%, at least 95%, or 100% identical to the corresponding coding nucleotide sequence of the variable heavy and light chains of mAb1-mAb16, the homologous antibody or binding protein specifically binds to IL12Rβ1, and it exhibits at least one of the following functional properties: it inhibits IL12 and IL23 binding to IL12Rβ1, it inhibits IL12 dependent IFNγ production in human blood cells, it inhibits IL23 dependent IFNγ production in human blood cells, or it inhibits IL12 ex vivo IFN-γ production in primate blood cells. In a related specific embodiment, the homologous antibody or binding protein binds to IL12Rβ1 with a $K_D$ of 1 nM or less and inhibits IL12 and/or IL23 binding to IL12Rβ1 as measured in an in vitro competitive binding assay such as Bioveris™ assay with an $IC_{50}$ of 1 nM or less. The coding nucleotide sequences of the variable regions of mAb1 to mAb16 can be derived from the Table 3 showing the full length coding nucleotide sequences of mAb1-mAb16 and Table 2 showing the amino acid sequences of the variable regions of mAb1-mAb16.

In various embodiments, the antibody or binding protein comprising an antigen-binding portion of an antibody, may exhibit one or more, two or more, three or more, or four or more of the desired functional properties discussed above. The antibody or protein of the invention can be, for example, a human antibody, a humanized antibody or a chimeric antibody. Preferably the antibody or protein is a fully human silent antibody, preferably a fully human silent IgG1 antibody.

As used herein, the term "silent" antibody refers to an antibody that exhibits no or low ADCC activity as measured in an ADCC activity assay as described in the Examples.

In one embodiment, the term "no or low ADCC activity" means that the silent antibody exhibit an ADCC activity that is at below 50%, for example below 10% of the ADCC activity that is observed with the corresponding wild type (non silent) antibody.

Silenced effector functions can be obtained by mutation in the Fc constant part of the antibodies and have been described in the Art: Strohl 2009 (LALA & N297A); Baudino 2008, D265A (Baudino et al., J. Immunol. 181 (2008): 6664-69, Stroh), CO Biotechnology 20 (2009): 685-91). Examples of silent IgG1 antibodies comprise the so-called LALA mutant comprising L234A and L235A mutation in the IgG1 Fc amino acid sequence. Another example of a silent IgG1 antibody comprises the D265A mutation. Another silent IgG1 antibody comprises the N297A mutation, which results in aglycosylated or non-glycosylated antibodies.

Antibodies with mutant amino acid sequences can be obtained by mutagenesis (e.g., site-directed or PCR-mediated mutagenesis) of the coding nucleic acid molecules, followed by testing of the encoded altered antibody for retained function (i.e., the functions set forth above) using the functional assays described herein.

Antibodies with Conservative Modifications

In certain embodiments, an antibody (or a binding protein comprising antigen binding portion thereof) of the invention has a heavy chain variable region comprising HCDR1, HCDR2, and HCDR3 sequences (or HCDR1', HCDR2' and HCDR3') and a light chain variable region comprising LCDR1, LCDR2, and LCDR3 sequences (or LCDR1', LCDR2', and LCDR3'), wherein one or more of these CDR sequences have specified amino acid sequences based on the mAb1 to mAb16 antibodies described herein or conservative modifications thereof, and wherein the antibody or protein retains the desired functional properties of the anti-IL12Rβ1 antibodies of the invention.

As used herein, the term "conservative sequence modifications" is intended to refer to amino acid substitutions in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family, and the altered antibody can be tested for retained function using the functional assays described herein.

Modifications can be introduced into an antibody of the invention by standard techniques known in the art, such as site-directed mutagenesis and PCR-mediated mutagenesis.

Antibodies that Cross-Block any One of mAb1-mAb16 and/or that Bind to the Same Epitope as mAb1-mAb16

The antibodies mAb1-mAb16 have been shown to cross-compete at each other. Therefore, additional antibodies can therefore be identified based on their ability to cross-compete (e.g., to competitively inhibit the binding of), in a statistically significant manner with other antibodies of the invention, for example mAb1-mAb16, in standard IL12Rβ1 binding assays. Test antibody may first be screened for their binding affinity to IL12Rβ1, for example from human recombinant antibody libraries, using for example phage display technologies as described below. The ability of a test antibody to cross-compete with or inhibit the binding of antibodies of the present invention to human IL12Rβ1 demonstrates that the test antibody can compete with that antibody for binding to human IL12Rβ1; such an antibody may, according to non-limiting theory, bind to the same or a related (e.g., a structurally similar or spatially proximal) epitope on human IL12Rβ1 as the antibody with which it competes. Examples of Biacore or Elisa-based cross-blocking assays are described in detail in the Examples.

Accordingly, in one embodiment, the invention provides an isolated antibody or protein which cross-blocks or is cross-blocked by at least one antibody of mAb1-mAb16, from binding to IL12Rβ1, wherein said antibody or protein:
 (i) binds to the IL12Rβ1 polypeptide of SEQ ID NO:89 with a $K_D$ of 1 nM or less, and (ii) inhibits IL12 and/or IL23 binding to the IL12Rβ1 polypeptide of SEQ ID NO:89 as measured in an in vitro competitive binding assay.

In one specific embodiment, such cross-blocking anti-IL12Rβ1 antibody or protein of the invention further cross-react with cynomolgous IL12Rβ1 polypeptide of SEQ ID NO:98.

In another embodiment, the invention provides antibodies or proteins comprising the antigen-binding portion thereof, that bind to the same epitope as do the various specific anti-IL12Rβ1 antibodies mAb1-mAb16 as described herein.

In a certain embodiment, the cross-blocking antibodies or proteins or the antibody or protein that binds to the same epitope on human IL12Rβ1 as any one of mAb1-mAb16, is a human recombinant antibody. Such human recombinant antibodies can be prepared and isolated as described in the Examples.

Engineered and Modified Antibodies

Other antibodies or proteins comprising the antigen-binding portion thereof, of the invention can be prepared using an antibody having one or more of the $V_H$ and/or $V_L$ sequences of mAb1-mAb16 shown above as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chains complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad. See. U.S.A. 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of the invention pertains to an isolated recombinant CDR-grafted anti-IL12Rβ1 antibody, comprising the 6 CDR regions of any one of mAb1-mAb16 as defined in Table 4 or 5, yet containing different framework sequences from the original antibodies.

Such framework sequences can be obtained from public DNA databases or published references that include germline antibody gene sequences. For example, germline DNA sequences for human heavy and light chains variable region genes can be found in the "VBase" human germline sequence database (available on the Internet at www.mrc-cpe.cam.ac.uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. Mol. Biol. 227:776-798; and Cox, J. P. L. et al., 1994 Eur. J. Immunol. 24:827-836.

Examples of framework sequences are those that are structurally similar to the framework sequences used in any one of mAb1-mAb16. The $V_H$ CDR1, 2 and 3 sequences, and the $V_L$ CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the $V_H$ and/or $V_L$ CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Therefore, in one embodiment, the invention relates to affinity matured antibodies derived from one of mAb1-mAb16 antibodies. Conservative modifications (as discussed above) can be introduced. The mutations may be amino acid substitutions, additions or deletions. Moreover, typically no more than one, two, three, four or five residues within a CDR region are altered. For example, an antibody of the invention is an affinity-matured antibody comprising the 6 CDRs of one of mAb1-mAb16 and wherein no more than one, two, three, four or five residues within a CDR region are altered.

Accordingly, in another embodiment, the invention provides isolated engineered anti-IL12Rβ1 antibodies comprising a heavy chain variable region and a light chain variable region which are identical to the corresponding heavy and light chain variable regions of at least one of mAb1 to mAb16 antibodies except that the heavy and/or light chain amino acid sequences of said engineered antibodies contain one, two, three, four or five amino acid substitutions, deletions or additions as compared to the original sequences.

Grafting Antigen-Binding Domains into Alternative Frameworks or Scaffolds

A wide variety of antibody/immunoglobulin frameworks or scaffolds can be employed so long as the resulting polypeptide includes at least one binding region of mAb1 to mAb16, which specifically binds to IL12Rβ1. Such frameworks or scaffolds include the 5 main idiotypes of human immunoglobulins, or fragments thereof (such as those disclosed elsewhere herein), and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

In one aspect, the invention pertains to generating non-immunoglobulin based antibodies using non-immunoglobulin scaffolds onto which CDRs of the invention can be grafted. Known or future non-immunoglobulin frameworks and scaffolds may be employed, as long as they comprise a binding region specific for the target protein of SEQ ID NO: 89. Such compounds are referred herein as "polypeptides comprising a target-specific binding region". Examples of non-immunoglobulin framework are further described in the sections below (camelid antibodies and non-antibody scaffold).

Camelid Antibodies

Antibody proteins obtained from members of the camel and dromedary (*Camelus bactrianus* and *Calelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT Publication No. WO 94/04678.

A region of the camelid antibody which is the small single variable domain identified as $V_{HH}$ can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J. 17: 3512-3520. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule and the protein has a physical diameter of only a few nanometers. One consequence of the small size is the ability of camelid nanobodies to bind to antigenic sites that are functionally invisible to larger antibody proteins, i.e., camelid nanobodies are useful as reagents detecting antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitated drug transport across the blood brain barrier. See U.S. Patent Publication No. 20040161738 published Aug. 19, 2004. These features combined with the low antigenicity to humans indicate great therapeutic potential. Further, these molecules can be fully expressed in prokaryotic cells such as *E. coli* and are expressed as fusion proteins in bacteriophage and are functional.

Engineered nanobodies can further be customized by genetic engineering to have a half life in a recipient subject of from 45 minutes to two weeks. In a specific embodiment, the camelid antibody or nanobody is obtained by grafting the CDRs sequences of the heavy or light chain of one of the human antibodies of the invention, mAb1 to mAb16, into nanobody or single domain antibody framework sequences, as described for example in PCT Publication No. WO 94/04678.

Non-Antibody Scaffold

Known non-immunoglobulin frameworks or scaffolds include, but are not limited to, Adnectins (fibronectin) (Compound Therapeutics, Inc., Waltham, Mass.), ankyrin (Molecular Partners AG, Zurich, Switzerland), domain antibodies (Domantis, Ltd (Cambridge, Mass.) and Ablynx nv (Zwijnaarde, Belgium)), lipocalin (Anticalin) (Pieris Proteolab AG, Freising, Germany), small modular immunopharmaceuticals (Trubion Pharmaceuticals Inc., Seattle, Wash.), maxybodies (Avidia, Inc. (Mountain View, Calif.)), Protein A (Affibody AG, Sweden) and affilin (gamma-crystallin or ubiquitin) (Scil Proteins GmbH, Halle, Germany), protein epitope mimetics (Polyphor Ltd, Allschwil, Switzerland).

(i) Fibronectin Scaffold

The fibronectin scaffolds are based preferably on fibronectin type III domain (e.g., the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (U.S. Pat. No. 6,818,418).

These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of one of mAb1 to mAb16 using standard cloning techniques.

(ii) Ankyrin—Molecular Partners

The technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

(iii) Maxybodies/Avimers—Avidia

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, US Patent Publication Nos 20040175756; 20050053973; 20050048512; and 20060008844.

(vi) Protein A—Affibody

Affibody® affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate Affibody® libraries with a large number of ligand variants (See e.g., U.S. Pat. No. 5,831,012). Affibody® molecules mimic antibodies; they have a molecular weight of 6 kDa, compared to the molecular weight of antibodies, which is 150 kDa. In spite of its small size, the binding site of Affibody® molecules is similar to that of an antibody.

(v) Anticalins—Pieris

Anticalins® are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids.

The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain.

The set of four loops, which makes up the binding pocket, shows pronounced structural plasticity and tolerates a variety of side chains. The binding site can thus be reshaped in a proprietary process in order to recognize prescribed target molecules of different shape with high affinity and specificity.

One protein of lipocalin family, the bilin-binding protein (BBP) of *Pieris Brassicae* has been used to develop anticalins by mutagenizing the set of four loops. One example of a patent application describing "anticalins" is PCT Publication WO 199916873.

(vi) Affilin—Scil Proteins

Affilin™ molecules are small non-immunoglobulin proteins which are designed for specific affinities towards proteins and small molecules. New Affilin™ molecules can be very quickly selected from two libraries, each of which is based on a different human derived scaffold protein.

Affilin™ molecules do not show any structural homology to immunoglobulin proteins. Scil Proteins employs two Affilin™ scaffolds, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368

(vii) Protein Epitope Mimetics (PEM)

PEM are medium-sized, cyclic, peptide-like molecules (MW 1-2 kDa) mimicking beta-hairpin secondary structures of proteins, the major secondary structure involved in protein-protein interactions.

Framework or Fc Engineering

Engineered antibodies of the invention include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the invention.

Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below.

As used herein, the term "Fc region" is used to define the C-terminal region of an immunoglobulin heavy chain, including native sequence Fc region and variant Fc regions. The human IgG heavy chain Fc region is generally defined as comprising the amino acid residue from position C226 or from P230 to the carboxyl-terminus of the IgG antibody. The numbering of residues in the Fc region is that of the EU index of Kabat. The C-terminal lysine (residue K447) of the Fc region may be removed, for example, during production or purification of the antibody. Accordingly, a composition of antibodies of the invention may comprise antibody populations with all K447 residues removed, antibody populations with no K447 residues removed, and antibody populations having a mixture of antibodies with and without the K447 residue.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of $CH_1$ is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered Clq binding and/or reduced or abolished complement dependent cytotoxicity (CDC). This approach is described in further detail in U.S. Pat. No. 6,194,551 by Idusogie et at.

In another embodiment, one or more amino acid residues are altered to thereby alter the ability of the antibody to fix complement. This approach is described further in PCT Publication WO 94/29351 by Bodmer et at.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al., 2001 J. Biol. Chem. 276:6591-6604).

In certain embodiments, the Fc domain of the IgG1 isotype is used. In some specific embodiments, a mutant variant of the IgG1 Fc fragment is used, e.g. a silent IgG1 Fc which reduces or eliminates the ability of the fusion polypeptide to mediate antibody dependent cellular cytotoxicity (ADCC) and/or to bind to an Fcγ receptor. An example of an IgG1 isotype silent mutant is IgG1 wherein Leucineis replaced by Alanine at amino acid positions 234 and 235 as described in J. Virol 2001 December; 75(24):12161-8 by Hezareh et al. Another example of an IgG1 isotype silent mutant is IgG1 whith D265A mutation (aspartate being substituted by alanine at position 265).

In certain embodiments, the Fc domain is a silent Fc mutant preventing glycosylation at position 297 of the Fc domain. For example, the Fc domain contains an amino acid substitution of asparagine at position 297. An example of such amino acid substitution is the replacement of N297 by a glycine or an alanine.

In still another embodiment, the glycosylation of an antibody is modified. For example, an aglycoslated antibody can be made (i.e., the antibody lacks glycosylation). Glycosylation can be altered to, for example, increase the affinity of the antibody for the antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1 176 195 by Hang et al. describes a cell line with a functionally disrupted FUT8 gene, which encodes a fucosyl transferase, such that antibodies expressed in such a cell line exhibit hypofucosylation. Therefore, in one embodiment, the antibodies of the invention are produced by recombinant expression in a cell line which exhibits a hypofucosylation pattern, for example, a mammalian cell line with deficient expression of the FUT8 gene encoding fucosyltransferase. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180). Alternatively, the antibodies of the invention can be produced in a yeast or a filamentous fungus engineered for mammalian-like glycosylation pattern, and capable of producing antibodies lacking fucose as glycosylation pattern (see for example EP 1 297 172).

Another modification of the antibodies herein that is contemplated by the invention is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Another modification of the antibodies that is contemplated by the invention is a conjugate or a protein fusion of at least the antigen-binding region of the antibody of the invention to serum protein, such as human serum albumin or a fragment thereof to increase half-life of the resulting molecule. Such approach is for example described in Ballance et al. EP 0 322 094.

Another possibility is a fusion of at least the antigen-binding region of the antibody of the invention to proteins capable of binding to serum proteins, such human serum albumin to increase half life of the resulting molecule. Such approach is for example described in Nygren et al., EP 0 486 525.

Methods of Engineering Altered Antibodies

As discussed above, the anti-IL12Rβ1 antibodies having $V_H$ and $V_L$ sequences or full length heavy and light chain sequences shown herein can be used to create new anti-IL12Rβ1 antibodies by modifying full length heavy chain and/or light chain sequences, $V_H$ and/or $V_L$ sequences, or the constant region(s) attached thereto. Thus, in another aspect of the invention, the structural features of an anti-IL12Rβ1 antibody of the invention are used to create structurally related anti-IL12Rβ1 antibodies that retain at least one functional property of the antibodies of the invention, such as binding to human IL12Rβ1 and also inhibiting one or more functional properties of IL12Rβ1 (e.g., inhibiting IL12 and/or IL23 binding to IL12Rβ1, inhibiting IL12 induced IFNγ production in blood cells, etc).

For example, one or more CDR regions of any one of mAb1 to mAb16, or mutations thereof, can be combined recombinantly with known framework regions and/or other CDRs to create additional, recombinantly-engineered, anti-IL12Rβ1 antibodies of the invention, as discussed above. Other types of modifications include those described in the previous section. The starting material for the engineering method is one or more of the $V_H$ and/or $V_L$ sequences of mAb1-mAb16 provided in the tables above, or one or more CDR region thereof. To create the engineered antibody, it is not necessary to actually prepare (i.e., express as a protein) an antibody having one or more of the $V_H$ and/or $V_L$ sequences of mAb1 or mAb16, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

The second generation sequences are derived for example by altering the DNA coding sequence of at least one amino acid residue within the heavy chain variable region antibody sequence and/or the light chain variable region antibody sequence of any one of mAb1 to mAb16, to create at least one altered antibody sequence; and expressing the altered antibody sequence as a protein.

Accordingly, in another embodiment, the invention provides a method for preparing an anti-IL12Rβ1 antibody optimized for expression in a mammalian cell consisting of: a full length heavy chain antibody sequence a full length light chain antibody sequence of any one of mAb1 to mAb16; altering at least one codon in the nucleotide coding sequence, said codon encoding an amino acid residue within the full length heavy chain antibody sequence and/or the full length light chain antibody sequence to create at least one altered antibody sequence; and expressing the altered antibody sequence as a protein.

The altered antibody sequence can also be prepared by screening antibody libraries having unique heavy and light CDR3 sequences of any one of mAb1-mAb16 respectively, or minimal essential binding determinants as described in US Patent Publication No. 20050255552, and alternative sequences for CDR1 and CDR2 sequences. The screening can be performed according to any screening technology appropriate for screening antibodies from antibody libraries, such as phage display technology.

Standard molecular biology techniques can be used to prepare and express the altered antibody sequence. The antibody encoded by the altered antibody sequence(s) is one that retains one, some or all of the desired functional properties of the anti-IL12Rβ1 antibodies described herein, which functional properties include, but are not limited to, specifically binding to human IL12Rβ1; and/or it inhibits IL12 and IL23 binding to IL12Rβ1 polypeptide; and/or it inhibits IL12 induced IFNγ production in human blood cells; it inhibits IL23 induced IFNγ production in human blood cells; and/or it inhibits IL12 ex vivo IFN-γ production in primate blood cells.

The altered antibody may exhibit one or more, two or more, or three or more of the functional properties discussed above.

In certain embodiments of the methods of engineering antibodies of the invention, mutations can be introduced randomly or selectively along all or part of an anti-IL12Rβ1 antibody coding sequence and the resulting modified anti-IL12Rβ1 antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies of the Invention

Another aspect of the invention pertains to nucleic acid molecules that encode the antibodies or proteins of the invention. Examples of variable light chain nucleotide sequences are those encoding the variable light chain amino acid sequences of any one of mAb1 to mAb16, the latter sequences being derived from the Table 3 (showing the entire nucleotide coding sequences of heavy and light chains of mAb1 to mAb16) and Table 2 (showing the amino acid sequences of the variable regions of mAb1 to mAb16.

The invention also pertains to nucleic acid molecules that derive from the latter sequences having been optimized for protein expression in mammalian cells, for example, CHO cell lines.

The nucleic acids may be present in whole cells, in a cell lysate, or may be nucleic acids in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. 1987 Current Protocols in Molecular Biology, Greene Publishing and Wiley Interscience, New York. A nucleic acid of the invention can be, for example, DNA or RNA and may or may not contain intronic sequences. In an embodiment, the nucleic acid is a cDNA molecule. The nucleic acid may be present in a vector such as a phage display vector, or in a recombinant plasmid vector.

Nucleic acids of the invention can be obtained using standard molecular biology techniques. Once DNA fragments encoding, for example, $V_H$ and $V_L$ segments are obtained, these DNA fragments can be further manipulated by standard recombinant DNA techniques, for example to convert the variable region genes to full-length antibody chain genes, to Fab fragment genes or to an scFv gene. In these manipulations, a $V_L$- or $V_H$-encoding DNA fragment is operatively linked to another DNA molecule, or to a fragment encoding another protein, such as an antibody constant region or a flexible linker. The term "operatively linked", as used in this context, is intended to mean that the two DNA fragments are joined in a functional manner, for example, such that the amino acid sequences encoded by the two DNA fragments remain in-frame, or such that the protein is expressed under control of a desired promoter.

The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g., Kabat, E. A., et al., 1991 Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region. In some embodiments, the heavy chain constant region is selected among IgG1 isotypes. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as to a Fab light chain gene) by operatively linking the $V_L$-encoding DNA to another DNA molecule encoding the light chain constant region, CL. The sequences of human light chain constant region genes are known in the art (see e.g., Kabat, E. A., et al., 1991 Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or a lambda constant region.

To create an scFv gene, the $V_H$- and $V_L$-encoding DNA fragments are operatively linked to another fragment encoding a flexible linker, e.g., encoding the amino acid sequence (Gly4-Ser)$_3$, such that the $V_H$ and $V_L$ sequences can be expressed as a contiguous single-chain protein, with the $V_L$ and $V_H$ regions joined by the flexible linker (see e.g., Bird et al., 1988 Science 242:423-426; Huston et at., 1988 Proc. Natl. Acad. Sci. USA 85:5879-5883; McCafferty et al., 1990 Nature 348:552-554).

Isolation of Recombinant Antibodies of the Invention

A variety of methods of screening antibodies have been described in the Art. Such methods may be divided into in vivo systems, such as transgenic mice capable of producing fully human antibodies upon antigen immunization and in vitro systems, consisting of generating antibody DNA coding libraries, expressing the DNA library in an appropriate system for antibody production, selecting the clone that express antibody candidate that binds to the target with the affinity selection criteria and recovering the corresponding coding sequence of the selected clone. These in vitro technologies are known as display technologies, and include without limitation, phage display, RNA or DNA display, ribosome display, yeast or mammalian cell display. They have been well described in the Art (for a review see for example: Nelson et al., 2010 Nature Reviews Drug discovery, "Development trends for human monoclonal antibody therapeutics" (Advance Online Publication) and Hoogenboom et al. in Method in Molecular Biology 178:1-37, O'Brien et al., ed., Human Press, Totowa, N.J., 2001). In one specific embodiment, human recombinant antibodies of the invention are isolated using phage display methods for screening libraries of human recombinant antibody libraries, such as HuCAL® libraries.

Repertoires of $V_H$ and $V_L$ genes or related CDR regions can be separately cloned by polymerase chain reaction (PCR) or synthesized by DNA synthesizer and recombined randomly in phage libraries, which can then be screened for antigen-binding clones. Such phage display methods for isolating human antibodies are established in the art or described in the examples below. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

In a certain embodiment, human antibodies directed against IL12Rβ1 can be identified using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode un-rearranged human heavy (μ and γ) and κ light chain immunoglobulin sequences, together with targeted mutations that inactivate the endogenous μ and κ chain loci (see e.g., Lonberg, et al., 1994 Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al., 1994 supra; reviewed in Lonberg, N., 1994 Handbook of Experimental Pharmacology 113:49-101; Lonberg, N. and Huszar, D., 1995 Intern. Rev. Immunol. 13: 65-93, and Harding, F. and Lonberg, N., 1995 Ann. N.Y. Acad. Sci. 764:536-546). The preparation and use of HuMAb mice, and the genomic modifications carried by such mice, is further described in Taylor, L. et al., 1992 Nucleic Acids Research 20:6287-6295; Chen, J. et at., 1993 International Immunology 5: 647-656; Tuaillon et al., 1993 Proc. Natl. Acad. Sci. USA 94:3720-3724; Choi et al., 1993 Nature Genetics 4:117-123; Chen, J. et al., 1993 EMBO J. 12: 821-830; Tuaillon et al., 1994 J. Immunol. 152:2912-2920; Taylor, L. et al., 1994 International Immunology 579-591; and Fishwild, D. et al., 1996 Nature Biotechnology 14: 845-851. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92103918, WO 93/12227, WO 94/25585, WO 97113852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise anti-IL12Rβ1 antibodies of the invention. For example, an alternative transgenic system referred to as the Xenomouse (Abgenix, Inc.) can be used. Such mice are described in, e.g., U.S. Pat. Nos. 5,939,598; 6,075,181; 6,114, 598; 6, 150,584 and 6,162,963 to Kucherlapati et al.

Moreover, alternative transchromosomic animal systems expressing human immunoglobulin genes are available in the art and can be used to raise anti-IL12Rβ1 antibodies of the invention. For example, mice carrying both a human heavy chain transchromosome and a human light chain tranchromosome, referred to as "TC mice" can be used; such mice are described in Tomizuka et al., 2000 Proc. Natl. Acad. Sci. USA 97:722-727.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Generation of Monoclonal Antibodies of the Invention from the Murine System

Monoclonal antibodies (mAbs) can be produced by a variety of techniques, including conventional monoclonal antibody methodology e.g., the standard somatic cell hybridization technique of Kohler and Milstein, 1975 Nature 256: 495. Many techniques for producing monoclonal antibody can be employed e.g., viral or oncogenic transformation of B lymphocytes.

An animal system for preparing hybridomas is the murine system. Hybridoma production in the mouse is a well established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539 to Winter, and U.S. Pat. Nos. 5,530,101; 5,585,089; 5,693,762 and 6,180,370 to Queen et al.

Generation of Hybridomas Producing Human Monoclonal Antibodies

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific or epitope-specific antibodies. For example, single cell suspensions of splenic lymphocytes from immunized mice can be fused to one-sixth the number of P3X63-Ag8.653 nonsecreting mouse myeloma cells (ATCC, CRL 1580) with 50% PEG. Cells are plated at approximately 2×145 in flat bottom microtiter plates, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0:055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

Generation of Transfectomas Producing Monoclonal Antibodies

Antibodies of the invention can be produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains can be obtained by standard molecular biology or biochemistry techniques (e.g., DNA chemical synthesis, PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. 1990). It will be appreciated by those skilled in the art that the design of the expression vector, including the selection of regulatory sequences, may depend on such factors as the choice of the host cell to be transformed, the level of expression of protein desired, etc. Regulatory sequences for mammalian host cell expression include viral elements that direct high levels of protein expression in mammalian cells, such as promoters and/or enhancers derived from cytomegalovirus (CMV), Simian Virus 40 (SV40), adenovirus (e.g., the adenovirus major late promoter (AdMLP)), and polyoma. Alternatively, nonviral regulatory sequences may be used, such as the ubiquitin promoter or P-globin promoter. Still further, regulatory elements composed of sequences from different sources, such as the SRa promoter system, which contains sequences from the SV40 early promoter and the long terminal repeat of human T cell leukemia virus type 1 (Takebe, Y. et al., 1988 Mol. Cell. Biol. 8:466-472).

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is theoretically possible to express the antibodies of the invention in either prokaryotic or eukaryotic host cells. Expression of antibodies in eukaryotic cells, for example mammalian host cells, yeast or filamentous fungi, is discussed because such eukaryotic cells, and in particular mammalian cells, are more likely than prokaryotic cells to assemble and secrete a properly folded and immunologically active antibody.

In one specific embodiment, a cloning or expression vector according to the invention comprises either at least one of the following coding sequences (a)-(p) operatively linked to suitable promoter sequences selected from the group consisting of:
(a) SEQ ID NO:73 and SEQ ID NO:85;
(b) SEQ ID NO:77 and SEQ ID NO:85;
(c) SEQ ID NO:81 and SEQ ID NO:85;
(d) SEQ ID NO:74 and SEQ ID NO:86;
(e) SEQ ID NO:78 and SEQ ID NO:86;
(f) SEQ ID NO:82 and SEQ ID NO:86;
(g) SEQ ID NO:75 and SEQ ID NO:87;
(h) SEQ ID NO:79 and SEQ ID NO:87;
(i) SEQ ID NO:83 and SEQ ID NO:87;
(j) SEQ ID NO:76 and SEQ ID NO:88;
(k) SEQ ID NO:80 and SEQ ID NO:88;
(l) SEQ ID NO:84 and SEQ ID NO:88;
(m) SEQ ID NO:94 and SEQ ID NO:85;
(n) SEQ ID NO:95 and SEQ ID NO:86;
(o) SEQ ID NO:96 and SEQ ID NO:87; and,
(p) SEQ ID NO:97 and SEQ ID NO:88.

Mammalian host cells for expressing the recombinant antibodies of the invention include Chinese Hamster Ovary (CHO cells) (including dhfr-CHO cells, described Urlaub and Chasin, 1980 Proc. Natl. Acad. Sci. USA 77:4216-4220 used with a DH FR selectable marker, e.g., as described in R. J. Kaufman and P. A. Sharp, 1982 Mol. Biol. 159:601-621), CHOK1 dhfr+ cell lines, NSO myeloma cells, COS cells and SP2 cells. In particular, for use with NSO myeloma cells, another expression system is the GS gene expression system shown in PCT Publications WO 87/04462, WO 89/01036 and EP 0 338 841. In one embodiment, mammalian host cells for expressing the recombinant antibodies of the invention include mammalian cell lines deficient for FUT8 gene expression, for example as described in U.S. Pat. No. 6,946, 292.

When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods (See for example Abhinav et al. 2007, Journal of Chromatography 848: 28-37).

In one specific embodiment, the host cell of the invention is a host cell transfected with an expression vector having the coding sequences selected from the group consisting of (a)-(p) suitable for the expression of mAb1-mAb16 respectively, operatively linked to suitable promoter sequences:
(a) SEQ ID NO:73 and SEQ ID NO:85;
(b) SEQ ID NO:77 and SEQ ID NO:85;
(c) SEQ ID NO:81 and SEQ ID NO:85;
(d) SEQ ID NO:74 and SEQ ID NO:86;
(e) SEQ ID NO:78 and SEQ ID NO:86;
(f) SEQ ID NO:82 and SEQ ID NO:86;
(g) SEQ ID NO:75 and SEQ ID NO:87;
(h) SEQ ID NO:79 and SEQ ID NO:87;
(i) SEQ ID NO:83 and SEQ ID NO:87;
(j) SEQ ID NO:76 and SEQ ID NO:88;
(k) SEQ ID NO:80 and SEQ ID NO:88;
(l) SEQ ID NO:84 and SEQ ID NO:88;
(m) SEQ ID NO:94 and SEQ ID NO:85;
(n) SEQ ID NO:95 and SEQ ID NO:86;
(o) SEQ ID NO:96 and SEQ ID NO:87; and,
(p) SEQ ID NO:97 and SEQ ID NO:88.

The latter host cells may then be further cultured under suitable conditions for the expression and production of an antibody of the invention selected from the group consisting of mAb1-mAb16 respectively.

Immunoconjugates

In another aspect, the present invention features an anti-IL12Rβ1 antibody of the invention, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxon, cytochalasin B, gramicidin D, ethidium bromide, emetine, mitomycin, etoposide, tenoposide, vincristine, vinblastine, t. colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), ablating agents (e.g., mechlorethamine, thioepa chloraxnbucil, meiphalan, carmustine (BSNU) and lomustine (CCNU), cyclothosphamide, busulfan, dibromomannitol, streptozotocin, mitomycin C, and cis-dichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other examples of therapeutic cytotoxins that can be conjugated to an antibody of the invention include duocarmycins, calicheamicins, maytansines and auristatins, and derivatives thereof. An example of a calicheamicin antibody conjugate is commercially available (Mylotarg™; Wyeth-Ayerst).

Cytoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al., 2003 Adv. Drug Deliv. Rev. 55:199-215; Trail, P. A. et al., 2003 Cancer Immunol. Immunother. 52:328-337; Payne, G., 2003 Cancer Cell 3:207-212; Allen, T. M., 2002 Nat. Rev. Cancer 2:750-763; Pastan, I. and Kreitman, R. J., 2002 Curr. Opin. Investig. Drugs 3:1089-1091; Senter, P. D. and Springer, C. J., 2001 Adv. Drug Deliv. Rev. 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$, and lutetium$^{177}$. Method for preparing radioimmunconjugates are established in the art. Examples of radioimmunoconjugates are commercially available, including Zevalin™ (DEC Pharmaceuticals) and Bexxar™ (Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL1"), interleukin-2 ("IL2"), interleukin-6 ("IL6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et at., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Bispecific Molecules

In another aspect, the present invention features bispecific or multispecific molecules comprising an anti-IL12Rβ1 antibody of the invention. An antibody of the invention can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for IL12Rβ1, for example, one antigen-binding portion of any one of mAb1-mAb16 and a second binding specificity for a second target epitope. For example, the second target epitope is another epitope of IL12Rβ1 different from the first target epitope. Another example is a bispecific molecule comprising at least one first binding specificity for IL12Rβ1, for example, one antigen-binding portion of any one of mAb1-mAb16 and a second binding specificity for an epitope within IL12Rβ2 or IL23Rα.

Additionally, for the invention in which the bispecific molecule is multi-specific, the molecule can further include a third binding specificity, in addition to the first and second target epitope.

In one embodiment, the bispecific molecules of the invention comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778.

Other antibodies which can be employed in the bispecific molecules of the invention are murine, chimeric and humanized monoclonal antibodies.

The bispecific molecules of the present invention can be prepared by conjugating the constituent binding specificities, using methods known in the art. For example, each binding-specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio) propionate (SPDP), and sulfosuccinimidyl 4-(N-maleimidomethyl)cyclohaxane-1-carboxylate (sulfo-SMCC) (see e.g., Karpovsky et al., 1984 J. Exp. Med. 160: 1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particular embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand× Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

Multivalent Antibodies

In another aspect, the present invention provides multivalent antibodies comprising at least two identical or different antigen-binding portions of the antibodies of the invention binding to IL12Rβ1, for example, selected from antigen-binding portions of any one of mAb1-mAb16. In one embodiment, the multivalent antibodies provide at least two, three or four antigen-binding portions of the antibodies. The antigen-binding portions can be linked together via protein fusion or covalent or non covalent linkage. Alternatively, methods of linkage have been described for the bispecific molecules. Tetravalent compounds can be obtained for example by cross-linking antibodies of the antibodies of the invention with an antibody that binds to the constant regions of the antibodies of the invention, for example the Fc or hinge region.

Pharmaceutical Compositions

In another aspect, the present invention provides a composition, e.g., a pharmaceutical composition, containing one or a combination of antibodies of the present invention, for example, one antibody selected from the group consisting of mAb1-mAb16, formulated together with a pharmaceutically acceptable carrier. Such compositions may include one or a combination of (e.g., two or more different) antibodies, or immunoconjugates or bispecific molecules of the invention. For example, a pharmaceutical composition of the invention can comprise a combination of antibodies that bind to different epitopes on the target antigen or that have complementary activities.

Pharmaceutical compositions of the invention also can be administered in combination therapy, i.e., combined with other agents. For example, the combination therapy can include an anti-IL12Rβ1 antibody of the present invention, for example one antibody selected from the group consisting of mAb1-mAb16, combined with at least one other anti-inflammatory or another chemotherapeutic agent, for example, an immunosuppressant agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. The carrier should be suitable for intravenous, intramuscular, subcutaneous, parenteral, spinal or epidermal administration (e.g., by injection or infusion). In one embodiment, the carrier should be suitable for subcutaneous route. Depending on the route of administration, the active compound, i.e., antibody, immunoconjugate, or bispecific molecule, may be coated in a material to protect the compound from the action of acids and other natural conditions that may inactivate the compound.

The pharmaceutical compositions of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al., 1977 J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and di-carboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as, aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, one can include isotonic agents, for example, sugars, polyalcohols such as mannitol, sorbitol, or sodium chloride in the composition. Prolonged absorption of the injectable compositions can be brought about by including in the composition an agent that delays absorption for example, monostearate salts and gelatin.

Reviews on the development of stable protein (e.g; antibody) formulations may be found in Cleland et al. (1993) Crit. Reviews. Ther. Drug Carrier Systems 10(4):307-377 and Wei Wang (1999) Int. J. Pharmaceutcs 185:129-88. Additional formulation discussions for antibodies may be found, e.g., in Daugherty and Mrsny (2006) Advanced Drug Delivery Reviews 58: 686-706; U.S. Pat. Nos. 6,171,586, 4,618,486, US Publication No. 20060286103, PCT Publication WO 06/044908, WO 07/095,337, WO 04/016286, Colandene et al. (2007) J. Pharm. Sci 96: 1598-1608; Schulman (2001) Am. J. Respir. Crit. Care Med. 164:S6-S11 and other known references.

Solutions or suspensions used for intradermal or subcutaneous application typically include one or more of the following components: a sterile diluent such as water for injection, saline solution, fixed oils, polyethylene glycols, glycerine, propylene glycol or other synthetic solvents, antibacterial agents such as benzyl alcohol or methyl parabens, antioxidants such as ascorbic acid or sodium bisulfite, chelating agents such ethylenediaminetetraacetic acid, buffers such as acetates, citrates or phosphates, and agents for the adjustment of tonicity such as sodium chloride or dextrose. The pH can be adjusted with acids or bases, such as hydrochloric acid or sodium hydroxide. Such preparations may be enclosed in ampoules, disposables syringes or multiple dose vials made of glass or plastic.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the antibodies or proteins of the invention into a sterile vehicle that contains a basic dispersion medium and the required other ingredients from those enumerated above. In the case of sterile powders for the preparation of sterile injectable solutions, the methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, from about 0.1 percent to about 70 percent, or from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Dosage regimens for an anti-IL12Rβ1 antibody or protein of the invention include 1 mg/kg body weight or 3 mg/kg body weight by intravenous administration, with the antibody being given using one of the following dosing schedules: every four weeks for six dosages, then every three months; every three weeks; 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibodies or proteins of the invention are usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 μg/ml and in some methods about 25-300 μg/ml.

Alternatively, antibody or protein can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated or until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-IL12Rβ1 antibody or protein of the invention can result in a decrease in severity of disease symptoms, an increase in frequency and duration of disease symptom-free periods, or a prevention of impairment or disability due to the disease affliction.

A composition of the present invention can be administered by one or more routes of administration using one or more of a variety of methods known in the art. As will be appreciated by the skilled artisan, the route and/or mode of administration will vary depending upon the desired results. Routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion.

Alternatively, an antibody or protein of the invention can be administered by a non-parenteral route, such as a topical, epidermal or mucosal route of administration, for example, intranasally, orally, vaginally, rectally, sublingually or topically.

The antibodies or proteins of the invention can be prepared with carriers that will protect the antibodies against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in one embodiment, a therapeutic composition of the invention can be administered with a needleless hypodermic injection device, such as the devices shown in U.S. Pat. Nos. 5,399,163; 5,383, 851; 5,312,335; 5,064,413; 4,941,880; 4,790,824 or 4,596, 556. Examples of well known implants and modules useful in the present invention include: U.S. Pat. No. 4,487,603, which shows an implantable micro-infusion pump for dispensing medication at a controlled rate; U.S. Pat. No. 4,486,194, which shows a therapeutic device for administering medicants through the skin; U.S. Pat. No. 4,447,233, which shows a medication infusion pump for delivering medication at a precise infusion rate; U.S. Pat. No. 4,447,224, which shows a variable flow implantable infusion apparatus for continuous drug delivery; U.S. Pat. No. 4,439,196, which shows an osmotic drug delivery system having multi-chamber compartments; and U.S. Pat. No. 4,475,196, which shows an osmotic drug delivery system. Many other such implants, delivery systems, and modules are known to those skilled in the art.

In certain embodiments, the antibodies or proteins of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade, 1989 J. Cline Pharmacol. 29:685). Exemplary targeting moieties include folate or biotin (see, e.g., U.S. Pat. No. 5,416,016 to Low et al.); mannosides (Umezawa et al., 1988 Biochem. Biophys. Res. Commun. 153:1038); antibodies (P. G. Bloeman et al., 1995 FEBS Lett. 357:140; M. Owais et al., 1995 Antimicrob. Agents Chemother. 39:180); surfactant protein A receptor (Briscoe et al., 1995 Am. J. Physiol. 1233:134); p120 (Schreier et al., 1994 J. Biol. Chem. 269:9090); see also K. Keinanen; M. L. Laukkanen, 1994 FEBS Lett. 346:123; J. J. Killion; I. J. Fidler, 1994 lmrnunomethods 4:273.

Uses and Methods of the Invention

The antibodies or proteins of the present invention have in vitro and in vivo diagnostic and therapeutic utilities. For example, these molecules can be administered to cells in culture, e.g. in vitro or in vivo, or in a subject, e.g., in vivo, to treat, prevent or diagnose a variety of disorders.

The methods are particularly suitable for treating, preventing or diagnosing IL12Rβ1-related disorders and/or autoimmune and inflammatory disorders, e.g., rheumatoid arthritis, psoriasis or inflammatory bowel diseases.

The invention also provides methods for decreasing or suppressing IL12 or IL23 induced signaling response in human blood cells by administering a composition comprising a therapeutically efficient dose of the antibodies of the invention.

As used herein, an "IL12Rβ1-related disorder" includes conditions associated with or characterized by aberrant IL12 and/or IL23 levels and/or diseases or conditions that can be treated by reducing or suppressing IL12 and/or IL23 induced signaling activity in human blood cells e.g. the production of IFNγ or IL17 as measured in plasma or the extent of phosphorylation of STAT4 protein as measured by flow-cytometric methods or western blot. These include inflammatory conditions and autoimmune diseases, such as rheumatoid arthritis, psoriasis and inflammatory bowel diseases. These further include allergies and allergic conditions, hypersensitivity reactions, and organ or tissue transplant rejection.

For example, the antibodies or proteins of the invention may be used for the treatment of recipients of heart, lung, combined heart-lung, liver, kidney, pancreatic, skin or corneal transplants, including allograft rejection or xenograft rejection, and for the prevention of graft-versus-host disease, such as following bone marrow transplant, and organ transplant associated arteriosclerosis.

The antibodies or proteins of the invention are useful for the treatment, prevention, or amelioration of autoimmune disease and of inflammatory conditions, in particular inflammatory conditions with an aetiology including an autoimmune component such as arthritis (for example rheumatoid arthritis, arthritis chronica progrediente and arthritis deformans) and rheumatic diseases, including inflammatory conditions and rheumatic diseases involving bone loss, inflammatory pain, spondyloarhropathies including ankolsing spondylitis, Reiter syndrome, reactive arthritis, psoriatic arthritis, and enterophathis arthritis, hypersensitivity (including both airways hypersensitivity and dermal hypersensitivity) and allergies. Specific auto-immune diseases for which antibodies of the invention may be employed include autoimmune haematological disorders (including e.g. hemolytic anaemia, aplastic anaemia, pure red cell anaemia and idiopathic thrombocytopenia), systemic lupus erythematosus, inflammatory muscle disorders, polychondritis, sclerodoma, Wegener granulomatosis, dermatomyositis, chronic active hepatitis, myasthenia gravis, psoriasis, Steven-Johnson syndrome, idiopathic sprue, autoimmune inflammatory bowel disease (including e.g. ulcerative colitis, Crohn's disease and Irritable Bowel Syndrome), endocrine ophthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy), tumors, multiple sclerosis, inflammatory disease of skin and cornea, myositis, loosening of bone implants, metabolic disorders, such as atherosclerosis, diabetes, and dislipidemia.

The antibodies or proteins of the invention may also be useful for the treatment, prevention, or amelioration of asthma, bronchitis, pneumoconiosis, pulmonary emphysema, and other obstructive or inflammatory diseases of the airways.

The antibodies or proteins of the invention may also be useful for treating diseases of bone metabolism including osteoarthritis, osteoporosis and other inflammatory arthritides, and bone loss in general, including age-related bone loss, and in particular periodontal disease.

The antibodies or proteins of the invention may be administered as the sole active ingredient or in conjunction with, e.g. as an adjuvant to or in combination to, other drugs e.g. immunosuppressive or immunomodulating agents or other anti-inflammatory agents or other cytotoxic or anti-cancer agents, e.g. for the treatment or prevention of diseases mentioned above. For example, the antibodies of the invention may be used in combination with DMARD, e.g. Gold salts, sulphasalazine, antimalarias, methotrexate, D-penicillamine, azathioprine, mycophenolic acid, cyclosporine A, tacrolimus, sirolimus, minocycline, leflunomide, glucocorticoids; a calcineurin inhibitor, e.g. cyclosporin A or FK 506; a modulator of lymphocyte recirculation, e.g. FTY720 and FTY720 analogs; a mTOR inhibitor, e.g. rapamycin, 40-O-(2-hydroxyethyl)-rapamycin, CC1779, ABT578, AP23573 or TAFA-93; an ascomycin having immuno-suppressive properties, e.g. ABT-281, ASM981, etc.; corticosteroids; cyclophos-phamide; azathioprene; methotrexate; leflunomide; mizoribine; mycophenolic acid; myco-pheno-late mofetil; 15-deoxyspergualine or an immunosuppressive homologue, analogue or derivative thereof; immunosuppressive monoclonal antibodies, e.g., monoclonal antibodies to leukocyte receptors, e.g., MHC, CD2, CD3, CD4, CD7, CD8, CD25, CD28, CD40. CD45, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or a chemotherapeutic agent, e.g. paclitaxel, gemcitabine, cisplatinum, doxorubicin or 5-fluorouracil; anti TNF agents, e.g. monoclonal antibodies to TNF, e.g. infliximab, adalimumab, CDP870, or receptor constructs to TNF-RI or TNF-R11, e.g. Etanercept, PEG-TNF-R1; blockers of proinflammatory cytokines, IL1 blockers, e.g. Anakinra or IL1 trap, AAL160, IL17 blockers, IL13 blockers, IL4 blockers, IL6 blockers; chemokines blockers, e.g inhibitors or activators of proteases, e.g. metalloproteases, anti-IL15 antibodies, anti-IL6 antibodies, anti-IL17 antibodies, anti-IL4 antibodies, anti-IL13 antibodies, anti-$CD_2O$ antibodies, anti-Blys or anti-BAFFR antibodies, NSAIDs, such as aspirin or an anti-infectious agent (list not limited to the agent mentioned).

In accordance with the foregoing the present invention provides in a yet further aspect:

A method as defined above comprising co-administration, e.g. concomitantly or in sequence, of a therapeutically effective amount of an anti-IL12Rβ1 antibody or protein of the invention, and at least one second drug substance, said second drug substance being a immuno-suppressive/immunomodulatory, anti-inflammatory chemotherapeutic or anti-infectious drug, e.g. as indicated above.

Or, a therapeutic combination, e.g. a kit, comprising of a therapeutically effective amount of a) an antibody or protein of the invention, and b) at least one second substance selected from a immuno-suppressive/immunomodulatory, anti-inflammatory chemotherapeutic or anti-infectious drug, e.g. as indicated above. The kit may comprise instructions for its administration.

Where the antibodies of the invention are administered in conjunction with other immuno-suppressive/immunomodulatory, anti-inflammatory chemotherapeutic or anti-infectious therapy, dosages of the co-administered combination compound will of course vary depending on the type of co-drug employed, e.g. whether it is a DMARD, anti-TNF, IL1 blocker or others, on the specific drug employed, on the condition being treated and so forth.

In one specific embodiment, the antibodies of the invention may be administered in combination with anti TNF agents.

In another embodiment, the antibodies of the invention are administered only to patient population which is selected among patients suffering from systemic lupus eryhematous or rheumatoid arthritis and exhibiting an abnormal serum level of IL12 respectively IFNγ or IL17 or elevated levels and frequency of phosphoSTAT4 in blood cells. In other embodiment, the antibodies of the invention are administered only to patient population which is selected among group of patients which respond to anti-IL12 or anti-p40 treatment. Biomarkers that identify patients that have an increased likelihood of responding to anti-IL12 (or anti-p40) treatment may be any of the following without being limited to these: elevated levels of serum IL12, elevated levels of certain T cell subsets, mRNA levels of IFNγ, TNFα, IL12R132 or STAT4 from isolated peripheral blood mononuclear cells (PBMCs), phosphoSTAT4 expression in skin biopsies respectively PBMCs.

In one embodiment, the antibodies or proteins of the invention can be used to detect levels of IL12Rβ1, or levels of cells that contain IL12Rβ1. This can be achieved, for example, by contacting a sample (such as an in vitro sample) and a control sample with the anti-IL12Rβ1 antibody under conditions that allow for the formation of a complex between the antibody and IL12Rβ1. Any complexes formed between the antibody and IL12Rβ1 are detected and compared in the sample and the control. For example, standard detection methods, well known in the art, such as ELISA and flow cytometic assays, can be performed using the compositions of the invention.

Accordingly, in one aspect, the invention further provides methods for detecting the presence of IL12Rβ1 (e.g., human IL12Rβ1 antigen) in a sample, or measuring the amount of IL12Rβ1, comprising contacting the sample, and a control sample, with an antibody or protein of the invention, or an antigen binding region thereof, which specifically binds to IL12Rβ1, under conditions that allow for formation of a complex between the antibody or portion thereof and IL12Rβ1. The formation of a complex is then detected, wherein a difference in complex formation between the sample compared to the control sample is indicative of the presence of IL12Rβ1 in the sample.

Also within the scope of the invention are kits consisting of the compositions (e.g., antibodies, proteins, human antibodies and bispecific molecules) of the invention and instructions for use. The kit can further contain a least one additional reagent, or one or more additional antibodies or proteins of the invention (e.g., an antibody having a complementary activity which binds to an epitope on the target antigen distinct from the first antibody). Kits typically include a label indicating the intended use of the contents of the kit. The term label includes any writing, or recorded material supplied on or with the kit, or which otherwise accompanies the kit. The kit may further comprise tools for diagnosing whether a patient belongs to a group that will respond to an anti-IL12Rβ1 antibody treatment, as defined above.

The invention having been fully described is now further illustrated by the following examples and claims, which are illustrative and are not meant to be further limiting.

EXAMPLES

Methods
1. Affinity Determination Using Surface Plasmon Resonance (Biacore System)

For determination of $K_D$ values, surface plasmon resonance technology was applied using the Biacore™ technology. Anti-human-Fc-capture CM5 chip (Biacore, Sweden) was used for capturing IL12Rβ1-Fc-Fusion followed by ligand (Fab) injection at different concentrations.

2. IL 12Rβ1-IL12/IL23 In Vitro Competitive Binding Inhibition Assay (Bioveris)

The $IC_{50}$ represents the concentration of a Fab or IgG that was required for 50% inhibition of a receptor/ligand interaction. During the assay procedure, a fixed amount (predetermined to result in near maximum signal) of the receptor was incubated with increasing concentrations (1:100 to 100:1 molar ratio) of purified Fab/IgG in solution. Subsequently, the samples were transferred to a ligand coated and blocked MSD multi-titer plate. The free receptor binds to the ligand and was detected via an appropriate ruthenium complex-labeled antibody and quantified. The concentration of bound receptor as an inverse function of Fab/IgG concentration used for incubation was fitted using the respective model. The inflection point of the fitted curve represents the $IC_{50}$ value.

3. Inhibition of IL12-Dependent IFNγ Production of Human Blood Cells

Peripheral blood mononuclear cells (PBMCs) from donor blood were isolated via commonly used Ficoll/Histopaque gradient (Noble and Cutts, 1967 CanVetJ 8(5): 110-111). Cells were adjusted to 2E+6 cells/ml (in X-Vivo 15 medium). 50 μl cells (1 E+5) were transferred to a 96 well U bottom plate and incubated with inhibitory antibodies, e.g anti human IL12Rβ1Fabs or silent IgG1 or control mAbs or controls at desired concentrations and pre-incubated for 30 min at RT on a shaker. Stimulation with 2 pg/ml anti-CD3 and anti-CD28 mAbs and 2 ng/ml recombinant human cytokine IL12 was performed o/n, for 20 hrs at 37° C. in a 5% CO2 incubator. Next day, the supernatant was collected by centrifugation of the cells at 250 g for 5 min at RT and transferred to a fresh 96 well plate and used for ELISA determination or stored at −20° C. until assay was performed.

For the IFNγ ELISA the above collected supernatants were diluted in X-Vivo15 medium and the ELISA was performed according manufactures protocols BenderMed Systems #BMS228HS or Biozol/Biolegend #BLD-430105. IFNγ production was determined according to IFNγ standard titration curve.

4. Inhibition of IL23-Dependent IFNγ Production of Human Blood Cells

Another assay system was investigated, using PHA-stimulated PBMC. In this cell population, the T cells proliferate upon lectin exposure and thus the proportion of T cells in the population increases. In preliminary experiments, the responsiveness of these cells to IL-12, IL-23, IL-18 and LPS, alone or in combination was evaluated and the optimal stimulation conditions were established. The effects of IL-12+IL-18 and IL-23+IL-18 on IFN-γ secretion were induction of around 7 ng/ml and 800 pg/ml, respectively.

Alternatively, PBMCs from human donor blood were isolated by centrifugation over a density gradient and incubated with serial dilutions of IgGs for 30 min at RT. IL-18 and IL-23 were added and cells were incubated for 48 h at 37° C./5% $CO_2$. 5-fold diluted supernatants (in PBS/2 mM EDTA to achieve concentrations within the range of the standard curve 10 ng/ml-20 pg/ml) were taken to quantify IFN-γ by standard sandwich ELISA.

5. Inhibition of IL 12-Dependent IFNγ Production in Whole Blood

Aliquots of anti-coagulated blood of human or cynomolgous origin were distributed to individual wells of U-bottom 96 well plates (Costar, 3799) and serial dilutions of mAbs in X-Vivo 15 medium were added and incubated for 30 min at RT. After adding the human cytokines IL-12 and IL-18 the cells were incubated for 20-24 h at 37° C., 5% $CO_2$, before sampling the supernatants to quantify IFN-γ by ELISA.

6. ADCC Assay

In contrast to calcein, its acetoxy-methyl ester (Calcein-AM) is a compound able to pass cell membranes. Within the cell the ester bonds are hydrolyzed by cellular esterases. Thus the fluorescent calcein is trapped inside the cell. It will leak out only if membrane integrity is disturbed, i.e. if a cell is killed. Calcein-labelled target cells serve as targets for the NK effector cells, and the amount of calcein measured in the supernatant is proportional to the ability of a antibodies preparation to mediate ADCC.

For the NK3.3 assay it is necessary to starve the NK3.3 cells by culturing them in starvation medium (without IL-2 and IL-10) for two days.

Human IL-12Rβ1 transfected murine pre-B-cells were labelled with calcein and incubated with the antibodies to be tested. The human B cell line Raji expressing CD20 and anti-CD20 mAbs are used as controls for the killing activity of the NK3.3 cells. Spontaneous release from labelled cells only and background killing by the addition of NK3.3 cells without mAbs are also determined. In correlation with total release induced by cell lysis with Triton-X100 the % specific lysis is determined.

7. Cynomolgus Monkey Pharmacodynamics (PD) Assay

Heparinized blood samples were distributed in 96-U well plates (1090 μl/well). Recombinant human IL-12 (R&D Systems; 100 ng/ml final) and IL-18 (MBL; 50 ng/ml final) were added to each well and the plates were mixed gently for 3 minutes. After an incubation of 24 hrs at 37° C., in 6% $CO_2$, the plates were centrifuged at 2000 rpm for 10 min. The plasma were collected and kept at −80° C. until further processing.

IL-2, TNFα and IFN-γ determination was performed with NHP specific ELISA-kits (CT711, CT148 and CT141), as described by the manufacturer (UcyTech Biosciences, Utrecht).

For the PD readout, the results in pg of INFγ/ml were corrected by the number of lymphocytes found in each sample to be finally expressed as $pg/10^6$ lymphocyte.

8. Rat In Vivo Compatibility Assay

Rats are injected with defined doses of mAbs and blood samples taken at several intervals to monitor the peak plasma concentration and the rate of elimination to determine the plasma half life time. Since no cross-reactivity to the rat target is expected also no target-related effects (internalization, turnover) can be expected to influence results.

9. CD45RBhi Transfer Inflammatory Bowel Disease Mouse Model

To elicit the disease characterized by weight loss CD4+ CD45RBHi T lymphocytes are isolated from BALB/c mouse spleens by FACS-sorting and injected ($2 \times 10^5$ cells/mouse, i.p.) into 10 week old female SCID mice (day 0). Negative control mice receive PBS i.p. Groups of mice receive treatment by subcutaneous or intraperitoneal injection of mAbs (anti-IL12p40 clone C17.8 or anti-IL12Rβ1 antibody or isotype control) or PBS on d1, 7, 14 and 21. The body weight of each mouse is monitored throughout and at the end of the study. Histological examination of the terminal colon and determination of serum haptoglobin are determined at necropsy on d28.

10. Biacore Cross-Blocking Assay

The following generally describes a suitable Biacore assay for determining whether an antibody or other binding agent cross-blocks or was capable of cross-blocking antibodies according to the invention. It will be appreciated that the assay can be used with any of the IL12Rβ1 binding agents described herein.

The Biacore machine (for example the BIAcore 3000) is operated in line with the manufacturer's recommendations.

IL12Rβ1 extracellular domain may be coupled to e.g. a CM5 Biacore chip by way of routinely used amine coupling chemistry, e.g. EDC-NHS amine coupling, to create a IL12Rβ1-coated surface. In order to obtain measurable levels of binding, typically 200-800 resonance units of IL12Rβ1 may be coupled to the chip (this amount gives measurable levels of binding and is at the same time readily saturable by the concentrations of test reagent being used).

An alternative way of attaching IL12Rβ1 to the BIAcore chip is by using a "tagged" version of IL12Rβ1, for example N-terminal or C-terminal His-tagged IL12Rβ1. In this format, an anti-His antibody would be coupled to the Biacore chip and then the His-tagged IL12Rβ1 would be passed over the surface of the chip and captured by the anti-His antibody.

The two antibodies to be assessed for their ability to cross-block each other are mixed in a stoechiometrical amount, e.g. at a one to one molar ratio, of binding sites in a suitable buffer to create the test mixture. The buffer used is typically a buffer which is normally used in protein chemistry, such as e.g. PBS (136 mM NaCl, 2.7 mM KCl, 10 mM $Na_2HPO_4$, 1.76 mM $KH_2PO_4$, pH7.4). When calculating the concentrations on a binding site-basis the molecular weight of an antibody is assumed to be the total molecular weight of the antibody divided by the number of target (i.e. IL12Rβ1) binding sites on that antibody.

The concentration of each antibody in the test mixture should be high enough to ensure saturation of the binding sites for that antibody on the IL12Rβ1 molecule which are bound on the BIAcore chip. The antibodies in the mixture are at the same molar concentration (on a binding basis) and that concentration would typically be between 1.0 mM and 1.5 mM (on a binding site basis).

Separate solutions containing the separate antibodies on their own are also prepared. The buffer used for these separate solutions should be the same buffer and at the same concentration as is used for the test mixture.

The test mixture is passed over the IL12Rβ1-coated BIAcore chip and the binding recorded. The bound antibodies were thereafter removed by treating the chip with e.g. an acid, such as 30 mM HCl for about 1 minute. It is important that the IL12Rβ1 molecules which are bound to the chip are not damaged.

The solution of the first antibody alone is then passed over the IL12Rβ1-coated surface and the binding was recorded. Thereafter, the chip is treated to remove all of the bound antibody without damaging the chip-bound IL12Rβ1, e.g. by way of above mentioned acid treatment.

The solution of the second antibody alone is then passed over the IL12Rβ1-coated surface and the amount of binding recorded.

The maximal theoretical binding can be defined as the sum of the binding to IL12Rβ1 of each antibody separately. This is then compared to the actual binding of the mixture of antibodies measured. If the actual binding is lower than that of the theoretical binding, the two antibodies are cross-blocking each other.

11. ELISA-Based Cross-Blocking Assay

Cross-blocking of an anti-IL12Rβ1 antibody or another IL12Rβ1 binding agent may also be detected by using an ELISA assay.

The general principle of the ELISA-assay involves coating an anti-IL12Rβ1 antibody onto the wells of an ELISA plate. An excess amount of a second, potentially cross-blocking, anti-IL12Rβ1 antibody is then added in solution (i.e. not bound to the ELISA plate). A limited amount of IL12Rβ1-Fc is then added to the wells.

The antibody which is coated onto the wells and the antibody in solution will compete for binding of the limited number of IL12Rβ1 molecules. The plate is then washed to remove IL12Rβ1-Fc that has not bound to the coated antibody and to also remove the second, solution phase, antibody as well as any complexes formed between the second, solution phase antibody and IL12Rβ1-Fc. The amount of bound IL12Rβ1 is then measured using an appropriate IL12Rβ1 detection reagent. An antibody in solution that is able to cross-block the coated antibody will be able to cause a decrease in the number of IL12Rβ1 molecules that the coated antibody can bind relative to the number of IL12Rβ1 molecules that the coated antibody can bind in the absence of the second, solution phase, antibody.

This assay is described in more detail further below for two antibodies termed Ab-X and Ab-Y. In the instance where Ab-X is chosen to be the immobilized antibody, it is coated onto the wells of the ELISA plate, after which the plates are blocked with a suitable blocking solution to minimize non-specific binding of reagents that are subsequently added. An excess amount of Ab-Y is then added to the ELISA plate such that the moles of Ab-Y IL12Rβ1 binding sites per well are at least 10 fold higher than the moles of Ab-X IL12Rβ1 binding sites that are used, per well, during the coating of the ELISA plate. IL12Rβ1-Fc is then added such that the moles of IL12Rβ1-Fc added per well were at least 25-fold lower than the moles of Ab-X IL12Rβ1 binding sites that are used for coating each well. Following a suitable incubation period, the ELISA plate is washed and a IL12Rβ1 detection reagent is added to measure the amount of IL12Rβ1 specifically bound by the coated anti-IL12Rβ1 antibody (in this case Ab-X). The background signal for the assay is defined as the signal obtained in wells with the coated antibody (in this case Ab-X), second solution phase antibody (in this case Ab-Y), buffer only (i.e. no IL12Rβ1) and IL12Rβ1 detection reagents. The positive control signal for the assay is defined as the signal obtained in wells with the coated antibody (in this case Ab-X), second solution phase antibody buffer only (i.e. no second solution phase antibody), IL12Rβ1 and IL12Rβ1 detection reagents. The ELISA assay needs to be run in such a manner so as to have the positive control signal be at least 6 times the background signal.

To avoid any artifacts (e.g. significantly different affinities between Ab-X and Ab-Y for IL12Rβ1) resulting from the choice of which antibody to use as the coating antibody and which to use as the second (competitor) antibody, the cross-blocking assay needs to be run in two formats: 1) format 1 is where Ab-X is the antibody that is coated onto the ELISA plate and Ab-Y is the competitor antibody that is in solution and 2) format 2 is where Ab-Y is the antibody that is coated onto the ELISA plate and Ab-X is the competitor antibody that is in solution.

12. Cell Binding Assays

Cell binding of selected antibodies is tested using various IL-12Rβ1 expressing cell lines, e.g. Kit 225 or HSC-F, or human and cyno T cell blasts, employing flow cytometry. After incubation with serial antibody dilutions, staining of the cells is quantified by flow cytometric analysis.

13. Epitope Binning

Epitope binning experiments were done using flow cytometry. Kit 225 cells were incubated with a 100-fold excess of Fab-fragments and EC50 concentrations of IgGs. The IgGs binding to the cells were quantified with PE-labelled Fc-specific secondary antibody by Flowcytometry. Competition between the Fab and IgG for the same epitope or binding to the same displayed surface in a close-by area (same bin) resulted in diminished detection of the IgG.

14. Size Exclusion Chromatography Coupled with Multi-Angle Light Scattering Detector (SEC-MALS)

SEC-MALS measurements were performed on an Agilent 1200 HPLC system (Agilent Technologies) connected to a tri-angle light scattering detector (miniDAWN Treos, Wyatt Technology, Santa Barbara, Calif., USA). The concentration of the sample was followed online with a differential refractometer (Optilab rEX, Wyatt Technology) using a specific refractive index increment (dn/dc) value of 0.186 ml/g (Wen et al., 1996). Sample volumes of 50 μl were injected on a Superdex 200 10/300 GL column (GE Healthcare). The data were recorded and processed using the ASTRA V software (Wyatt Technology). To determine the detector delay volumes and normalization coefficients for the MALS detector, a BSA sample (Sigma, A8531) was used as reference. Neither despiking nor a band broadening correction was applied.

See also Wen, J., Arakawa, T., Philo, J. S., 1996. Anal. Biochem. 240, 155-166.

15. In Process Control of Antibody Concentrations in Cell Supernatants (Titer)

Concentration determinations of antibody-containing supernatants were performed on a HP1100 HPLC system (Agilent Technologies) employing protein A column. 62.5 μl protein A sepharose 4 fast flow (Amersham Biosciences) was packed into a HPLC cartridge. Running buffers were 50 mM $H_3BO_3$, 200 mM $Na_2SO_4$, where buffer A was adjusted to pH 7.5 using NaOH and buffer B to pH2.5 using $H_2SO_4$. The flow rate was 0.75 ml/min. Typically, 0.2 ml of supernatant was injected onto the protein A column. After rinsing with buffer A for 5.5 min, the bound antibody was eluted with buffer B for 2.5 min. The column was equilibrated with buffer A prior to the next sample injection. The 215 nm UV trace was monitored and the elution peak area or height was used for quantitation. A standard curve obtained from samples with different amounts of purified antibodies spiked into culture medium was used for calibration.

16. In Silico Prediction of the Isoelectric Point of Human Antibodies (pI)

The in-silico predicted pI was calculated by analyzing the primary amino acid sequence of the full antibody with the Novartis Biologics pI Calculator version 1.1 developed at NBx-PSP-CPD by Markus Heitzmann, Tina Buch, Salvatore Leonardi, Nora Eifler and Michael Vetsch. pK values are from Grimsley G R., Scholtz J M, and Pace C N. (2009) Protein Sci. 2009 18:247-51.

17. Protein A Recovery (%)

A multiwavelength nanodrop spectrophotometer ND1000 (Peqlab) was used to determine the concentration of the sample antibody after Protein A purification at a wavelength of 280 nm. Protein A recovery is the ratio of the total amount of purified antibody and amount of antibody in the cell supernatant measured by Protein A HPLC (see above).

18. Melting Point Determination of IgG's at pH7.4

The system used was a Thermofluor® iQTM 5 Optical System (BioRad Laboratories) and the software used was the iQTM 5 Optical System v2.0. The 96-well white microplates (Multiplate® PCR Plate™) were from Biorad (#MPL9561). The plates were sealed with a Microseal® 'B' Film. The SYPRO® Orange Protein Gel Stain was from Sigma (#S5692). The concentrated dye was diluted in dH2O prior to use (1.4 μl in 1 ml dH2O). 10 μl of antibody sample were added to 10 μl of 250 mM Sodiumphosphate buffer pH 7.4, 23 μl dH2O and 7 μl of the diluted dye. The final volume was 50 μl per well. The plates were sealed with a Microseal® 'B' Film using a handheld sealer (avoiding fingerprints) and the plates were centrifuged for 2 min at 1000 g. Tm measurements were done in the Thermofluor instrument by increasing the temperature from 20° C. until 95° C. in 0.5° C. increments during 90 min.

19. Melting Point Determination of Fabs at pH7.4, pH6.0, pH 3.5

The system used was a Thermofluor® iQTM 5 Optical System (BioRad Laboratories) and the software used was the iQTM 5 Optical System v2.0. The 96-well white microplates (Multiplate® PCR Plate™) were from Biorad (#MPL9561). The plates were sealed with a Microseal® 'B' Film. The SYPRO® Orange Protein Gel Stain was from Sigma (#S5692). The concentrated dye was diluted in dH2O prior to use (1.4 μl in 1 ml dH2O). 25 μl of E. coli expressed Fab sample were added to 18 μl of 50 mM citrate pH 3.5 or 100 mM MES pH6.0 or PBS and finally 7 μl of the diluted dye were included. The final volume was 50 μl per well. Plates were sealed with Microseal 'B' Adhesive Seals (BioRad, #MSB1001) using sealing tool, was mixed and spun down. Melting temperatures were measured by heating samples in an iQ™5 Multicolor Real Time PCR Detection System from 20 to 100° C. in increments of 0.5° C. Results were analyzed using iQ5.

20. Amide Hydrogen/Deuterium Exchange Mass Spectrometry Mapping of Epitopes

Amide Hydrogen/Deuterium exchange Mass Spectrometry (H/D×MS) was used to probe IL12Rbeta1 for information regarding the epitope for the following groups of antibodies: (i) mAb1, mAb2, mAb3, mAb13 (MOR11873), (ii) mAb4, mAb5, mAb6, mAb14 (MOR11878), and (iii) mAb10, mAb11, mAb12, mAb16 (MOR11880). H/D×MS mapping relies upon the mass difference between the isotopic masses of $^1H$ and $^2H$ (also called deuterium and abbreviated with the atom symbol D) or heavy hydrogen. Upon transfer from water ($H_2O$) to a heavy water ($D_2O$), a protein will experience an increase in mass as the protein's hydrogen atoms become gradually replaced with deuterons (i.e. the heavier isotope of hydrogen). The likelihood of a hydrogen/deuterium exchange events is largely determined by protein structure under physiological conditions. The structure controls the thermodynamic stability of the protein at a given site and the site-specific solvent accessibility. H/D×MS technology is used to measure the mass shifts of proteolytic fragments of the protein that result from deuterium incorporation into the protein under physiological conditions. These mass shifts indirectly report back on the local protein structural features (geometric and energetic). Of the exchangeable hydrogens in a protein only the amide hydrogens are observed in an H/D×MS analysis as it is not possible to stabilize the deuteration at other sites sufficiently to survive post-labeling analysis.

When a binding partner binds to an antibody target (e.g. antigen/antibody interaction), experimentally changes in hydrogen/deuterium exchange rate may be observed as a result of solvent exclusion and energetic stabilization of the local environment. Surface regions that are excluded from solvent access upon complex formation exchange much more slowly. Reduced exchange can therefore be directly used as an indication for a binding site. Specifically, in antigen-antibody interactions these changes might highlight the location of the epitope. This interpretation is complicated by the fact that changes (geometric and energetic) can occur elsewhere in the protein (allosteric changes) as the protein responds in cooperative manner to ligand binding. Allosteric effects on hydrogen-deuterium exchange cannot be discriminated against in a mass spectrometry based assay as no geometric/structural information is collected. Nevertheless, it is observed in practice that solvent exclusion explains mostly the protection patterns observed in protein-antigen complex formation as referenced toward the free antigen and that locations on the protein showing reduced exchange are highly indicative of a binding interface.

The location of reduced deuteron incorporation after antibody binding may be deduced by digestion of the target protein following hydrogen/deuterium exchange (e.g. with a suitable enzyme such as pepsin) and then mass spectrometry to determine the mass shift of the relevant fragments.

Experimental description: In the labeling experiment, the antigen (IL12Rbeta1) and the antigen-antibody complex were on-exchanged in solution at 0° C. for a predetermined time using an automated liquid handling system.

After the in-exchange period of 10 min samples are quenched to low pH (approx. 2.5 as this slows the exchange process of amide-hydrogens by five orders of magnitude as compared to pH 7.5) to stop the exchange and preserve the labeled state by addition of an excess of acidic quench buffer. Quenching to low pH provides enough stabilization of the labeled state (half-life ~30 min) for proteolysis (pepsin) and analysis by liquid chromatography mass spectrometry.

The differences in deuteration for the fragments from the antibody-antigen complex and the free antigen are inspected. Negative values are indicative of solvent protection in the antibody-antigen complex and interpreted as the most likely sites of interaction.

The results of this analysis, when conducted with representative antibodies from three groups of antibodies having the MOR#variable regions MOR11873, MOR11878, MOR11880 as set out in table 13, are provided in table 15 below.

Examples mAb1 to mAb16

Table 6 describes the amino acid sequences (SEQ ID NOs) of the full length heavy and light chains of examples mAb1 to mAb16.

TABLE 6

Examples mAb1-mAb16

| Antibody | Full Length Heavy Chain Amino acid sequence | Full Length Light Chain Amino acid sequence |
| --- | --- | --- |
| mAb1 | SEQ ID NO: 57 | SEQ ID NO: 69 |
| mAb2 | SEQ ID NO: 61 | SEQ ID NO: 69 |
| mAb3 | SEQ ID NO: 65 | SEQ ID NO: 69 |
| mAb4 | SEQ ID NO: 58 | SEQ ID NO: 70 |
| mAb5 | SEQ ID NO: 62 | SEQ ID NO: 70 |
| mAb6 | SEQ ID NO: 66 | SEQ ID NO: 70 |
| mAb7 | SEQ ID NO: 59 | SEQ ID NO: 71 |
| mAb8 | SEQ ID NO: 63 | SEQ ID NO: 71 |
| mAb9 | SEQ ID NO: 67 | SEQ ID NO: 71 |
| mAb10 | SEQ ID NO: 60 | SEQ ID NO: 72 |
| mAb11 | SEQ ID NO: 64 | SEQ ID NO: 72 |
| mAb12 | SEQ ID NO: 68 | SEQ ID NO: 72 |
| mAb13 | SEQ ID NO: 90 | SEQ ID NO: 69 |
| mAb14 | SEQ ID NO: 91 | SEQ ID NO: 70 |
| mAb15 | SEQ ID NO: 92 | SEQ ID NO: 71 |
| mAb16 | SEQ ID NO: 93 | SEQ ID NO: 72 |

The Examples mAb1 to mAb16 can be produced using conventional antibody recombinant production and purification processes. For example, the coding sequences as defined in Table 7 are cloned into a production vector for recombinant expression in mammalian production cell line.

TABLE 7

Coding DNA sequences of mAb1-mAb16

| Example | Full Length Heavy Chain DNA coding sequence | Full Length Light Chain DNA coding sequence |
| --- | --- | --- |
| mAb1 | SEQ ID NO: 73 | SEQ ID NO: 85 |
| mAb2 | SEQ ID NO: 77 | SEQ ID NO: 85 |
| mAb3 | SEQ ID NO: 81 | SEQ ID NO: 85 |
| mAb4 | SEQ ID NO: 74 | SEQ ID NO: 86 |
| mAb5 | SEQ ID NO: 78 | SEQ ID NO: 86 |
| mAb6 | SEQ ID NO: 82 | SEQ ID NO: 86 |

TABLE 7-continued

Coding DNA sequences of mAb1-mAb16

| Example | Full Length Heavy Chain DNA coding sequence | Full Length Light Chain DNA coding sequence |
| --- | --- | --- |
| mAb7 | SEQ ID NO: 75 | SEQ ID NO: 87 |
| mAb8 | SEQ ID NO: 79 | SEQ ID NO: 87 |
| mAb9 | SEQ ID NO: 83 | SEQ ID NO: 87 |
| mAb10 | SEQ ID NO: 76 | SEQ ID NO: 88 |
| mAb11 | SEQ ID NO: 80 | SEQ ID NO: 88 |
| mAb12 | SEQ ID NO: 84 | SEQ ID NO: 88 |
| mAb13 | SEQ ID NO: 94 | SEQ ID NO: 85 |
| mAb14 | SEQ ID NO: 95 | SEQ ID NO: 86 |
| mAb15 | SEQ ID NO: 96 | SEQ ID NO: 87 |
| mAb16 | SEQ ID NO: 97 | SEQ ID NO: 88 |

Other antibodies retaining substantially the same binding properties to IL12Rβ1 includes chimeric antibodies of any one of mAb1 to mAb16 which retain the same $V_H$ and $V_L$ regions of any one of mAb1 to mAb16 and different constant regions (for example a different Fc region selected from a different isotype, for example IgG4 or IgG2).

Table 8 summarizes the variable heavy ($V_H$) and light chain ($V_L$) amino acid sequence of mAb1 to mAb16 which can be used to generate chimeric antibodies from mAb1 to mAb16.

TABLE 8

Variable heavy ($V_H$) and light chain ($V_L$) amino acid sequence

| Original antibody | Variable Heavy Chain Amino acid sequence | Variable Light Chain Amino acid sequence |
| --- | --- | --- |
| mAb1, mAb2, mAb3, mAb13 | SEQ ID NO: 49 | SEQ ID NO: 50 |
| mAb4, mAb5, mAb6, mAb14 | SEQ ID NO: 51 | SEQ ID NO: 52 |
| mAb7, mAb8, mAb9, mAb15 | SEQ ID NO: 53 | SEQ ID NO: 54 |
| mAb10, mAb11, mAb12, mAb16 | SEQ ID NO: 55 | SEQ ID NO: 56 |

Other example antibodies, retaining substantially the same binding properties to IL12Rβ1 as mAb1-mAb16, include CDR grafted antibodies of any one of mAb1 to mAb16 by CDR grafting, retaining the CDR regions of any one of mAb1 to mAb16 with different framework and/or constant regions.

Table 9 summarizes the useful CDR sequences of mAb1 to mAb16 to generate alternative CDR grafted antibodies, wherein the CDR regions from mAb1 to mAb16 are defined according to Kabat definition.

Table 10 summarizes the useful CDR sequences of mAb1 to mAb16 to generate alternative CDR grafted antibodies, wherein the CDR regions from mAb1 to mAb16 are defined according to Chothia definition.

TABLE 9

CDR regions from mAb1 to mAb16 are defined according to Kabat definition

| Original Antibody | HCDR1 | HCDR2 | HCDR3 | LCDR1 | LCDR2 | LCDR3 |
| --- | --- | --- | --- | --- | --- | --- |
| mAb1, mAb2, mAb3, mAb13 | SEQ ID NO: 1 | SEQ ID NO: 2 | SEQ ID NO: 3 | SEQ ID NO: 4 | SEQ ID NO: 5 | SEQ ID NO: 6 |
| mAb4, mAb5, mAb6, mAb14 | SEQ ID NO: 7 | SEQ ID NO: 8 | SEQ ID NO: 9 | SEQ ID NO: 10 | SEQ ID NO: 11 | SEQ ID NO: 12 |

TABLE 9-continued

CDR regions from mAb1 to mAb16 are defined according to Kabat definition

| Original Antibody | HCDR1 | HCDR2 | HCDR3 | LCDR1 | LCDR2 | LCDR3 |
|---|---|---|---|---|---|---|
| mAb7, mAb8, mAb9, mAb15 | SEQ ID NO: 13 | SEQ ID NO: 14 | SEQ ID NO: 15 | SEQ ID NO: 16 | SEQ ID NO: 17 | SEQ ID NO: 18 |
| mAb10, mAb11, mAb12, mAb16 | SEQ ID NO: 19 | SEQ ID NO: 20 | SEQ ID NO: 21 | SEQ ID NO: 22 | SEQ ID NO: 23 | SEQ ID NO: 24 |

TABLE 10

CDR regions from mAb1 to mAb16 according to Chothia definition

| Original antibody | HCDR1' | HCDR2' | HCDR3' | LCDR1' | LCDR2' | LCDR3' |
|---|---|---|---|---|---|---|
| mAb1, mAb2, mAb3, mAb13 | SEQ ID NO: 25 | SEQ ID NO: 26 | SEQ ID NO: 27 | SEQ ID NO: 28 | SEQ ID NO: 29 | SEQ ID NO: 30 |
| mAb4, mAb5, mAb6, mAb14 | SEQ ID NO: 31 | SEQ ID NO: 32 | SEQ ID NO: 33 | SEQ ID NO: 34 | SEQ ID NO: 35 | SEQ ID NO: 36 |
| mAb7, mAb8, mAb9, mAb15 | SEQ ID NO: 37 | SEQ ID NO: 38 | SEQ ID NO: 39 | SEQ ID NO: 40 | SEQ ID NO: 41 | SEQ ID NO: 42 |
| mAb10, mAb11, mAb12, mAb16 | SEQ ID NO: 43 | SEQ ID NO: 44 | SEQ ID NO: 45 | SEQ ID NO: 46 | SEQ ID NO: 47 | SEQ ID NO: 48 |

Generation of anti-IL12Rbeta1 mAbs

Once a single, archetypal anti-human-IL12Rbeta1 antibody, for example any one of mAbs 1 to 16, has been isolated that has the desired properties described herein it is straightforward to generate other antibodies with similar properties, by using art-known methods. For example, mice may be immunized with IL12Rbeta1, hybridomas produced, and the resulting antibodies screened for binding to the IL12Rbeta1 polypeptide of SEQ ID NO:89. Alternatively, phage display methodologies may be used to generate other antibodies having specificity for the IL12Rbeta1 polypeptide of SEQ ID NO:89.

Such other antibodies having specificity for the IL12Rbeta1 polypeptide of SEQ ID NO:89 can then be screened for one or more of the following properties: a KD of 1 nM or less using Surface Plasmon Resonance (Biacore system), inhibition of IL12 and/or IL23 binding to the IL12Rbeta1 polypeptide of SEQ ID NO:89 as measured in an in vitro competitive binding assay, the ability to compete with the archetypal mAb for binding to IL12Rbeta1, as measured using Surface Plasmon Resonance (Biacore system) or Elisa-based cross-blocking assay, binding within or to the same epitope, as determined using amide Hydrogen/Deuterium exchange Mass Spectrometry. Alternatively, the method of Jespers et al., Biotechnology 12:899, 1994, which is incorporated herein by reference, may be used to guide the selection of mAbs having the same epitope and therefore similar properties to the archetypal mAb, e.g., one of any one of mAbs 1 to 16. Using phage display, first the heavy chain of the archetypal antibody is paired with a repertoire of (preferably human) light chains to select an IL12Rbeta1-binding mAb, and then the new light chain is paired with a repertoire of (preferably human) heavy chains to select a (preferably human) IL12Rbeta1-binding mAb having the same epitope as the archetypal mAb.

For example, to identify other antibodies binding within or to the epitope described herein, the antibodies can be generated as described above, and then screened for binding to or within the epitope using amide Hydrogen/Deuterium exchange Mass Spectrometry. Alternatively, to identify those other antibodies which compete with the archetypal mAb for binding to IL12Rbeta1, the antibodies can be generated as described above, and then screened for competition using Surface Plasmon Resonance (Biacore system) or Elisa-based cross-blocking assay.

To identify other antibodies having the functional properties described herein, the antibodies can be generated as described above, and then screened for a KD of 1 nM or less using Surface Plasmon Resonance (Biacore system), and inhibition of IL12 and/or IL23 binding to the IL12Rbeta1 polypeptide of SEQ ID NO:89 as measured in an in vitro competitive binding assay.

To identify other antibodies having the functional properties described herein and which bind within or to the epitope described herein, the antibodies can be generated as described above, screened for a KD of 1 nM or less using Surface Plasmon Resonance (Biacore system), and inhibition of IL12 and/or IL23 binding to the IL12Rbeta1 polypeptide of SEQ ID NO:89 as measured in an in vitro competitive binding assay, and screened for binding to or within the epitope using amide Hydrogen/Deuterium exchange Mass Spectrometry.

To identify other antibodies having the functional properties described herein and which compete with the archetypal mAb for binding to IL12Rbeta1, the antibodies can be generated as described above, screened for a KD of 1 nM or less using Surface Plasmon Resonance (Biacore system), screened for inhibition of IL12 and/or IL23 binding to the IL12Rbeta1 polypeptide of SEQ ID NO:89 as measured in an in vitro competitive binding assay, and screened for competition using Surface Plasmon Resonance (Biacore system) or Elisa-based cross-blocking assay.

TABLE 11

Brief description of useful amino acid and nucleotide sequences for practicing the invention

| SEQ ID NO: | Description of the sequence |
|---|---|
| 1 | HCDR1 amino acid sequence of MOR11873 according to Kabat definition |
| 2 | HCDR2 amino acid sequence of MOR11873 according to Kabat definition |
| 3 | HCDR3 amino acid sequence of MOR11873 according to Kabat definition |
| 4 | LCDR1 amino acid sequence of MOR11873 according to Kabat definition |
| 5 | LCDR2 amino acid sequence of MOR11873 according to Kabat definition |
| 6 | LCDR3 amino acid sequence of MOR11873 according to Kabat definition |
| 7 | HCDR1 amino acid sequence of MOR11878 according to Kabat definition |
| 8 | HCDR2 amino acid sequence of MOR11878 according to Kabat definition |
| 9 | HCDR3 amino acid sequence of MOR11878 according to Kabat definition |

TABLE 11-continued

Brief description of useful amino acid and nucleotide sequences for practicing the invention

| SEQ ID NO: | Description of the sequence |
|---|---|
| 10 | LCDR1 amino acid sequence of MOR11878 according to Kabat definition |
| 11 | LCDR2 amino acid sequence of MOR11878 according to Kabat definition |
| 12 | LCDR3 amino acid sequence of MOR11878 according to Kabat definition |
| 13 | HCDR1 amino acid sequence of MOR11879 according to Kabat definition |
| 14 | HCDR2 amino acid sequence of MOR11879 according to Kabat definition |
| 15 | HCDR3 amino acid sequence of MOR11879 according to Kabat definition |
| 16 | LCDR1 amino acid sequence of MOR11879 according to Kabat definition |
| 17 | LCDR2 amino acid sequence of MOR11879 according to Kabat definition |
| 18 | LCDR3 amino acid sequence of MOR11879 according to Kabat definition |
| 19 | HCDR1 amino acid sequence of MOR11880 according to Kabat definition |
| 20 | HCDR2 amino acid sequence of MOR11880 according to Kabat definition |
| 21 | HCDR3 amino acid sequence of MOR11880 according to Kabat definition |
| 22 | LCDR1 amino acid sequence of MOR11880 according to Kabat definition |
| 23 | LCDR2 amino acid sequence of MOR11880 according to Kabat definition |
| 24 | LCDR3 amino acid sequence of MOR11880 according to Kabat definition |
| 25 | HCDR1' amino acid sequence of MOR11873 according to Chothia definition |
| 26 | HCDR2' amino acid sequence of MOR11873 according to Chothia definition |
| 27 | HCDR3' amino acid sequence of MOR11873 according to Chothia definition |
| 28 | LCDR1' amino acid sequence of MOR11873 according to Chothia definition |
| 29 | LCDR2' amino acid sequence of MOR11873 according to Chothia definition |
| 30 | LCDR3' amino acid sequence of MOR11873 according to Chothia definition |
| 31 | HCDR1' amino acid sequence of MOR11878 according to Chothia definition |
| 32 | HCDR2' amino acid sequence of MOR11878 according to Chothia definition |
| 33 | HCDR3' amino acid sequence of MOR11878 according to Chothia definition |
| 34 | LCDR1' amino acid sequence of MOR11878 according to Chothia definition |
| 35 | LCDR2' amino acid sequence of MOR11878 according to Chothia definition |
| 36 | LCDR3' amino acid sequence of MOR11878 according to Chothia definition |
| 37 | HCDR1' amino acid sequence of MOR11879 according to Chothia definition |
| 38 | HCDR2' amino acid sequence of MOR11879 according to Chothia definition |
| 39 | HCDR3' amino acid sequence of MOR11879 according to Chothia definition |
| 40 | LCDR1' amino acid sequence of MOR11879 according to Chothia definition |
| 41 | LCDR2' amino acid sequence of MOR11879 according to Chothia definition |
| 42 | LCDR3' amino acid sequence of MOR11879 according to Chothia definition |
| 43 | HCDR1' amino acid sequence of MOR11880 according to Chothia definition |
| 44 | HCDR2' amino acid sequence of MOR11880 according to Chothia definition |
| 45 | HCDR3' amino acid sequence of MOR11880 according to Chothia definition |
| 46 | LCDR1' amino acid sequence of MOR11880 according to Chothia definition |
| 47 | LCDR2' amino acid sequence of MOR11880 according to Chothia definition |
| 48 | LCDR3' amino acid sequence of MOR11880 according to Chothia definition |
| 49 | $V_H$ amino acid sequence of MOR11873 |
| 50 | $V_L$ amino acid sequence of MOR11873 |
| 51 | $V_H$ amino acid sequence of MOR11878 |
| 52 | $V_L$ amino acid sequence of MOR11878 |
| 53 | $V_H$ amino acid sequence of MOR11879 |
| 54 | $V_L$ amino acid sequence of MOR11879 |
| 55 | $V_H$ amino acid sequence of MOR11880 |
| 56 | $V_L$ amino acid sequence of MOR11880 |
| 57 | Full length heavy chain of MOR11873 with IgG1 LALA Fc variant |
| 58 | Full length heavy chain of MOR11878 with IgG1 LALA Fc variant |
| 59 | Full length heavy chain of MOR11879 with IgG1 LALA Fc variant |
| 60 | Full length heavy chain of MOR11880 with IgG1 LALA Fc variant |
| 61 | Full length heavy chain of MOR11873 with IgG1 D265A Fc variant |
| 62 | Full length heavy chain of MOR11878 with IgG1 D265A Fc variant |
| 63 | Full length heavy chain of MOR11879 with IgG1 D265A Fc variant |
| 64 | Full length heavy chain of MOR11880 with IgG1 D265A Fc variant |
| 65 | Full length heavy chain of MOR11873 with IgG1 N297A Fc variant |
| 66 | Full length heavy chain of MOR11878 with IgG1 N297A Fc variant |
| 67 | Full length heavy chain of MOR11879 with IgG1 N297A Fc variant |
| 68 | Full length heavy chain of MOR11880 with IgG1 N297A Fc variant |
| 69 | Full length light chain of MOR11873 |
| 70 | Full length light chain of MOR11878 |
| 71 | Full length light chain of MOR11879 |
| 72 | Full length light chain of MOR11880 |
| 73 | Nucleotide sequence encoding Full length heavy chain of MOR11873 with IgG1 LALA Fc variant |
| 74 | Nucleotide sequence encoding Full length heavy chain of MOR11878 with IgG1 LALA Fc variant |
| 75 | Nucleotide sequence encoding Full length heavy chain of MOR11879 with IgG1 LALA Fc variant |
| 76 | Nucleotide sequence encoding Full length heavy chain of MOR11880 with IgG1 LALA Fc variant |
| 77 | Nucleotide sequence encoding Full length heavy chain of MOR11873 with IgG1 D265A Fc variant |
| 78 | Nucleotide sequence encoding Full length heavy chain of MOR11878 with IgG1 D265A Fc variant |
| 79 | Nucleotide sequence encoding Full length heavy chain of MOR11879 with IgG1 D265A Fc variant |
| 80 | Nucleotide sequence encoding Full length heavy chain of MOR11880 with IgG1 D265A Fc variant |
| 81 | Nucleotide sequence encoding Full length heavy chain of MOR11873 with IgG1 N297A Fc variant |
| 82 | Nucleotide sequence encoding Full length heavy chain of MOR11878 with IgG1 N297A Fc variant |
| 83 | Nucleotide sequence encoding Full length heavy chain of MOR11879 with IgG1 N297A Fc variant |
| 84 | Nucleotide sequence encoding Full length heavy chain of MOR11880 with IgG1 N297A Fc variant |
| 85 | Nucleotide sequence encoding Full length light chain of MOR11873 |
| 86 | Nucleotide sequence encoding Full length light chain of MOR11878 |
| 87 | Nucleotide sequence encoding Full length light chain of MOR11879 |
| 88 | Nucleotide sequence encoding Full length light chain of MOR11880 |
| 89 | Amino acid sequence of human IL12Rbeta1 |
| 90 | Full length heavy chain of MOR11873 with IgG1 Fc wild type |

TABLE 11-continued

Brief description of useful amino acid and nucleotide sequences for practicing the invention

| SEQ ID NO: | Description of the sequence |
|---|---|
| 91 | Full length heavy chain of MOR11878 with IgG1 Fc wild type |
| 92 | Full length heavy chain of MOR11879 with IgG1 Fc wild type |
| 93 | Full length heavy chain of MOR11880 with IgG1 Fc wild type |
| 94 | Nucleotide sequence encoding Full length heavy chain of MOR11873 with wild type IgG1 |
| 95 | Nucleotide sequence encoding Full length heavy chain of MOR11878 with wild type IgG1 |
| 96 | Nucleotide sequence encoding Full length heavy chain of MOR11879 with wild type IgG1 |
| 97 | Nucleotide sequence encoding Full length heavy chain of MOR11880 with wild type IgG1 |
| 98 | Cynomolgous IL12Rβ1 amino acid sequence |
| 99 | Human p40 subunit amino acid sequence |
| 100 | Human p35 subunit amino acid sequence |
| 101 | Human p19 subunit amino acid sequence |

TABLE 12

Useful amino acid and nucleotide sequences for practicing the invention

| SEQ ID NO: | Describes the amino acid or nucleotide sequence below: |
|---|---|
| 1 | SYGMS |
| 2 | GISYSGSDTEYADSVKG |
| 3 | SPDYIIDYGFDY |
| 4 | RASQGISSDLA |
| 5 | DASSLQS |
| 6 | QQYWIYPFT |
| 7 | SYGMS |
| 8 | GISYDASDTEYADSVKG |
| 9 | SPDYIIDYGFDY |
| 10 | RASQGISSDLA |
| 11 | DASSLQS |
| 12 | QQYWWYPFT |
| 13 | GYYMH |
| 14 | MIGPQHGEAIYAQKFQG |
| 15 | ESTDSDESPFDY |
| 16 | SGDNIRSYYVS |
| 17 | DDSDRPS |
| 18 | QSYGSHSNFVV |
| 19 | GYYMH |
| 20 | MIGPQHGEAIYAQKFQG |
| 21 | ESTDSDESPFDY |
| 22 | SGDNIRSYYVS |
| 23 | DDSDRPS |
| 24 | QSYGSHSNFVV |
| 25 | GFTFTSY |
| 26 | SYSGSD |
| 27 | SPDYIIDYGFDY |
| 28 | SQGISSD |
| 29 | DAS |
| 30 | YWIYPF |
| 31 | GFTFTSY |
| 32 | SYDASD |
| 33 | SPDYIIDYGFDY |
| 34 | SQGISSD |
| 35 | DAS |
| 36 | YWWYPF |
| 37 | GYTFTGY |
| 38 | GPQHGE |
| 39 | ESTDSDESPFDY |
| 40 | DNIRSYY |
| 41 | DDS |
| 42 | YGSHSNFV |
| 43 | GYTFTGY |
| 44 | GPQHGE |
| 45 | ESTDSDESPFDY |
| 46 | DNIRSYY |
| 47 | DDS |
| 48 | YGSHSNFV |
| 49 | QVQLVESGGGVVQPGRSLRLSCAASGFTFTSYGMSWVRQAPGKGLEWVAGISYSGSDTEYADSVKGRFTISRDNSKNTLYLQMNSLRAEDTAVYYCARSPDYIIDYGFDYWGRGTLVTVSS |
| 50 | AIQMTQSPSSLSASVGDRVTITCRASQGISSDLAWYQQKPGKAPKLLIYDASSLQSGVPSRFSGSGSGTDFTLTISSLQPEDFATYYCQQYWIYPFTFGQGTKVEIK |
| 51 | QVQLVESGGGVVQPGRSLRLSCAASGFTFTSYGMSWVRQAPGKGLEWVAGISYDASDTEYADSVKGRFTISRDNSKNTLYLQMNSLRAEDTAVYYCARSPDYIIDYGFDYWGRGTLVTVSS |
| 52 | AIQMTQSPSSLSASVGDRVTITCRASQGISSDLAWYQQKPGKAPKLLIYDASSLQSGVPSRFSGSGSGTDFTLTISSLQPEDFATYYCQQYWVVYPFTFGQGTKVEIK |
| 53 | QVQLVQSGAEVKKPGASVKVSCKASGYTFTGYYMHWVRQAPGQGLEWMGMIGPQHGEAIYAQKFQGRVTMTRDTSISTAYMELSRLRSEDTAVYYCARESTDSDESPFDYWGQGTLVTVSS |
| 54 | DIELTQPPSVSVSPGQTASITCSGDNIRSYYVSWYQQKPGQAPVLVIYDDSDRPSGIPERFSGSNSGNTATLTISGTQAEDEADYYCQSYGSHSNFVVFGGGTKLTVL |

TABLE 12-continued

Useful amino acid and nucleotide sequences for practicing the invention

| SEQ ID NO: | Describes the amino acid or nucleotide sequence below: |
|---|---|
| 55 | QVQLVQSGAEVKKPGASVKVSCKASGYTFTGYYMHWVRQAPGQGL<br>EWMGMIGPQHGEAIYAQKFQGRVTMTRDTSISTAYMELSRLRSDD<br>TAVYYCARESTDSDESPFDYWGQGTLVTVSS |
| 56 | SYELTQPLSVSVALGQTARITCSGDNIRSYYVSWYQQKPGQAPVL<br>VIYDDSDRPSGIPERFSGSNSGNTATLTISRAQAGDEADYYCQSY<br>GSHSNFVVFGGGTKLTVL |
| 57 | QVQLVESGGGVVQPGRSLRLSCAASGFTFTSYGMSWVRQAPGKGL<br>EWVAGISYSGSDTEYADSVKGRFTISRDNSKNTLYLQMNSLRAED<br>TAVYYCARSPDYIIDYGFDYWGRGTLVTVSSASTKGPSVFPLAPS<br>SKSTSGGTAALGCLVKDYFPEPVTVSWNSGALTSGVHTFPAVLQS<br>SGLYSLSSVVTVPSSSLGTQTYICNVNHKPSNTKVDKRVEPKSCD<br>KTHTCPPCPAPEAAGGPSVFLFPPKPKDTLMISRTPEVTCVVVDV<br>SHEDPEVKFNWYVDGVEVHNAKTKPREEQYNSTYRVVSVLTVLHQ<br>DWLNGKEYKCKVSNKALPAPIEKTISKAKGQPREPQVYTLPPSRE<br>EMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>K |
| 58 | QVQLVESGGGVVQPGRSLRLSCAASGFTFTSYGMSWVRQAPGKGL<br>EWVAGISYDASDTEYADSVKGRFTISRDNSKNTLYLQMNSLRAED<br>TAVYYCARSPDYIIDYGFDYWGRGTLVTVSSASTKGPSVFPLAPS<br>SKSTSGGTAALGCLVKDYFPEPVTVSWNSGALTSGVHTFPAVLQS<br>SGLYSLSSVVTVPSSSLGTQTYICNVNHKPSNTKVDKRVEPKSCD<br>KTHTCPPCPAPEAAGGPSVFLFPPKPKDTLMISRTPEVTCVVVDV<br>SHEDPEVKFNWYVDGVEVHNAKTKPREEQYNSTYRVVSVLTVLHQ<br>DWLNGKEYKCKVSNKALPAPIEKTISKAKGQPREPQVYTLPPSRE<br>EMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>K |
| 59 | QVQLVQSGAEVKKPGASVKVSCKASGYTFTGYYMHWVRQAPGQGL<br>EWMGMIGPQHGEAIYAQKFQGRVTMTRDTSISTAYMELSRLRSED<br>TAVYYCARESTDSDESPFDYWGQGTLVTVSSASTKGPSVFPLAPS<br>SKSTSGGTAALGCLVKDYFPEPVTVSWNSGALTSGVHTFPAVLQS<br>SGLYSLSSVVTVPSSSLGTQTYICNVNHKPSNTKVDKRVEPKSCD<br>KTHTCPPCPAPEAAGGPSVFLFPPKPKDTLMISRTPEVTCVVVDV<br>SHEDPEVKFNWYVDGVEVHNAKTKPREEQYNSTYRVVSVLTVLHQ<br>DWLNGKEYKCKVSNKALPAPIEKTISKAKGQPREPQVYTLPPSRE<br>EMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>K |
| 60 | QVQLVQSGAEVKKPGASVKVSCKASGYTFTGYYMHWVRQAPGQGL<br>EWMGMIGPQHGEAIYAQKFQGRVTMTRDTSISTAYMELSRLRSDD<br>TAVYYCARESTDSDESPFDYWGQGTLVTVSSASTKGPSVFPLAPS<br>SKSTSGGTAALGCLVKDYFPEPVTVSWNSGALTSGVHTFPAVLQS<br>SGLYSLSSVVTVPSSSLGTQTYICNVNHKPSNTKVDKRVEPKSCD<br>KTHTCPPCPAPEAAGGPSVFLFPPKPKDTLMISRTPEVTCVVVDV<br>SHEDPEVKFNWYVDGVEVHNAKTKPREEQYNSTYRVVSVLTVLHQ<br>DWLNGKEYKCKVSNKALPAPIEKTISKAKGQPREPQVYTLPPSRE<br>EMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>K |
| 61 | QVQLVESGGGVVQPGRSLRLSCAASGFTFTSYGMSWVRQAPGKGL<br>EWVAGISYSGSDTEYADSVKGRFTISRDNSKNTLYLQMNSLRAED<br>TAVYYCARSPDYIIDYGFDYWGRGTLVTVSSASTKGPSVFPLAPS<br>SKSTSGGTAALGCLVKDYFPEPVTVSWNSGALTSGVHTFPAVLQS<br>SGLYSLSSVVTVPSSSLGTQTYICNVNHKPSNTKVDKRVEPKSCD<br>KTHTCPPCPAPELLGGPSVFLFPPKPKDTLMISRTPEVTCVVVAV<br>SHEDPEVKFNWYVDGVEVHNAKTKPREEQYASTYRVVSVLTVLHQ<br>DWLNGKEYKCKVSNKALPAPIEKTISKAKGQPREPQVYTLPPSRE<br>EMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>K |
| 62 | QVQLVESGGGVVQPGRSLRLSCAASGFTFTSYGMSWVRQAPGKGL<br>EWVAGISYDASDTEYADSVKGRFTISRDNSKNTLYLQMNSLRAED<br>TAVYYCARSPDYIIDYGFDYWGRGTLVTVSSASTKGPSVFPLAPS<br>SKSTSGGTAALGCLVKDYFPEPVTVSWNSGALTSGVHTFPAVLQS<br>SGLYSLSSVVTVPSSSLGTQTYICNVNHKPSNTKVDKRVEPKSCD<br>KTHTCPPCPAPELLGGPSVFLFPPKPKDTLMISRTPEVTCVVVAV<br>SHEDPEVKFNWYVDGVEVHNAKTKPREEQYNSTYRVVSVLTVLHQ<br>DWLNGKEYKCKVSNKALPAPIEKTISKAKGQPREPQVYTLPPSRE<br>EMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>K |
| 63 | QVQLVQSGAEVKKPGASVKVSCKASGYTFTGYYMHWVRQAPGQGL<br>EWMGMIGPQHGEAIYAQKFQGRVTMTRDTSISTAYMELSRLRSED<br>TAVYYCARESTDSDESPFDYWGQGTLVTVSSASTKGPSVFPLAPS<br>SKSTSGGTAALGCLVKDYFPEPVTVSWNSGALTSGVHTFPAVLQS<br>SGLYSLSSVVTVPSSSLGTQTYICNVNHKPSNTKVDKRVEPKSCD<br>KTHTCPPCPAPELLGGPSVFLFPPKPKDTLMISRTPEVTCVVVAV<br>SHEDPEVKFNWYVDGVEVHNAKTKPREEQYNSTYRVVSVLTVLHQ<br>DWLNGKEYKCKVSNKALPAPIEKTISKAKGQPREPQVYTLPPSRE<br>EMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>K |
| 64 | QVQLVQSGAEVKKPGASVKVSCKASGYTFTGYYMHWVRQAPGQGL<br>EWMGMIGPQHGEAIYAQKFQGRVTMTRDTSISTAYMELSRLRSED<br>TAVYYCARESTDSDESPFDYWGQGTLVTVSSASTKGPSVFPLAPS<br>SKSTSGGTAALGCLVKDYFPEPVTVSWNSGALTSGVHTFPAVLQS<br>SGLYSLSSVVTVPSSSLGTQTYICNVNHKPSNTKVDKRVEPKSCD<br>KTHTCPPCPAPELLGGPSVFLFPPKPKDTLMISRTPEVTCVVVAV<br>SHEDPEVKFNWYVDGVEVHNAKTKPREEQYNSTYRVVSVLTVLHQ<br>DWLNGKEYKCKVSNKALPAPIEKTISKAKGQPREPQVYTLPPSRE<br>EMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>K |
| 65 | QVQLVESGGGVVQPGRSLRLSCAASGFTFTSYGMSWVRQAPGKGL<br>EWVAGISYSGSDTEYADSVKGRFTISRDNSKNTLYLQMNSLRAED<br>TAVYYCARSPDYIIDYGFDYWGRGTLVTVSSASTKGPSVFPLAPS<br>SKSTSGGTAALGCLVKDYFPEPVTVSWNSGALTSGVHTFPAVLQS<br>SGLYSLSSVVTVPSSSLGTQTYICNVNHKPSNTKVDKRVEPKSCD<br>KTHTCPPCPAPELLGGPSVFLFPPKPKDTLMISRTPEVTCVVVDV<br>SHEDPEVKFNWYVDGVEVHNAKTKPREEQYASTYRVVSVLTVLHQ<br>DWLNGKEYKCKVSNKALPAPIEKTISKAKGQPREPQVYTLPPSRE<br>EMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>K |
| 66 | QVQLVESGGGVVQPGRSLRLSCAASGFTFTSYGMSWVRQAPGKGL<br>EWVAGISYDASDTEYADSVKGRFTISRDNSKNTLYLQMNSLRAED<br>TAVYYCARSPDYIIDYGFDYWGRGTLVTVSSASTKGPSVFPLAPS<br>SKSTSGGTAALGCLVKDYFPEPVTVSWNSGALTSGVHTFPAVLQS<br>SGLYSLSSVVTVPSSSLGTQTYICNVNHKPSNTKVDKRVEPKSCD<br>KTHTCPPCPAPELLGGPSVFLFPPKPKDTLMISRTPEVTCVVVDV<br>SHEDPEVKFNWYVDGVEVHNAKTKPREEQYASTYRVVSVLTVLHQ<br>DWLNGKEYKCKVSNKALPAPIEKTISKAKGQPREPQVYTLPPSRE<br>EMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>K |
| 67 | QVQLVQSGAEVKKPGASVKVSCKASGYTFTGYYMHWVRQAPGQGL<br>EWMGMIGPQHGEAIYAQKFQGRVTMTRDTSISTAYMELSRLRSED<br>TAVYYCARESTDSDESPFDYWGQGTLVTVSSASTKGPSVFPLAPS<br>SKSTSGGTAALGCLVKDYFPEPVTVSWNSGALTSGVHTFPAVLQS<br>SGLYSLSSVVTVPSSSLGTQTYICNVNHKPSNTKVDKRVEPKSCD<br>KTHTCPPCPAPELLGGPSVFLFPPKPKDTLMISRTPEVTCVVVDV<br>SHEDPEVKFNWYVDGVEVHNAKTKPREEQYASTYRVVSVLTVLHQ<br>DWLNGKEYKCKVSNKALPAPIEKTISKAKGQPREPQVYTLPPSRE<br>EMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>K |
| 68 | QVQLVQSGAEVKKPGASVKVSCKASGYTFTGYYMHWVRQAPGQGL<br>EWMGMIGPQHGEAIYAQKFQGRVTMTRDTSISTAYMELSRLRSDD<br>TAVYYCARESTDSDESPFDYWGQGTLVTVSSASTKGPSVFPLAPS<br>SKSTSGGTAALGCLVKDYFPEPVTVSWNSGALTSGVHTFPAVLQS<br>SGLYSLSSVVTVPSSSLGTQTYICNVNHKPSNTKVDKRVEPKSCD |

TABLE 12-continued

Useful amino acid and nucleotide sequences for practicing the invention

| SEQ ID NO: | Describes the amino acid or nucleotide sequence below: |
|---|---|
|  | KTHTCPPCPAPELLGGPSVFLFPPKPKDTLMISRTPEVTCVVVDV SHEDPEVKFNWYVDGVEVHNAKTKPREEQYASTYRVVSVLTVLHQ DWLNGKEYKCKVSNKALPAPIEKTISKAKGQPREPQVYTLPPSRE EMTKNQVSLTCLVKGFYPSDIAVEWESNGQPENNYKTTPPVLDSD GSFFLYSKLTVDKSRWQQGNVFSCSVMHEALHNHYTQKSLSLSPG K |
| 69 | AIQMTQSPSSLSASVGDRVTITCRASQGISSDLAWYQQKPGKAPK LLIYDASSLQSGVPSRFSGSGSGTDFTLTISSLQPEDFATYYCQQ YWIYPFTFGQGTKVEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSFNRGEC |
| 70 | AIQMTQSPSSLSASVGDRVTITCRASQGISSDLAWYQQKPGKAPK LLIYDASSLQSGVPSRFSGSGSGTDFTLTISSLQPEDFATYYCQQ YWWYPFTFGQGTKVEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSFNRGEC |
| 71 | DIELTQPPSVSVSPGQTASITCSGDNIRSYYVSWYQQKPGQAPVL VIYDDSDRPSGIPERFSGSNSGNTATLTISGTQAEDEADYYCQSY GSHSNFVVFGGGTKLTVLGQPKAAPSVTLFPPSSEELQANKATLV CLISDFYPGAVTVAWKADSSPVKAGVETTTPSKQSNNKYAASSYL SLTPEQWKSHRSYSCQVTHEGSTVEKTVAPTECS |
| 72 | SYELTQPLSVSVALGQTARITCSGDNIRSYYVSWYQQKPGQAPVL VIYDDSDRPSGIPERFSGSNSGNTATLTISRAQAGDEADYYCQSY GSHSNFVVFGGGTKLTVLGQPKAAPSVTLFPPSSEELQANKATLV CLISDFYPGAVTVAWKADSSPVKAGVETTTPSKQSNNKYAASSYL SLTPEQWKSHRSYSCQVTHEGSTVEKTVAPTECS |
| 73 | caggtgcaattggtggaaagcggcggaggcgtggtgcagcctgg agaagcctgagactgagctgtgccgccagcggcttcaccttcacc agctacgcatgagctgggtccgacaggcccctggcaagggcctg gaatgggtggccggcatcagctacgacgccagcgacaccgagtac gccgacagcgtgaagggccggttcaccatcagccgggacaacagc aagaacaccctgtacctgcagatgaacagcctgcgggccgaggac accgccgtgtactactgcgccagaagccccgactacatcatcgac tacggcttcgactactggggccagggcaccctggtcaccgtcagc tcagcctccaccaagggtccatcggtcttccccctggcaccctcc tccaagagcacctctgggggcacagcggccctgggctgcctggtc aaggactacttccccgaaccggtgacggtgtcgtggaactcaggc gccctgaccagcggcgtgcacaccttcccggctgtcctacagtcc tcaggactctactccctcagcagcgtggtgaccgtgccctccagc agcttgggcacccagacctacatctgcaacgtgaatcacaagccc agcaacaccaaggtggacaagagagttgagcccaaatcttgtgac aaaactcacacatgcccaccgtgcccagcacctgaagcagcgggg ggaccgtcagtcttcctcttccccccaaaacccaaggacaccctc atgatctcccggacccctgaggtcacatgcgtggtggtggacgtg agccacgaagaccctgaggtcaagttcaactggtacgtggacggc gtggaggtgcataatgccaagacaaagccgcgggaggagcagtac aacagcacgtaccgggtggtcagcgtcctcaccgtcctgcaccag gactggctgaatggcaaggagtacaagtgcaaggtctccaacaaa gccctcccagcccccatcgagaaaaccatctccaaagccaaaggg cagccccgagaaccacaggtgtacaccctgcccccatcccgggag gagatgaccaagaaccaggtcagcctgacctgcctggtcaaaggc ttctatcccagcgacatcgccgtggagtgggagagcaatgggcag ccggagaacaactacaagaccacgcctcccgtgctggactccgac ggctccttcttcctctacagcaagctcaccgtggacaagagcagg tggcagcaggggaacgtcttctcatgctccgtgatgcatgaggct ctgcacaaccactacacgcagaagagcctctccctgtctccgggt aaa |
| 74 | caggtgcaattggtggaaagcggcggaggcgtggtgcagcctgg agaagcctgagactgagctgtgccgccagcggcttcaccttcacc agctacgcatgagctgggtccgacaggcccctggcaagggcctg gaatgggtggccggcatcagctacgacgccagcgacaccgagtac gccgacagcgtgaagggccggttcaccatcagccgggacaacagc aagaacaccctgtacctgcagatgaacagcctgcgggccgaggac accgccgtgtactactgcgccagaagccccgactacatcatcgac tacggcttcgactactggggccagggcaccctggtcaccgtcagc tcagcctccaccaagggtccatcggtcttccccctggcaccctcc tccaagagcacctctgggggcacagcggccctgggctgcctggtc aaggactacttccccgaaccggtgacggtgtcgtggaactcaggc gccctgaccagcggcgtgcacaccttcccggctgtcctacagtcc tcaggactctactccctcagcagcgtggtgaccgtgccctccagc agcttgggcacccagacctacatctgcaacgtgaatcacaagccc agcaacaccaaggtggacaagagagttgagcccaaatcttgtgac aaaactcacacatgcccaccgtgcccagcacctgaagcagcgggg ggaccgtcagtcttcctcttccccccaaaacccaaggacaccctc atgatctcccggacccctgaggtcacatgcgtggtggtggacgtg agccacgaagaccctgaggtcaagttcaactggtacgtggacggc gtggaggtgcataatgccaagacaaagccgcgggaggagcagtac aacagcacgtaccgggtggtcagcgtcctcaccgtcctgcaccag gactggctgaatggcaaggagtacaagtgcaaggtctccaacaaa gccctcccagcccccatcgagaaaaccatctccaaagccaaaggg cagccccgagaaccacaggtgtacaccctgcccccatcccgggag gagatgaccaagaaccaggtcagcctgacctgcctggtcaaaggc ttctatcccagcgacatcgccgtggagtgggagagcaatgggcag ccggagaacaactacaagaccacgcctcccgtgctggactccgac ggctccttcttcctctacagcaagctcaccgtggacaagagcagg tggcagcaggggaacgtcttctcatgctccgtgatgcatgaggct ctgcacaaccactacacgcagaagagcctctccctgtctccgggt aaa |
| 75 | caggtgcaattggtgcagtctggcgccgaagtgaagaaacctggg gctagtgtgaaggtgtcctgcaaggccagcggctacaccttcacc ggctactacatgcactgggtccgacaggcccctggacagggcctg aatggatgggcatgatcggcccccagcacggcgaggccatctac gcccagaaattccagggcagagtgaccatgacccgggacaccagc atcagcaccgcctacatggaactgagccggctgcggagcgaggac accgccgtgtactactgcgccagagagagcaccgacagcgacgag agccccttcgactactggggccagggcaccctggtcaccgtcagc tcagcctccaccaagggtccatcggtcttccccctggcaccctcc tccaagagcacctctgggggcacagcggccctgggctgcctggtc aaggactacttccccgaaccggtgacggtgtcgtggaactcaggc gccctgaccagcggcgtgcacaccttcccggctgtcctacagtcc tcaggactctactccctcagcagcgtggtgaccgtgccctccagc agcttgggcacccagacctacatctgcaacgtgaatcacaagccc agcaacaccaaggtggacaagagagttgagcccaaatcttgtgac aaaactcacacatgcccaccgtgcccagcacctgaagcagcgggg ggaccgtcagtcttcctcttccccccaaaacccaaggacaccctc atgatctcccggacccctgaggtcacatgcgtggtggtggacgtg agccacgaagaccctgaggtcaagttcaactggtacgtggacggc gtggaggtgcataatgccaagacaaagccgcgggaggagcagtac aacagcacgtaccgggtggtcagcgtcctcaccgtcctgcaccag gactggctgaatggcaaggagtacaagtgcaaggtctccaacaaa gccctcccagcccccatcgagaaaaccatctccaaagccaaaggg cagccccgagaaccacaggtgtacaccctgcccccatcccgggag gagatgaccaagaaccaggtcagcctgacctgcctggtcaaaggc ttctatcccagcgacatcgccgtggagtgggagagcaatgggcag ccggagaacaactacaagaccacgcctcccgtgctggactccgac ggctccttcttcctctacagcaagctcaccgtggacaagagcagg tggcagcaggggaacgtcttctcatgctccgtgatgcatgaggct ctgcacaaccactacacgcagaagagcctctccctgtctccgggt aaa |
| 76 | caggtgcaattggtgcagtctggcgccgaagtgaagaaacctggg gccagcgtgaaggtgtcctgcaaggccagcggctacaccttcacc ggctactacatgcactgggtccgacaggcccctggacagggcctg aatggatgggcatgatcggcccccagcacggcgaggccatctac gcccagaaattccagggcagagtgaccatgacccgggacaccagc atcagcaccgcctacatggaactgagccggctgcggagcgaggac accgccgtgtactactgcgccagagagagcaccgacagcgacgag agccccttcgactactggggccagggcaccctggtcaccgtcagc tcagcctccaccaagggtccatcggtcttccccctggcaccctcc tccaagagcacctctgggggcacagcggccctgggctgcctggtc aaggactacttccccgaaccggtgacggtgtcgtggaactcaggc gccctgaccagcggcgtgcacaccttcccggctgtcctacagtcc tcaggactctactccctcagcagcgtggtgaccgtgccctccagc agcttgggcacccagacctacatctgcaacgtgaatcacaagccc agcaacaccaaggtggacaagagagttgagcccaaatcttgtgac aaaactcacacatgcccaccgtgcccagcacctgaagcagcgggg ggaccgtcagtcttcctcttccccccaaaacccaaggacaccctc atgatctcccggacccctgaggtcacatgcgtggtggtggacgtg agccacgaagaccctgaggtcaagttcaactggtacgtggacggc |

TABLE 12-continued

Useful amino acid and nucleotide sequences for practicing the invention

| SEQ ID NO: | Describes the amino acid or nucleotide sequence below: |
|---|---|
|  | gtggaggtgcataatgccaagacaaagccgcgggaggagcagtac<br>aacagcacgtacccgggtggtcagcgtcctcaccgtcctgcaccag<br>gactggctgaatggcaaggagtacaagtgcaaggtctccaacaaa<br>gccctcccagccccatcgagaaaaccatctccaaagccaaaggg<br>cagccccgagaaccacaggtgtacaccctgcccccatcccgggag<br>gagatgaccaagaaccaggtcagcctgacctgcctggtcaaaggc<br>ttctatcccagcgacatcgccgtggagtgggagagcaatgggcag<br>ccggagaacaactacaagaccacgcctcccgtgctggactccgac<br>ggctccttcttcctctacagcaagctcaccgtggacaagagcagg<br>tggcagcaggggaacgtcttctcatgctccgtgatgcatgaggct<br>ctgcacaaccactacacgcagaagagcctctccctgtctccgggt<br>aaa |
| 77 | caggtgcaattggtggaaagcggcggaggcgtggtgcagcctggc<br>agaagcctgagactgagctgtgccgccagcggcttcaccttcacc<br>agctacggcatgagctgggtccgacaggcccctggcaagggcctg<br>gaatgggtggccggcatcagctacagcggcagcgacaccgagtac<br>gccgacagcgtgaagggccggttcaccatcagccgggacaacagc<br>aagaacaccctgtacctgcagatgaacagcctgcgggccgaggac<br>accgccgtgtactactgcgccagaagccccgactacatcatcgac<br>tacggcttcgactactggggcagaggcaccctggtcaccgtcagc<br>tcagcctccaccaagggtccatcggtcttccccctggcaccctcc<br>tccaagagcacctctgggggcacagcggccctgggctgcctggtc<br>aaggactacttccccgaaccggtgacggtgtcgtggaactcaggc<br>gccctgaccagcggcgtgcacaccttcccggctgtcctacagtcc<br>tcaggactctactcccctcagcagcgtggtgaccgtgccctccagc<br>agcttgggcacccagacctacatctgcaacgtgaatcacaagccc<br>agcaacaccaaggtggacaagagagttgagcccaaatcttgtgac<br>aaaactcacacatgcccaccgtgcccagcacctgaactcctgggg<br>ggaccgtcagtcttcctcttccccccaaaacccaaggacaccctc<br>atgatctcccggacccctgaggtcacatgcgtggtggtggacgtg<br>agccacgaagaccctgaggtcaagttcaactggtacgtggacggc<br>gtggaggtgcataatgccaagacaaagccgcgggaggagcagtac<br>aacagcacgtacccgggtggtcagcgtcctcaccgtcctgcaccag<br>gactggctgaatggcaaggagtacaagtgcaaggtctccaacaaa<br>gccctcccagccccatcgagaaaaccatctccaaagccaaaggg<br>cagccccgagaaccacaggtgtacaccctgcccccatcccgggag<br>gagatgaccaagaaccaggtcagcctgacctgcctggtcaaaggc<br>ttctatcccagcgacatcgccgtggagtgggagagcaatgggcag<br>ccggagaacaactacaagaccacgcctcccgtgctggactccgac<br>ggctccttcttcctctacagcaagctcaccgtggacaagagcagg<br>tggcagcaggggaacgtcttctcatgctccgtgatgcatgaggct<br>ctgcacaaccactacacgcagaagagcctctccctgtctccgggt<br>aaa |
| 78 | caggtgcaattggtggaaagcggcggaggcgtggtgcagcctggc<br>agaagcctgagactgagctgtgccgccagcggcttcaccttcacc<br>agctacggcatgagctgggtccgacaggcccctggcaagggcctg<br>gaatgggtggccggcatcagctacgacgccagcgacaccgagtac<br>gccgacagcgtgaagggccggttcaccatcagccgggacaacagc<br>aagaacaccctgtacctgcagatgaacagcctgcgggccgaggac<br>accgccgtgtactactgcgccagaagccccgactacatcatcgac<br>tacggcttcgactactggggcagaggcaccctggtcaccgtcagc<br>tcagcctccaccaagggtccatcggtcttccccctggcaccctcc<br>tccaagagcacctctgggggcacagcggccctgggctgcctggtc<br>aaggactacttccccgaaccggtgacggtgtcgtggaactcaggc<br>gccctgaccagcggcgtgcacaccttcccggctgtcctacagtcc<br>tcaggactctactcccctcagcagcgtggtgaccgtgccctccagc<br>agcttgggcacccagacctacatctgcaacgtgaatcacaagccc<br>agcaacaccaaggtggacaagagagttgagcccaaatcttgtgac<br>aaaactcacacatgcccaccgtgcccagcacctgaactcctgggg<br>ggaccgtcagtcttcctcttccccccaaaacccaaggacaccctc<br>atgatctcccggacccctgaggtcacatgcgtggtggtggacgtg<br>agccacgaagaccctgaggtcaagttcaactggtacgtggacggc<br>gtggaggtgcataatgccaagacaaagccgcgggaggagcagtac<br>aacagcacgtacccgggtggtcagcgtcctcaccgtcctgcaccag<br>gactggctgaatggcaaggagtacaagtgcaaggtctccaacaaa<br>gccctcccagccccatcgagaaaaccatctccaaagccaaaggg<br>cagccccgagaaccacaggtgtacaccctgcccccatcccgggag<br>gagatgaccaagaaccaggtcagcctgacctgcctggtcaaaggc<br>ttctatcccagcgacatcgccgtggagtgggagagcaatgggcag<br>ccggagaacaactacaagaccacgcctcccgtgctggactccgac<br>ggctccttcttcctctacagcaagctcaccgtggacaagagcagg<br>tggcagcaggggaacgtcttctcatgctccgtgatgcatgaggct<br>ctgcacaaccactacacgcagaagagcctctccctgtctccgggt<br>aaa |
| 79 | caggtgcaattggtgcagtctggcgccgaagtgaagaaacctggg<br>gctagtgtgaaggtgtcctgcaaggccagcggctacaccttcacc<br>ggctactacatgcactgggtccgacaggcccctggacagggcctg<br>gaatggatgggcatgatcggccccagcacggcgaggccatctac<br>gcccagaaattccagggcagagtgaccatgacccgggacaccagc<br>atcagcaccgcctacatggaactgagccggctgcggagcgaggac<br>accgccgtgtactactgcgccagagagagcaccgacagcgacgag<br>agccccttcgactactgggggcagggcaccctggtcaccgtcagc<br>tcagcctccaccaagggtccatcggtcttccccctggcaccctcc<br>tccaagagcacctctgggggcacagcggccctgggctgcctggtc<br>aaggactacttccccgaaccggtgacggtgtcgtggaactcaggc<br>gccctgaccagcggcgtgcacaccttcccggctgtcctacagtcc<br>tcaggactctactcccctcagcagcgtggtgaccgtgccctccagc<br>agcttgggcacccagacctacatctgcaacgtgaatcacaagccc<br>agcaacaccaaggtggacaagagagttgagcccaaatcttgtgac<br>aaaactcacacatgcccaccgtgcccagcacctgaactcctgggg<br>ggaccgtcagtcttcctcttccccccaaaacccaaggacaccctc<br>atgatctcccggacccctgaggtcacatgcgtggtggtggccgtg<br>agccacgaagaccctgaggtcaagttcaactggtacgtggacggc<br>gtggaggtgcataatgccaagacaaagccgcgggaggagcagtac<br>aacagcacgtacccgggtggtcagcgtcctcaccgtcctgcaccag<br>gactggctgaatggcaaggagtacaagtgcaaggtctccaacaaa<br>gccctcccagccccatcgagaaaaccatctccaaagccaaaggg<br>cagccccgagaaccacaggtgtacaccctgcccccatcccgggag<br>gagatgaccaagaaccaggtcagcctgacctgcctggtcaaaggc<br>ttctatcccagcgacatcgccgtggagtgggagagcaatgggcag<br>ccggagaacaactacaagaccacgcctcccgtgctggactccgac<br>ggctccttcttcctctacagcaagctcaccgtggacaagagcagg<br>tggcagcaggggaacgtcttctcatgctccgtgatgcatgaggct<br>ctgcacaaccactacacgcagaagagcctctccctgtctccgggt<br>aaa |
| 80 | caggtgcaattggtgcagtctggcgccgaagtgaagaaacctggg<br>gccagcgtgaaggtgtcctgcaaggccagcggctacaccttcacc<br>ggctactacatgcactgggtccgacaggcccctggacagggcctg<br>gaatggatgggcatgatcggccccagcacggcgaggccatctac<br>gcccagaaattccagggcagagtgaccatgacccgggacaccagc<br>atcagcaccgcctacatggaactgagccggctgcggagcgacgac<br>accgccgtgtactactgcgccagagagagcaccgacagcgacgag<br>agccccttcgactactgggggcagggcaccctggtcaccgtcagc<br>tcagcctccaccaagggtccatcggtcttccccctggcaccctcc<br>tccaagagcacctctgggggcacagcggccctgggctgcctggtc<br>aaggactacttccccgaaccggtgacggtgtcgtggaactcaggc<br>gccctgaccagcggcgtgcacaccttcccggctgtcctacagtcc<br>tcaggactctactcccctcagcagcgtggtgaccgtgccctccagc<br>agcttgggcacccagacctacatctgcaacgtgaatcacaagccc<br>agcaacaccaaggtggacaagagagttgagcccaaatcttgtgac<br>aaaactcacacatgcccaccgtgcccagcacctgaactcctgggg<br>ggaccgtcagtcttcctcttccccccaaaacccaaggacaccctc<br>atgatctcccggacccctgaggtcacatgcgtggtggtggccgtg<br>agccacgaagaccctgaggtcaagttcaactggtacgtggacggc<br>gtggaggtgcataatgccaagacaaagccgcgggaggagcagtac<br>aacagcacgtacccgggtggtcagcgtcctcaccgtcctgcaccag<br>gactggctgaatggcaaggagtacaagtgcaaggtctccaacaaa<br>gccctcccagccccatcgagaaaaccatctccaaagccaaaggg<br>cagccccgagaaccacaggtgtacaccctgcccccatcccgggag<br>gagatgaccaagaaccaggtcagcctgacctgcctggtcaaaggc<br>ttctatcccagcgacatcgccgtggagtgggagagcaatgggcag<br>ccggagaacaactacaagaccacgcctcccgtgctggactccgac<br>ggctccttcttcctctacagcaagctcaccgtggacaagagcagg<br>tggcagcaggggaacgtcttctcatgctccgtgatgcatgaggct<br>ctgcacaaccactacacgcagaagagcctctccctgtctccgggt<br>aaa |
| 81 | caggtgcaattggtggaaagcggcggaggcgtggtgcagcctggc<br>agaagcctgagactgagctgtgccgccagcggcttcaccttcacc<br>agctacggcatgagctgggtccgacaggcccctggcaagggcctg<br>gaatgggtggccggcatcagctacagcggcagcgacaccgagtac<br>gccgacagcgtgaagggccggttcaccatcagccgggacaacagc |

TABLE 12-continued

Useful amino acid and nucleotide sequences for practicing the invention

| SEQ ID NO: | Describes the amino acid or nucleotide sequence below: |
|---|---|
|  | aagaacaccctgtacctgcagatgaacagcctgcgggccgaggac accgccgtgtactactgcgccagaagccccgactacatcatcgac tacggcttcgactactggggcagaggcaccctggtcaccgtcagc tcagcctccaccaaggggtccatcggtcttcccctggcaccctcc tccaagagcacctctgggggcacagcggccctgggctgcctggtc aaggactacttccccgaaccggtgacggtgtcgtggaactcaggc gccctgaccagcggcgtgcacaccttcccggctgtcctacagtcc tcaggactctactccctcagcagcgtggtgaccgtgccctccagc agcttgggcacccagacctacatctgcaacgtgaatcacaagccc agcaacaccaaggtggacaagagagttgagcccaaatcttgtgac aaaactcacacatgcccaccgtgcccagcacctgaactcctgggg ggaccgtcagtcttcctcttccccccaaaacccaaggacaccctc atgatctcccggacccctgaggtcacatgcgtggtggtggacgtg agccacgaagaccctgaggtcaagttcaactggtacgtggacggc gtggaggtgcataatgccaagacaaagccgcgggaggagcagtac gccagcacgtaccgggtggtcagcgtcctcaccgtcctgcaccag gactggctgaatggcaaggagtacaagtgcaaggtctccaacaaa gccctcccagcccccatcgagaaaaccatctccaaagccaaaggg cagccccgagaaccacaggtgtacaccctgcccccatcccgggag gagatgaccaagaaccaggtcagcctgacctgcctggtcaaaggc ttctatcccagcgacatcgccgtggagtgggagagcaatgggcag ccggagaacaactacaagaccacgcctcccgtgctggactccgac ggctccttcttcctctacagcaagctcaccgtggacaagagcagg tggcagcaggggaacgtcttctcatgctccgtgatgcatgaggct ctgcacaaccactacacgcagaagagcctctccctgtctccgggt aaa |
| 82 | caggtgcaattggtggaaagcggcggaggcgtggtgcagcctggc agaagcctgagactgagctgtgccgccagcggcttcaccttcacc agctacgcatgagctgggtccgacaggcccctggcaagggcctg gaatgggtggccgtcatcagctacgacggcagcgacaccgagtac gccgacagcgtgaagggccggttcaccatcagccgggacaacagc aagaacaccctgtacctgcagatgaacagcctgcgggccgaggac accgccgtgtactactgcgccagaagccccgactacatcatcgac tacggcttcgactactggggcagaggcaccctggtcaccgtcagc tcagcctccaccaaggggtccatcggtcttcccctggcaccctcc tccaagagcacctctgggggcacagcggccctgggctgcctggtc aaggactacttccccgaaccggtgacggtgtcgtggaactcaggc gccctgaccagcggcgtgcacaccttcccggctgtcctacagtcc tcaggactctactccctcagcagcgtggtgaccgtgccctccagc agcttgggcacccagacctacatctgcaacgtgaatcacaagccc agcaacaccaaggtggacaagagagttgagcccaaatcttgtgac aaaactcacacatgcccaccgtgcccagcacctgaactcctgggg ggaccgtcagtcttcctcttccccccaaaacccaaggacaccctc atgatctcccggacccctgaggtcacatgcgtggtggtggacgtg agccacgaagaccctgaggtcaagttcaactggtacgtggacggc gtggaggtgcataatgccaagacaaagccgcgggaggagcagtac gccagcacgtaccgggtggtcagcgtcctcaccgtcctgcaccag gactggctgaatggcaaggagtacaagtgcaaggtctccaacaaa gccctcccagcccccatcgagaaaaccatctccaaagccaaaggg cagccccgagaaccacaggtgtacaccctgcccccatcccgggag gagatgaccaagaaccaggtcagcctgacctgcctggtcaaaggc ttctatcccagcgacatcgccgtggagtgggagagcaatgggcag ccggagaacaactacaagaccacgcctcccgtgctggactccgac ggctccttcttcctctacagcaagctcaccgtggacaagagcagg tggcagcaggggaacgtcttctcatgctccgtgatgcatgaggct ctgcacaaccactacacgcagaagagcctctccctgtctccgggt aaa |
| 83 | caggtgcaattggtgcagtctggcgccgaagtgaagaaacctggg gctagtgtgaaggtgtcctgcaaggccagcggctacaccttcacc ggctactacatgcactgggtccgacaggcccctggacagggcctg gaatggatgggcatgatcggccccagcacggccgaggccatctac gcccagaaattccagggcagagtgaccatgaccacggacacccagac atcagcaccgcctacatggaactgagccggctgcggagcgaggac accgccgtgtactactgcgccagagagagcaccgacagcgacgag agccccttcgactactggggcagggcaccctggtcaccgtcagc tcagcctccaccaaggggtccatcggtcttcccctggcaccctcc tccaagagcacctctgggggcacagcggccctgggctgcctggtc aaggactacttccccgaaccggtgacggtgtcgtggaactcaggc gccctgaccagcggcgtgcacaccttcccggctgtcctacagtcc tcaggactctactccctcagcagcgtggtgaccgtgccctccagc agcttgggcacccagacctacatctgcaacgtgaatcacaagccc agcaacaccaaggtggacaagagagttgagcccaaatcttgtgac aaaactcacacatgcccaccgtgcccagcacctgaactcctgggg ggaccgtcagtcttcctcttccccccaaaacccaaggacaccctc atgatctcccggacccctgaggtcacatgcgtggtggtggacgtg agccacgaagaccctgaggtcaagttcaactggtacgtggacggc gtggaggtgcataatgccaagacaaagccgcgggaggagcagtac gccagcacgtaccgggtggtcagcgtcctcaccgtcctgcaccag gactggctgaatggcaaggagtacaagtgcaaggtctccaacaaa gccctcccagcccccatcgagaaaaccatctccaaagccaaaggg cagccccgagaaccacaggtgtacaccctgcccccatcccgggag gagatgaccaagaaccaggtcagcctgacctgcctggtcaaaggc ttctatcccagcgacatcgccgtggagtgggagagcaatgggcag ccggagaacaactacaagaccacgcctcccgtgctggactccgac ggctccttcttcctctacagcaagctcaccgtggacaagagcagg tggcagcaggggaacgtcttctcatgctccgtgatgcatgaggct ctgcacaaccactacacgcagaagagcctctccctgtctccgggt aaa |
| 84 | caggtgcaattggtgcagtctggcgccgaagtgaagaaacctggg gccagcgtgaaggtgtcctgcaaggccagcggctacaccttcacc ggctactacatgcactgggtccgacaggcccctggacagggcctg gaatggatgggcatgatcggccccagcacggccgaggccatctac gcccagaaattccagggcagagtgaccatgaccgccgggacacccagac atcagcaccgcctacatggaactgagccggctgcggagcgaggac accgccgtgtactactgcgccagagagagcaccgacagcgacgag agccccttcgactactggggcagggcaccctggtcaccgtcagc tcagcctccaccaaggggtccatcggtcttcccctggcaccctcc tccaagagcacctctgggggcacagcggccctgggctgcctggtc aaggactacttccccgaaccggtgacggtgtcgtggaactcaggc gccctgaccagcggcgtgcacaccttcccggctgtcctacagtcc tcaggactctactccctcagcagcgtggtgaccgtgccctccagc agcttgggcacccagacctacatctgcaacgtgaatcacaagccc agcaacaccaaggtggacaagagagttgagcccaaatcttgtgac aaaactcacacatgcccaccgtgcccagcacctgaactcctgggg ggaccgtcagtcttcctcttccccccaaaacccaaggacaccctc atgatctcccggacccctgaggtcacatgcgtggtggtggacgtg agccacgaagaccctgaggtcaagttcaactggtacgtggacggc gtggaggtgcataatgccaagacaaagccgcgggaggagcagtac gccagcacgtaccgggtggtcagcgtcctcaccgtcctgcaccag gactggctgaatggcaaggagtacaagtgcaaggtctccaacaaa gccctcccagcccccatcgagaaaaccatctccaaagccaaaggg cagccccgagaaccacaggtgtacaccctgcccccatcccgggag gagatgaccaagaaccaggtcagcctgacctgcctggtcaaaggc ttctatcccagcgacatcgccgtggagtgggagagcaatgggcag ccggagaacaactacaagaccacgcctcccgtgctggactccgac ggctccttcttcctctacagcaagctcaccgtggacaagagcagg tggcagcaggggaacgtcttctcatgctccgtgatgcatgaggct ctgcacaaccactacacgcagaagagcctctccctgtctccgggt aaa |
| 85 | gccatccagatgacccagagccccagcagcctgagcgccagcgtg ggcgacagagtgaccatcacctgtcgggccagccagggcatcagc agcgacctggcctggtatcagcagaagcccggcaaggccccaag ctgctgatctacgacgccagctccctgcagagcggcgtgcccagc agatttttccggcagcggctccggcaccgacttcacctgtgaccatc agcagcctgcagcccgaggacttcgccacctactactgccagcag tactggtgatcaccccttcaccttcggccagggcaccaaggtggaa atcaagcgtacggtggccgctcccagcgtgttcatcttccccccc agcgacgagcagctgaagagcggcaccgccagcgtggtgtgcctg ctgaacaacttctaccccogggaggccaaggtgcagtggaaggtg gacaacgccctgcagagcggcaacagccaggaaagcgtcaccgag caggacagcaaggactccacctacagcctgagcagcaccctgacc ctgagcaaggccgactacgagaagcacaaggtgtacgcctgcgag gtgacccaccagggcctgtccagccccgtgaccaagagcttcaac cggggcgagtgt |
| 86 | gccatccagatgacccagagccccagcagcctgagcgccagcgtg ggcgacagagtgaccatcacctgtcgggccagccagggcatcagc agcgacctggcctggtatcagcagaagcccggcaaggccccaag ctgctgatctacgacgccagctccctgcagagcggcgtgcccagc agatttttccggcagcggctccggcaccgacttcacccctgaccatc agcagcctgcagcccgaggacttcgccacttactactgccagcag tactggtggtatcccttcaccttcggccagggcaccaaggtggaa |

TABLE 12-continued

Useful amino acid and nucleotide sequences for practicing the invention

| SEQ ID NO: | Describes the amino acid or nucleotide sequence below: |
|---|---|
|  | atcaagcgtacggtggccgctcccagcgtgttcatcttcccccca<br>agcgacgagcagctgaagagcggcaccgccagcgtggtgtgcctg<br>ctgaacaacttctaccccgggaggcaagtgcagtggaaggtg<br>gacaacgccctgcagagcggcaacagccaggaaagcgtcaccgag<br>caggacagcaaggactccacctacagcctgagcagcaccctgacc<br>ctgagcaaggccgactacgaaagcacaaggtgtacgcctgcgag<br>gtgacccaccaggcctgtccagcccgtgaccaagagcttcaac<br>cggggcgagtgt |
| 87 | gacatcgagctgacccagcccctagcgtgtccgtgtctcctggc<br>cagaccgccagcatcacctgtagcggcgacaacatcagatcctac<br>tacgtgtcctggtatcagcagaagcccggccaggcccccgtgctg<br>gtcatctacgacgacagcgaccggccagcggcatccccgagaga<br>ttcagcggcagcaacagcggcaacaccgccaccctgaccatcagc<br>ggcacccaggccgaggacgaggccgactactactgccagagctac<br>ggcagccacagcaacttcgtggtgttcggcggaggcaccaagtta<br>accgtcctaggtcagcccaaggctgcccctcggtcactctgttc<br>ccgccctcctctgaggagcttcaagccaacaaggccacactggtg<br>tgtctcataagtgacttctacccgggagccgtgacagtggcctgg<br>aaggcagatagcccccgtcaaggcgggagtggagaccaccaca<br>ccctccaaacaaagcaacaacaagtacgcggccagcagctatctg<br>agcctgacgcctgagcagtggaagtcccacagaagctacgctgc<br>caggtcacgcatgaagggagcaccgtggagaagacagtggcccct<br>acagaatgttca |
| 88 | tcttacgagctgactcagccctgtccgtgtctgtggctctgggc<br>cagaccgcccgatcacatgcagcggcgacaacatcagatcctac<br>tacgtgtcctggtatcagcagaagcctggacaggcccccgtgctg<br>gtcatctacgacgacagcgaccggccagcggcatccccgagaga<br>ttcagcggaagcaacagcggcaacaccgccaccctgaccatctcc<br>agagcccaggccgggcgacgaggccgactactactgccagagctac<br>ggcagccacagcaacttcgtggtgttcggcggaggcaccaagtta<br>accgtcctaggtcagcccaaggctgcccctcggtcactctgttc<br>ccgccctcctctgaggagcttcaagccaacaaggccacactggtg<br>tgtctcataagtgacttctacccgggagccgtgacagtggcctgg<br>aaggcagatagcccccgtcaaggcgggagtggagaccaccaca<br>ccctccaaacaaagcaacaacaagtacgcggccagcagctatctg<br>agcctgacgcctgagcagtggaagtcccacagaagctacagctgc<br>caggtcacgcatgaagggagcaccgtggagaagacagtggcccct<br>acagaatgttca |
| 89 | MEPLVTWVVPLLFLFLLSRQGAACRTSECCFQDPPYPDADSGSAS<br>GPRDLRCYRISSDRYECSWQYEGPTAGVSHFLRCCLSSGRCCYFA<br>AGSATRLQFSDQAGVSVLYTVTLWVESWARNQTEKSPEVTLQLYN<br>SVKYEPPLGDIKVSKLAGQLRMEWETPD-<br>NQVGAEVQFRHRTPSSP<br>WKLGDCGPQDDDTESCLCPLEMNVAQEFQLRRRQLGSQGSSWSKW<br>SSPVCVPPENPPQPQVRFSVEQLGQDGRRRLTLKEQPTQLELPEG<br>CQGLAPGTEVTYRLQLHMLSCPCKAKATRTLHLGKMPYLSGAAYN<br>VAVISSNQFGPGLNQTWHIPADTHTEPVALNISVGTNGTTMYWPA<br>RAQSMTYCIEWQPVGQDGGLATCSLTAPQDPDPAGMATYSWSRES<br>GAMGQEKCYYITIFASAHPEKLTLWSTVLSTYHFGGNASAAGTPH<br>HVSVKNHSLDSVSVDWAPSLLSTCPGVLKEYVVRCRDEDSKQVSE<br>HPVQPTETQVTLSGLRAGVAYTVQVRADTAWLRGVWSQPQRFSIE<br>VQVSDWLIFFASLGSFLSILLVGLYLGLNRAARHLCPPLPTPC<br>RASSAIEFPGGKETWQWINPVDFQEEASLQEALVEMSWDKGETE<br>PLEKTELPEGAPELALDTELSLEDGDRCKAKM |
| 90 | QVQLVESGGGVVQPGRSLRLSCAASGFTFTSYGMSWVRQAPGKGL<br>EWVAGISYSGSDTEYADSVKGRFTISRDNSKNTLYLQMNSLRAED<br>TAVYYCARSPDYIIDYGFDYWGRGTLVTVSSASTKGPSVFPLAPS<br>SKSTSGGTAALGCLVKDYFPEPVTVSWNSGALTSGVHTFPAVLQS<br>SGLYSLSSVVTVPSSSLGTQTYICNVNHKPSNTKVDKRVEPKSCD<br>KTHTCPPCPAPELLGGPSVFLFPPKPKDTLMISRTPEVTCVVVDV<br>SHEDPEVKFNWYVDGVEVHNAKTKPREEQYNSTYRVVSVLTVLHQ<br>DWLNGKEYKCKVSNKALPAPIEKTISKAKGQPREPQVYTLPPSRE<br>EMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>K |
| 91 | QVQLVESGGGVVQPGRSLRLSCAASGFTFTSYGMSWVRQAPGKGL<br>EWVAGISYDASDTEYADSVKGRFTISRDNSKNTLYLQMNSLRAED<br>TAVYYCARSPDYIIDYGFDYWGRGTLVTVSSASTKGPSVFPLAPS<br>SKSTSGGTAALGCLVKDYFPEPVTVSWNSGALTSGVHTFPAVLQS<br>SGLYSLSSVVTVPSSSLGTQTYICNVNHKPSNTKVDKRVEPKSCD<br>KTHTCPPCPAPELLGGPSVFLFPPKPKDTLMISRTPEVTCVVVDV<br>SHEDPEVKFNWYVDGVEVHNAKTKPREEQYNSTYRVVSVLTVLHQ<br>DWLNGKEYKCKVSNKALPAPIEKTISKAKGQPREPQVYTLPPSRE<br>EMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>K |
| 92 | QVQLVQSGAEVKKPGASVKVSCKASGYTFTGYYMHWVRQAPGQGL<br>EWMGMIGPQHGEAIYAQKFQGRVTMTRDTSISTAYMELSRLRSED<br>TAVYYCARESTDSDESPFDYWGQGTLVTVSSASTKGPSVFPLAPS<br>SKSTSGGTAALGCLVKDYFPEPVTVSWNSGALTSGVHTFPAVLQS<br>SGLYSLSSVVTVPSSSLGTQTYICNVNHKPSNTKVDKRVEPKSCD<br>KTHTCPPCPAPELLGGPSVFLFPPKPKDTLMISRTPEVTCVVVDV<br>SHEDPEVKFNWYVDGVEVHNAKTKPREEQYNSTYRVVSVLTVLHQ<br>DWLNGKEYKCKVSNKALPAPIEKTISKAKGQPREPQVYTLPPSRE<br>EMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>K |
| 93 | QVQLVQSGAEVKKPGASVKVSCKASGYTFTGYYMHWVRQAPGQGL<br>EWMGMIGPQHGEAIYAQKFQGRVTMTRDTSISTAYMELSRLRSDD<br>TAVYYCARESTDSDESPFDYWGQGTLVTVSSASTKGPSVFPLAPS<br>SKSTSGGTAALGCLVKDYFPEPVTVSWNSGALTSGVHTFPAVLQS<br>SGLYSLSSVVTVPSSSLGTQTYICNVNHKPSNTKVDKRVEPKSCD<br>KTHTCPPCPAPELLGGPSVFLFPPKPKDTLMISRTPEVTCVVVDV<br>SHEDPEVKFNWYVDGVEVHNAKTKPREEQYNSTYRVVSVLTVLHQ<br>DWLNGKEYKCKVSNKALPAPIEKTISKAKGQPREPQVYTLPPSRE<br>EMTKNQVSLTCLVKGFYPSDIAVEWESNGQPENNYKTTPPVLDSD<br>GSFFLYSKLTVDKSRWQQGNVFSCSVMHEALHNHYTQKSLSLSPG<br>K |
| 94 | caggtgcaattggtggaaagcggcggaggcgtggtgcagcctggc<br>agaagcctgagactgagctgtgccgccagcggcttcaccttcacc<br>agctacggcatgagctgggtccgacaggcccctggcaagggcctg<br>gaatgggtggccggcatcagctacagcggcagcgacaccgagtac<br>gccgacagcgtgaagggccggttcaccatcagccgggacaacagc<br>aagaacaccctgtacctgcagatgaacagcctgcgggccgaggac<br>accgccgtgtactactgcgccagaagccccgactacatcatcgac<br>tacggcttcgactactggggcagaggcaccctggtcaccgtcagc<br>tcagcctccaccaagggcccatcggtcttccccctggcacctcc<br>tccaagagcacctctgggggcacagcggccctgggctgcctggtc<br>aaggactacttccccgaaccggtgacggtgtcgtggaactcaggc<br>gccctgaccagcggcgtgcacaccttcccggctgtcctacagtcc<br>tcaggactctactccctcagcagcgtggtgaccgtgccctccagc<br>agcttgggcacccagacctacatctgcaacgtgaatcacaagccc<br>agcaacaccaaggtggacaagagagttgaacccaaatcttgtgac<br>aaaactcacacatgcccaccgtgcccagcacctgaactcctgggg<br>ggaccgtcagtcttcctcttccccccaaaacccaaggacaccctc<br>atgatctcccggacccctgaggtcacatgcgtggtggtggacgtg<br>agccacgaagaccctgaggtcaagttcaactggtacgtggacggc<br>gtggaggtgcataatgccaagacaaagccgcgggaggagcagtac<br>aacagcacgtaccgggtggtcagcgtcctcaccgtcctgcaccag<br>gactggctgaatggcaaggagtacaagtgcaaggtctccaacaaa<br>gccctcccagcccccatcgagaaaaccatctccaaagccaaaggg<br>cagccccgagaaccacaggtgtacaccctgcccccatcccgggag<br>gagatgaccaagaaccaggtcagcctgacctgtctggtcaaaggc<br>ttctatcccagcgacatcgccgtggagtgggagagcaatgggcag<br>ccggagaacaactacaagaccacgcctcccgtgctggactccgac<br>ggctccttcttcctctacagcaagctcaccgtggacaagagcagg<br>tggcagcaggggaacgtcttctcatgctccgtgatgcatgaggct<br>ctgcacaaccactacacgcagaagagcctctccctgtctccgggt<br>aaa |
| 95 | caggtgcaattggtggaaagcggcggaggcgtggtgcagcctggc<br>agaagcctgagactgagctgtgccgccagcggcttcaccttcacc<br>agctacggcatgagctgggtccgacaggcccctggcaagggcctg<br>gaatgggtggccggcatcagctacgacgccagcgacaccgagtac<br>gccgacagcgtgaagggccggttcaccatcagccgggacaacagc<br>aagaacaccctgtacctgcagatgaacagcctgcgggccgaggac<br>accgccgtgtactactgcgccagaagccccgactacatcatcgac<br>tacggcttcgactactggggcagaggcaccctggtcaccgtcagc |

TABLE 12-continued

Useful amino acid and nucleotide sequences for practicing the invention

| SEQ ID NO: | Describes the amino acid or nucleotide sequence below: |
|---|---|
| | tcagcctccaccaagggtccatcggtcttcccctggcaccctc
tccaagagcacctctgggggcacagcggccctgggctgcctggtc
aaggactacttccccgaaccggtgacggtgtcgtggaactcaggc
gccctgaccagcggcgtgcacaccttcccggctgtcctacagtcc
tcaggactctactccctcagcagcgtggtgaccgtgccctccagc
agcttgggcacccagacctacatctgcaacgtgaatcacaagccc
agcaacaccaaggtggacaagagagttgagcccaaatcttgtgac
aaaactcacacatgcccaccgtgcccagcacctgaactcctgggg
ggaccgtcagtcttcctcttccccccaaaacccaaggacaccctc
atgatctcccggacccctgaggtcacatgcgtggtggtggacgtg
agccacgaagaccctgaggtcaagttcaactggtacgtggacggc
gtggaggtgcataatgccaagacaaagccgcgggaggagcagtac
aacagcacgtaccgggtggtcagcgtcctcaccgtcctgcaccag
gactggctgaatggcaaggagtacaagtgcaaggtctccaacaaa
gcccttccagcccccatcgagaaaaccatctccaaagccaaaggg
cagccccgagaaccacaggtgtacaccctgcccccatcccgggag
gagatgaccaagaaccaggtcagcctgacctgcctggtcaaaggc
ttctatcccagcgacatcgccgtggagtgggagagcaatgggcag
ccggagaacaactacaagaccacgcctcccgtgctggactccgac
ggctccttcttcctctacagcaagctcaccgtggacaagagcagg
tggcagcaggggaacgtcttctcatgctccgtgatgcatgaggct
ctgcacaaccactacacgcagaagagcctctccctgtctccgggt
aaa |
| 96 | caggtgcaattggtgcagtctggcgccgaagtgaagaaacctggg
gctagtgtgaaggtgtcctgcaaggcagcggctacaccttcacc
ggctactacatgcactgggtccgacaggcccctggacagggcctg
gaatggatgggcatgatcggcccccagcacggcgaggccatctac
gcccagaaattccagggcagagtgaccatgacccgggacaccagc
atcagcaccgcctacatggaactgagccggctgcgggagcgaggac
accgccgtgtactactgcgccagagagagcaccgacagcgacgag
agccccttcgactactggggccagggcaccctggtcaccgtcagc
tcagcctccaccaagggtccatcggtcttcccctggcaccctcc
tccaagagcacctctgggggcacagcggccctgggctgcctggtc
aaggactacttccccgaaccggtgacggtgtcgtggaactcaggc
gccctgaccagcggcgtgcacaccttcccggctgtcctacagtcc
tcaggactctactccctcagcagcgtggtgaccgtgccctccagc
agcttgggcacccagacctacatctgcaacgtgaatcacaagccc
agcaacaccaaggtggacaagagagttgagcccaaatcttgtgac
aaaactcacacatgcccaccgtgcccagcacctgaactcctgggg
ggaccgtcagtcttcctcttccccccaaaacccaaggacaccctc
atgatctcccggacccctgaggtcacatgcgtggtggtggacgtg
agccacgaagaccctgaggtcaagttcaactggtacgtggacggc
gtggaggtgcataatgccaagacaaagccgcgggaggagcagtac
aacagcacgtaccgggtggtcagcgtcctcaccgtcctgcaccag
gactggctgaatggcaaggagtacaagtgcaaggtctccaacaaa
gcccttccagcccccatcgagaaaaccatctccaaagccaaaggg
cagccccgagaaccacaggtgtacaccctgcccccatcccgggag
gagatgaccaagaaccaggtcagcctgacctgcctggtcaaaggc
ttctatcccagcgacatcgccgtggagtgggagagcaatgggcag
ccggagaacaactacaagaccacgcctcccgtgctggactccgac
ggctccttcttcctctacagcaagctcaccgtggacaagagcagg
tggcagcaggggaacgtcttctcatgctccgtgatgcatgaggct
ctgcacaaccactacacgcagaagagcctctccctgtctccgggt
aaa |
| 97 | caggtgcaattggtgcagtctggcgccgaagtgaagaaacctggg
gccagcgtgaaggtgtcctgcaaggc-
cagcggctacaccttcacc
ggctactacatgcactgggtccgacaggcccctggacagggcctg
gaatggatgggcatgatcggcccccagcacggcgaggccatctac
gcccagaaattccagggcagagtgac-
catgacccgggacaccagc
atcagcaccgcctacatggaactgagccggctgcgggagcgacgac
accgccgtgtactactgcgccagagagagcaccgacagcgacgag
agccccttcgac-
tactggggccagggcaccctggtcaccgtcagc
tcagcctccaccaagggtccatcggtcttcccctggcaccctcc
tccaagagcacctctgggggcacagcggccctgggctgcctggtc
aaggactacttccccgaaccggtgacg-
gtgtcgtggaactcaggc
gccctgaccagcggcgtgcacaccttcccggctgtcctacagtcc
tcaggactctactccctcagcagcgtggtgaccgtgccctccagc |

TABLE 12-continued

Useful amino acid and nucleotide sequences for practicing the invention

| SEQ ID NO: | Describes the amino acid or nucleotide sequence below: |
|---|---|
| | agcttgggcacccagacctacatctg-
caacgtgaatcacaagccc
agcaacaccaaggtggacaagagagttgagcccaaatcttgtgac
aaaactcacacatgcccaccgtgcccag-
cacctgaactcctgggg
ggaccgtcagtcttcctcttccccccaaaacccaaggacaccctc
atgatctcccggacccctgaggtcacat-
gcgtggtggtggacgtg
agccacgaagaccctgaggtcaagt-
tcaactggtacgtggacggc
gtggaggtgcataatgccaagacaaagccgcgggaggagcagtac
aacagcacgtaccgggtggtcagcgtc-
ctcaccgtcctgcaccag
gactggctgaatggcaaggagtacaagt-
gcaaggtctccaacaaa
gcccttccagcccccatcgagaaaaccatctccaaagccaaaggg
cagccccgagaaccacaggtgtacac-
cctgcccccatcccgggag
gagatgaccaagaaccaggtcagcct-
gacctgcctggtcaaaggc
ttctatcccagcgacatcgccgtggagtgggagagcaatgggcag
ccggagaacaactacaagaccacgcct-
cccgtgctggactccgac
ggctccttcttcctctacagcaagct-
caccgtggacaagagcagg
tggcagcaggggaacgtcttctcatgctccgtgatgcatgaggct
ctgcacaaccactacacgcagaagagcctctccctgtctccgggt
aaa |
| 98 | MEPLVTWVVPLLLLFLRSRQGAACGTSECCFQDPPYSDADSGSAS
GPRDLSCYRISSAGYECSWQYEGPTAGVSHFLRCCLSSGRCCYFA
TGSATRLQFSDQAGVSVLHTVTLWVESWARNRTEKSPEVTLQLYK
SVKYKPPLGDIKVSKLAGQLRMEWETPDNQVGAEVQFRHRTPSSS
WKLGDCGPQDDDTESCLCPLEMNVAQEFQLRRRRLGSQGSSWSKW
SSPVCVPPENPPQPQVRFSVEQLGRDGRRRLTLKEQPTQLELPEG
CQGPAPGVEVTYQLQLHMLSCPCKAKATRTLPLEKMPYLSGAAYN
VAVISSNRFGPGPNQTWHIPADTHTEPVALNISVGTNGTTMYWPA
RAQSTTYCIEWQPVGQEGSLATCNLTAPQDPDPAGMATYSWSRES
GAMGQEKCYHITIFASAHPKKLTLWSTVLSTYHFGGNASAAGTPH
HVSVKNHSLDSVSVDWAPSLLSTCPGVLKEYVVRCRDEDSNQVSE
HPVQPTETQVTLSDLRAGVAYTVQVRADTAWLRGAWSQPQRFSIK
VQVSDWFIFFASLGSFLSILLVGVLGYLGLNRATRHLCPPLPTPC
ASSAIQFPAGKETWQWINPVDFQEEASLQEALVVEMSWDKGERTE
LLEKAELPEGAPELALDTQLSLEDGDRCKAKM |
| 99 | MCHQQLVISWFSLVFLASPLVAIWELKKDVYVVELDWYPDAPGEM
VVLTCDTPEEDGITWTLDQSSEVLGSGKTLTIQVKEFGDAGQYTC
HKGGEVLSHSLLLLHKKEDGIWSTDILKDQKEPKNKTFLRCEAKN
YSGRFTCWWLTTISTDLTFSVKSSRGSSDPQGVTCGAATLSAERV
RGDNKEYEYSVECQEDSACPAAEESLPIEVMVDAVHKLKYENYTS
SFFIRDIIKPDPPKNLQLKPLKNSRQVEVSWEYPDTWSTPHSYFS
LTFCVQVQGKSKREKKDRVFTDKTSATVICRKNASISVRAQDRYY
SSSWSEWASVPCS |
| 100 | MWPPGSASQPPPSPAAATGLHPAARPVSLQCRLSMCPARSLLLVA
TLVLLDHLSLARNLPVATPDPGMFPCLHHSQNLLRAVSNMLQKAR
QTLEFYPCTSEEIDHEDITKDKTSVEACLPLELTKNESCLNSRE
TSFITNGSCLASRKTSFMMALCLSSIYEDLKMYQVEFKTMNAKLL
MDPKRQIFLDQNMLAVIDELMQALNFNSETVPQKSSLEEPDFYKT
KIKLCILLHAFRIRAVTIDRVMSYLNAS |
| 101 | MLGSRAVMLLLLLPWTAQGRAVPGGSSPAWTQCQQLSQKLCTLAW
SAHPLVGHMDLREEGDEETTNDVPHIQCGDGCDPQGLRDNSQFCL
QRIHQGLIFYEKLLGSDIFTGEPSLLPDSPVGQLHASLLGLSQLL
QPEGHHWETQQIPSLSPSQPWQRLLLRFKILRSLQAFVAVAARVF
AHGAATLSP |

Results

Examples mAb1 to mAb16 were obtained and produced as described below:

Screening and Identification of Fab Antibodies with High Affinity to IL12Rb1

Library screening combined with rapid maturation was performed as described (Knappik et al., 2000 J. Mol. Biol. 296: 57-86; Pressler et al., 2009 Immunotherapy 1(4): 571-83). In addition to the classical screening confirmed binders (Fab) were immediately tested for binding on human (Kit-225) and cyno (HSC-F) cells naturally expressing the IL-12R. This allowed the selection of 119 unique clones from the originally observed 5520 hits. They were then tested for functional inhibition in the human whole blood assay, followed by the cyno version for effective candidates (46 from 20 families, falling into 4 epitope bins). Thus 6 efficacious functional inhibitors (from 4 families) were initially shortlisted due to their $IC_{50}$ inhibiting cyno and human IL-12 functions. The top 4 (designated MOR11873, MOR11878, MOR11879 and MOR11880 respectively; the two latter being two different frameworks containing identical CDRs) were selected for optimization engineering to improve their developability and prepared in four different IgG1 Fc versions for the assessment of the optimal silent version (ADCC/CDC pending).

Expression and Purification of HuCA®-Fab Antibodies in *E. coli*

To facilitate rapid expression of soluble Fab, the Fab encoding inserts of the selected HuCAL PLATINUM® phage were subcloned into an expression vector for IPTG inducible Fab expression in mammalian cell lines and purification of the Fab by Ni-NTA chromatography. Expression of Fab fragments in TG-1 cells was induced by addition of IPTG. Cells were disrupted using lysozyme and Fab fragments isolated by Ni-NTA chromatography (Bio-Rad, Germany). Protein concentrations were determined by UV-spectrophotometry. Purity of Fab fragments was analyzed in denatured, reduced state using SDS-PAGE and in native state by HP-SEC.

Conversion to IgG

In order to express full length IgG, variable domain fragments of heavy ($V_H$) and light chains ($V_L$) of the four lead candidates MOR11873, MOR11878, MOR11879 and MOR11880 were subcloned from Fab expression vectors into appropriate expression vectors for human IgG1f wild type, human IgG1fD265A, human IgG1fN297A, and human IgG1fL234AL235A hereafter referred as "LALA", resulting in expression vectors for the production of the 16 antibodies according to the invention, mAb1-mAb16 as described in Table 13 below:

TABLE 13

Description of the variable regions and IgG1 Fc region of mAb1-mAb16

| Example | MOR# variable region and IgG1 Fc region |
|---|---|
| mAb1 | MOR11873 with IgG1 LALA Fc variant |
| mAb2 | MOR11873 with IgG1 D265A Fc variant |
| mAb3 | MOR11873 with IgG1 N297A Fc variant |
| mAb4 | MOR11878 with IgG1 LALA Fc variant |
| mAb5 | MOR11878 with IgG1 D265A Fc variant |
| mAb6 | MOR11878 with IgG1 N297A Fc variant |
| mAb7 | MOR11879 with IgG1 LALA Fc variant |
| mAb8 | MOR11879 with IgG1 D265A Fc variant |
| mAb9 | MOR11879 with IgG1 N297A Fc variant |
| mAb10 | MOR11880 with IgG1 LALA Fc variant |
| mAb11 | MOR11880 with IgG1 D265A Fc variant |
| mAb12 | MOR11880 with IgG1 N297A Fc variant |
| mAb13 | MOR11873 with IgG1 wild type Fc |
| mAb14 | MOR11878 with IgG1 wild type Fc |
| mAb15 | MOR11879 with IgG1 wild type Fc |
| mAb16 | MOR11880 with IgG1 wild type Fc |

Transient Expression and Purification of Human IgG

Eukaryotic HKB11 cells were transfected with expression vector DNA encoding for heavy and light chains of IgGs mAb1, mAb4, mAb7 and mAb10. After sterile filtration, the solution was subjected to standard protein A affinity chromatography (MabSelect SURE, GE Healthcare). Protein concentrations were determined by UV-spectrophotometry. Purity of IgG was analyzed under denaturing, reducing and non-reducing conditions in SDS-PAGE or by using Caliper LabChip® System or Agilent BioAnalyzer and in native state by HP-SEC. All candidate antibodies were tested for their IL12Rβ1 binding affinity (SPR, $K_D$ nM), IL12/IL23 in vitro competitive binding inhibition, IL12/IL18 dependent IFNγ production in human and in cynomolgus monkeys according to the methods described in the Method paragraph above. The results are shown in Table 14.

TABLE 14

Profiling data of mAb1, mAb4, mAb7 and mAb10

| Selection Criteria | mAb1 | mAb4 | mAb7 | mAb10 |
|---|---|---|---|---|
| human IL12Rβ1 binding affinity (SPR, $K_D$ pM) | 40 | 20 | 40 | 40 |
| cyno IL12Rβ1 binding affinity (SPR, $K_D$ pM) | 100 | 100 | 600 | 600 |
| Cell binding Kit225 (human natural expression; $EC_{50}$, pM) | 6 | 5 | 10 | 11 |
| Cell binding human T-cells (human natural expression; $EC_{50}$, pM) | 33 | 38 | 15 | 16 |
| Cell binding HSC-F (cyno natural expression; $EC_{50}$, pM) | 23 | 13 | 23 | n.d. |
| Cell binding cyno T-cells (cyno natural expression; $EC_{50}$, pM) | 55 | 41 | 36 | 28 |
| IL12/IL23 competitive binding ($IC_{50}$, pM) | 8/18 | 8/13 | 8/20 | 8/20 |
| IL12/IL18 dependent IFNγ production In human blood cells ($IC_{50}$, pM) | 28 | 77 | 24 | 42 |
| IL12/IL18 dependent IFNγ production In cyno blood cells ($IC_{50}$, pM) | 239 | 216 | 284 | 1182 |
| Epitope bin (A-D) | B | B | B | B |
| analytical SEC (% monomer) | 97.8 | 98.5 | 98.0 | 98.7 |
| titer (mg/L) | 51.0 | 33.8 | 51.7 | 42.9 |
| pI (in-silico prediction) | 8.6 | 8.2 | 6.8 | 7.5 |
| Tm (° C., pH 7.4, IgG data) | 76.0 | 75.3 | 68.5 | 68.0 |
| protein A recovery (%) | 62.5 | 76.2 | 36.8 | 69.5 |
| Tm (° C., pH 7.4, Fab data) | 68.0 | 54.5 | 66.5 | 66.3 |
| Tm (° C., pH 6.0, Fab data) | 73.0 | 74.5 | 69.0 | 69.5 |
| Tm (° C., pH 3.5, Fab data) | 56.8 | 56.0 | 55.8 | 55.8 |

Remarkably, the antibodies of the invention have $K_D$ affinity and $IC_{50}$ below 100 pM, and even below 10 pM for IL12 competitive binding as determined by the functional human assays, therefore being particularly suitable for use as a drug. Moreover, they possess advantageous developability properties. They also cross-react with cynomolgous monkey IL12Rβ1 (SEQ ID NO:98) and the coding sequences encoding the variable regions can be easily transferred for generating silent IgG1 antibodies, for example comprising the IgG1 Fc variant containing the L234A L235A mutation, or the IgG1 Fc variant containing the D265A mutation, or the IgG1 Fc variant containing the N297A mutation.

Epitope Binning Experiment

The antibodies were tested in cross-competition (epitope binning) experiments and 4 distinct groups could be distinguished among all originally identified functionally inhibiting mAbs. The selected top 4 candidates MOR11873, MOR11878, MOR11879 and MOR11880 all happen to fall into the second group designated epitope bin B and thus compete with each other. Since all mAb1-mAb16 have a binding region derived from one of the four top candidates, it is therefore expected that all mAb1-mAb16 antibodies compete with each other.

Summary of Amide Hydrogen/Deuterium Exchange Mass Spectrometry Epitope Mapping

In order to develop a clearer picture of the binding relationship between the antibodies of the invention, epitope mapping studies were carried out. The object was to determine the site of binding of the candidate monoclonal antibodies on the target human IL12Rbeta1 molecule. In particular, the objective was to identify the specific amino acid residues of human IL12Rbeta1 that are involved in the binding interaction between the antibodies and target. Epitope mapping was generally carried out using state of the art techniques available to the skilled person. In particular, Hydrogen/Deuterium exchange mass spectrometry was used to probe the structure of human IL12Rbeta1 for amino acid residues which influence antibody binding, i.e. are implicated in the relevant epitopes. The results in Table 15 show Δ (Delta) values, i.e. the difference in deuteration between the IL12Rbeta1/antibody complex and the free IL12Rbeta1 protein. Negative values are indicative of solvent protection in the antibody-antigen complex and interpreted as the most likely sites of interaction.

The H/DxMS epitope mapping results show that one peptide corresponding to amino acid residues 416-429 of the human IL12Rbeta1 sequence (ITIFASAHPEKLTL) exhibited protection for all groups of antibodies. This data is consistent with the fact that these groups of antibodies show competition with each other, indicating that the 416-ITIFASAHPEKLTL-429 peptide corresponds to an epitope for all three groups of antibodies. Furthermore, these data are consistent with that fact that the antibodies are cross-reactive with cynomolgus IL12Rbeta1, but not the equivalent rodent sequences (mouse and rat). A comparison of this epitope sequence in human, cynomolgus, rat and mouse is shown in Table 16, where the aligned epitope sequence is underlined

TABLE 16

Comparison of IL12Rbeta1 antibodies epitope sequence in human, cynomolgus, rat and mouse

| Species | Amino acid sequence |
|---|---|
| Human | GAMGQEKCYY<br>ITIFASAHPEKLTLWSTVLSTYHFGGNASAAG<br>TPHHVSVKNHSLDSVSVD |
| Cyno | GAMGQEKCYH<br>ITIFASAHPKKLTLWSTVLSTYHFGGNASAAG<br>TPHHVSVKNHSLDSVSVD |
| Murine | -TLEQEECYR<br>ITVFASKNPKNPMLWATVLSSYYFGGNASRAG<br>TPRHVSVRNQTGDSVSVE |
| Rat | -TLDQEECYR<br>ITVFASKNPKNPMMWATVLSSYYFGGNVSRVG<br>TPRHVSVRNHTEDSVSVE |

The cynomolgus and human sequences only differ by one amino acid residue in this epitope sequence, which accounts for the cross reactivity of the antibodies with both human and cynomolgus sequences. In contrast, the rodent sequences in this epitope show greater differences compared to the human and cynomolgus sequences, this being consistent with the lack of specificity of the antibodies with the rodent IL12Rbeta1 proteins.

TABLE 15

H/DxMS epitope mapping data

| IL12Rbeta 1 peptide sequence | Position of peptide in IL12Rbeta1 | MOR11873 Δ (Delta) | MOR11878 Δ (Delta) | MOR11880 Δ (Delta) |
|---|---|---|---|---|
| FAAGSATRLQFSDQAGVSVL | 89-108 | 3.84 | 1.59 | 2.58 |
| TRLQFSDQAGVSVL | 95-108 | 0.98 | | |
| YNSVKYEPPLGDIKVSKLAGQL | 134-155 | 1.91 | | |
| CSLTAPQDPDPAGM | 383-396 | 0.36 | | |
| TAPQDPDPAGMAT | 386-398 | 0.05 | 0.04 | 0.03 |
| ITIFASAHPEKLTL | 416-429 | -0.37 | -0.38 | -0.48 |
| LSTCPGVLKE | 471-480 | 0.61 | | 1.02 |
| YVVRCRDEDSKQ | 481-492 | -0.05 | | -0.04 |
| SGLRAGVA | 508-515 | 0.46 | 0.16 | 0.31 |
| YTVQVRADTAWLRGVWSQPQRF | 516-537 | 0.81 | | |
| VRADTAWLRGVWSQPQRF | 520-537 | 0.99 | 0.24 | 0.15 |

The invention claimed is:

1. An isolated nucleic acid encoding at least the heavy and/or light variable region(s) of the antibody or protein with an antigen-binding portion of an antibody, comprising a variable heavy chain amino acid sequence comprising an HCDR1 sequence of SEQ ID NO:1, an HCDR2 sequence of SEQ ID NO:2, an HCDR3 sequence of SEQ ID NO:3 and a variable light chain amino acid sequence comprising an LCDR1 sequence of SEQ ID NO:4, an LCDR2 sequence of SEQ ID NO:5 and an LCDR3 sequence of SEQ ID NO: 6, wherein said antibody or protein binds to the IL12Rβ1 polypeptide of SEQ ID NO:89.

2. A cloning or expression vector comprising one or more nucleic acids according to claim 1.

3. A host cell comprising one or more cloning or expression vectors of claim 2.

4. A cloning or expression vector, suitable for the recombinant production of an antibody according to claim 1 in a host cell, said host cell or expression vector comprising at least one nucleic acid selected from the group consisting of SEQ ID NOs: 73, 77, 81, 85, and 94.

5. A cloning or expression vector according to claim 4, comprising the coding sequences selected from the group consisting of: (a) SEQ ID NO:73 and SEQ ID NO:85; (b) SEQ ID NO:77 and SEQ ID NO:85; (c) SEQ ID NO:81 and SEQ ID NO:85; and (d) SEQ ID NO:94 and SEQ ID NO:85; wherein said coding sequences are operatively linked to a promoter sequence.

6. A host cell comprising one or more cloning or expression vectors of claim 5.

7. A host cell comprising one or more cloning or expression vectors of claim 4.

8. An isolated nucleic acid encoding at least the heavy and/or light variable region(s) of the antibody or protein with an antigen-binding portion of an antibody, comprising a $V_H$ polypeptide sequence having at least 95 percent sequence identity to SEQ ID NO: 49 and a $V_L$ polypeptide sequence having at least 95 percent sequence identity to SEQ ID NO: 50, wherein the antibody binds to the IL12Rβ1 polypeptide of SEQ ID NO: 89.

9. A cloning or expression vector comprising one or more nucleic acids according to claim 8.

10. A host cell comprising one or more cloning or expression vectors of claim 9.

11. An isolated nucleic acid encoding at least the heavy and/or light variable region(s) of the antibody or protein with an antigen-binding portion of an antibody, comprising a $V_H$ polypeptide sequence of SEQ ID NO: 49 and a $V_L$ polypeptide sequence of SEQ ID NO: 50.

12. A cloning or expression vector comprising one or more nucleic acids according to claim 11.

13. A host cell comprising one or more cloning or expression vectors of claim 12.

14. An isolated nucleic acid encoding the antibody or protein with an antigen-binding portion of an antibody, comprising (a) heavy chain amino acid sequence of SEQ ID NO:57 and light chain amino acid sequence of SEQ ID NO:69; (b) heavy chain amino acid sequence of SEQ ID NO:61 and light chain amino acid sequence of SEQ ID NO:69; (c) heavy chain amino acid sequence of SEQ ID NO:65 and light chain amino acid sequence of SEQ ID NO:69; or (d) heavy chain amino acid sequence of SEQ ID NO:90 and light chain amino acid sequence of SEQ ID NO:69.

15. A cloning or expression vector comprising one or more nucleic acids according to claim 14.

16. A host cell comprising one or more cloning or expression vectors of claim 15.

\* \* \* \* \*

SEQUENCE LISTING

<160> NUMBER OF SEQ ID NOS: 101

<210> SEQ ID NO 1
<211> LENGTH: 5
<212> TYPE: PRT
<213> ORGANISM: Homo sapiens

<400> SEQUENCE: 1

Ser Tyr Gly Met Ser
1               5

<210> SEQ ID NO 2
<211> LENGTH: 17
<212> TYPE: PRT
<213> ORGANISM: Homo sapiens

<400> SEQUENCE: 2

Gly Ile Ser Tyr Ser Gly Ser Asp Thr Glu Tyr Ala Asp Ser Val Lys
1               5                   10                  15

Gly

<210> SEQ ID NO 3
<211> LENGTH: 12
<212> TYPE: PRT
<213> ORGANISM: Homo sapiens

<400> SEQUENCE: 3

Ser Pro Asp Tyr Ile Ile Asp Tyr Gly Phe Asp Tyr
1               5                   10

<210> SEQ ID NO 4
<211> LENGTH: 11
<212> TYPE: PRT
<213> ORGANISM: Homo sapiens

<400> SEQUENCE: 4

Arg Ala Ser Gln Gly Ile Ser Ser Asp Leu Ala
1               5                   10

<210> SEQ ID NO 5
<211> LENGTH: 7
<212> TYPE: PRT
<213> ORGANISM: Homo sapiens

<400> SEQUENCE: 5

Asp Ala Ser Ser Leu Gln Ser
1               5

<210> SEQ ID NO 6
<211> LENGTH: 9
<212> TYPE: PRT
<213> ORGANISM: Homo sapiens

<400> SEQUENCE: 6

Gln Gln Tyr Trp Ile Tyr Pro Phe Thr
1               5

<210> SEQ ID NO 7
<211> LENGTH: 5
<212> TYPE: PRT
<213> ORGANISM: Homo sapiens

<400> SEQUENCE: 7

Ser Tyr Gly Met Ser

-continued

```
<210> SEQ ID NO 8
<211> LENGTH: 17
<212> TYPE: PRT
<213> ORGANISM: Homo sapiens

<400> SEQUENCE: 8

Gly Ile Ser Tyr Asp Ala Ser Asp Thr Glu Tyr Ala Asp Ser Val Lys
1               5                   10                  15

Gly

<210> SEQ ID NO 9
<211> LENGTH: 12
<212> TYPE: PRT
<213> ORGANISM: Homo sapiens

<400> SEQUENCE: 9

Ser Pro Asp Tyr Ile Ile Asp Tyr Gly Phe Asp Tyr
1               5                   10

<210> SEQ ID NO 10
<211> LENGTH: 11
<212> TYPE: PRT
<213> ORGANISM: Homo sapiens

<400> SEQUENCE: 10

Arg Ala Ser Gln Gly Ile Ser Ser Asp Leu Ala
1               5                   10

<210> SEQ ID NO 11
<211> LENGTH: 7
<212> TYPE: PRT
<213> ORGANISM: Homo sapiens

<400> SEQUENCE: 11

Asp Ala Ser Ser Leu Gln Ser
1               5

<210> SEQ ID NO 12
<211> LENGTH: 9
<212> TYPE: PRT
<213> ORGANISM: Homo sapiens

<400> SEQUENCE: 12

Gln Gln Tyr Trp Trp Tyr Pro Phe Thr
1               5

<210> SEQ ID NO 13
<211> LENGTH: 5
<212> TYPE: PRT
<213> ORGANISM: Homo sapiens

<400> SEQUENCE: 13

Gly Tyr Tyr Met His
1               5

<210> SEQ ID NO 14
<211> LENGTH: 17
<212> TYPE: PRT
<213> ORGANISM: Homo sapiens

<400> SEQUENCE: 14

Met Ile Gly Pro Gln His Gly Glu Ala Ile Tyr Ala Gln Lys Phe Gln
```

```
1               5                   10                  15

Gly

<210> SEQ ID NO 15
<211> LENGTH: 12
<212> TYPE: PRT
<213> ORGANISM: Homo sapiens

<400> SEQUENCE: 15

Glu Ser Thr Asp Ser Asp Glu Ser Pro Phe Asp Tyr
1               5                   10

<210> SEQ ID NO 16
<211> LENGTH: 11
<212> TYPE: PRT
<213> ORGANISM: Homo sapiens

<400> SEQUENCE: 16

Ser Gly Asp Asn Ile Arg Ser Tyr Tyr Val Ser
1               5                   10

<210> SEQ ID NO 17
<211> LENGTH: 7
<212> TYPE: PRT
<213> ORGANISM: Homo sapiens

<400> SEQUENCE: 17

Asp Asp Ser Asp Arg Pro Ser
1               5

<210> SEQ ID NO 18
<211> LENGTH: 11
<212> TYPE: PRT
<213> ORGANISM: Homo sapiens

<400> SEQUENCE: 18

Gln Ser Tyr Gly Ser His Ser Asn Phe Val Val
1               5                   10

<210> SEQ ID NO 19
<211> LENGTH: 5
<212> TYPE: PRT
<213> ORGANISM: Homo sapiens

<400> SEQUENCE: 19

Gly Tyr Tyr Met His
1               5

<210> SEQ ID NO 20
<211> LENGTH: 17
<212> TYPE: PRT
<213> ORGANISM: Homo sapiens

<400> SEQUENCE: 20

Met Ile Gly Pro Gln His Gly Glu Ala Ile Tyr Ala Gln Lys Phe Gln
1               5                   10                  15

Gly

<210> SEQ ID NO 21
<211> LENGTH: 12
<212> TYPE: PRT
<213> ORGANISM: Homo sapiens

<400> SEQUENCE: 21
```

```
Glu Ser Thr Asp Ser Asp Glu Ser Pro Phe Asp Tyr
1               5                   10
```

<210> SEQ ID NO 22
<211> LENGTH: 11
<212> TYPE: PRT
<213> ORGANISM: Homo sapiens

<400> SEQUENCE: 22

```
Ser Gly Asp Asn Ile Arg Ser Tyr Tyr Val Ser
1               5                   10
```

<210> SEQ ID NO 23
<211> LENGTH: 7
<212> TYPE: PRT
<213> ORGANISM: Homo sapiens

<400> SEQUENCE: 23

```
Asp Asp Ser Asp Arg Pro Ser
1               5
```

<210> SEQ ID NO 24
<211> LENGTH: 11
<212> TYPE: PRT
<213> ORGANISM: Homo sapiens

<400> SEQUENCE: 24

```
Gln Ser Tyr Gly Ser His Ser Asn Phe Val Val
1               5                   10
```

<210> SEQ ID NO 25
<211> LENGTH: 7
<212> TYPE: PRT
<213> ORGANISM: Homo sapiens

<400> SEQUENCE: 25

```
Gly Phe Thr Phe Thr Ser Tyr
1               5
```

<210> SEQ ID NO 26
<211> LENGTH: 6
<212> TYPE: PRT
<213> ORGANISM: Homo sapiens

<400> SEQUENCE: 26

```
Ser Tyr Ser Gly Ser Asp
1               5
```

<210> SEQ ID NO 27
<211> LENGTH: 12
<212> TYPE: PRT
<213> ORGANISM: Homo sapiens

<400> SEQUENCE: 27

```
Ser Pro Asp Tyr Ile Ile Asp Tyr Gly Phe Asp Tyr
1               5                   10
```

<210> SEQ ID NO 28
<211> LENGTH: 7
<212> TYPE: PRT
<213> ORGANISM: Homo sapiens

<400> SEQUENCE: 28

```
Ser Gln Gly Ile Ser Ser Asp
```

```
<210> SEQ ID NO 29
<211> LENGTH: 3
<212> TYPE: PRT
<213> ORGANISM: Homo sapiens

<400> SEQUENCE: 29

Asp Ala Ser
1

<210> SEQ ID NO 30
<211> LENGTH: 6
<212> TYPE: PRT
<213> ORGANISM: Homo sapiens

<400> SEQUENCE: 30

Tyr Trp Ile Tyr Pro Phe
1               5

<210> SEQ ID NO 31
<211> LENGTH: 7
<212> TYPE: PRT
<213> ORGANISM: Homo sapiens

<400> SEQUENCE: 31

Gly Phe Thr Phe Thr Ser Tyr
1               5

<210> SEQ ID NO 32
<211> LENGTH: 6
<212> TYPE: PRT
<213> ORGANISM: Homo sapiens

<400> SEQUENCE: 32

Ser Tyr Asp Ala Ser Asp
1               5

<210> SEQ ID NO 33
<211> LENGTH: 12
<212> TYPE: PRT
<213> ORGANISM: Homo sapiens

<400> SEQUENCE: 33

Ser Pro Asp Tyr Ile Ile Asp Tyr Gly Phe Asp Tyr
1               5                   10

<210> SEQ ID NO 34
<211> LENGTH: 7
<212> TYPE: PRT
<213> ORGANISM: Homo sapiens

<400> SEQUENCE: 34

Ser Gln Gly Ile Ser Ser Asp
1               5

<210> SEQ ID NO 35
<211> LENGTH: 3
<212> TYPE: PRT
<213> ORGANISM: Homo sapiens

<400> SEQUENCE: 35

Asp Ala Ser
1
```

```
<210> SEQ ID NO 36
<211> LENGTH: 6
<212> TYPE: PRT
<213> ORGANISM: Homo sapiens

<400> SEQUENCE: 36

Tyr Trp Trp Tyr Pro Phe
1               5

<210> SEQ ID NO 37
<211> LENGTH: 7
<212> TYPE: PRT
<213> ORGANISM: Homo sapiens

<400> SEQUENCE: 37

Gly Tyr Thr Phe Thr Gly Tyr
1               5

<210> SEQ ID NO 38
<211> LENGTH: 6
<212> TYPE: PRT
<213> ORGANISM: Homo sapiens

<400> SEQUENCE: 38

Gly Pro Gln His Gly Glu
1               5

<210> SEQ ID NO 39
<211> LENGTH: 12
<212> TYPE: PRT
<213> ORGANISM: Homo sapiens

<400> SEQUENCE: 39

Glu Ser Thr Asp Ser Asp Glu Ser Pro Phe Asp Tyr
1               5                   10

<210> SEQ ID NO 40
<211> LENGTH: 7
<212> TYPE: PRT
<213> ORGANISM: Homo sapiens

<400> SEQUENCE: 40

Asp Asn Ile Arg Ser Tyr Tyr
1               5

<210> SEQ ID NO 41
<211> LENGTH: 3
<212> TYPE: PRT
<213> ORGANISM: Homo sapiens

<400> SEQUENCE: 41

Asp Asp Ser
1

<210> SEQ ID NO 42
<211> LENGTH: 8
<212> TYPE: PRT
<213> ORGANISM: Homo sapiens

<400> SEQUENCE: 42

Tyr Gly Ser His Ser Asn Phe Val
1               5

<210> SEQ ID NO 43
```

-continued

```
<211> LENGTH: 7
<212> TYPE: PRT
<213> ORGANISM: Homo sapiens

<400> SEQUENCE: 43

Gly Tyr Thr Phe Thr Gly Tyr
1               5

<210> SEQ ID NO 44
<211> LENGTH: 6
<212> TYPE: PRT
<213> ORGANISM: Homo sapiens

<400> SEQUENCE: 44

Gly Pro Gln His Gly Glu
1               5

<210> SEQ ID NO 45
<211> LENGTH: 12
<212> TYPE: PRT
<213> ORGANISM: Homo sapiens

<400> SEQUENCE: 45

Glu Ser Thr Asp Ser Asp Glu Ser Pro Phe Asp Tyr
1               5                   10

<210> SEQ ID NO 46
<211> LENGTH: 7
<212> TYPE: PRT
<213> ORGANISM: Homo sapiens

<400> SEQUENCE: 46

Asp Asn Ile Arg Ser Tyr Tyr
1               5

<210> SEQ ID NO 47
<211> LENGTH: 3
<212> TYPE: PRT
<213> ORGANISM: Homo sapiens

<400> SEQUENCE: 47

Asp Asp Ser
1

<210> SEQ ID NO 48
<211> LENGTH: 8
<212> TYPE: PRT
<213> ORGANISM: Homo sapiens

<400> SEQUENCE: 48

Tyr Gly Ser His Ser Asn Phe Val
1               5

<210> SEQ ID NO 49
<211> LENGTH: 121
<212> TYPE: PRT
<213> ORGANISM: Homo sapiens

<400> SEQUENCE: 49

Gln Val Gln Leu Val Glu Ser Gly Gly Val Gln Pro Gly Arg
1               5                   10                  15

Ser Leu Arg Leu Ser Cys Ala Ala Ser Gly Phe Thr Phe Thr Ser Tyr
            20                  25                  30

Gly Met Ser Trp Val Arg Gln Ala Pro Gly Lys Gly Leu Glu Trp Val
```

```
            35                  40                  45
Ala Gly Ile Ser Tyr Ser Gly Ser Asp Thr Glu Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Pro Asp Tyr Ile Ile Asp Tyr Gly Phe Asp Tyr Trp Gly
            100                 105                 110

Arg Gly Thr Leu Val Thr Val Ser Ser
            115                 120

<210> SEQ ID NO 50
<211> LENGTH: 109
<212> TYPE: PRT
<213> ORGANISM: Homo sapiens

<400> SEQUENCE: 50

Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Asp
             20                  25                  30

Leu Ala Trp Tyr Gln Gln Lys Pro Gly Lys Ala Pro Lys Leu Leu Ile
         35                  40                  45

Tyr Asp Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Trp Ile Tyr Pro Phe
                 85                  90                  95

Thr Phe Gly Gln Gly Thr Lys Val Glu Ile Lys Arg Thr
            100                 105

<210> SEQ ID NO 51
<211> LENGTH: 121
<212> TYPE: PRT
<213> ORGANISM: Homo sapiens

<400> SEQUENCE: 51

Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Thr Ser Tyr
             20                  25                  30

Gly Met Ser Trp Val Arg Gln Ala Pro Gly Lys Gly Leu Glu Trp Val
         35                  40                  45

Ala Gly Ile Ser Tyr Asp Ala Ser Asp Thr Glu Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Pro Asp Tyr Ile Ile Asp Tyr Gly Phe Asp Tyr Trp Gly
            100                 105                 110

Arg Gly Thr Leu Val Thr Val Ser Ser
            115                 120
```

```
<210> SEQ ID NO 52
<211> LENGTH: 109
<212> TYPE: PRT
<213> ORGANISM: Homo sapiens

<400> SEQUENCE: 52

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Asp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Trp Tyr Pro Phe
                85                  90                  95

Thr Phe Gly Gln Gly Thr Lys Val Glu Ile Lys Arg Thr
            100                 105

<210> SEQ ID NO 53
<211> LENGTH: 121
<212> TYPE: PRT
<213> ORGANISM: Homo sapiens

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Met Ile Gly Pro Gln His Gly Glu Ala Ile Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Glu Ser Thr Asp Ser Asp Glu Ser Pro Phe Asp Tyr Trp Gly
            100                 105                 110

Gln Gly Thr Leu Val Thr Val Ser Ser
        115                 120

<210> SEQ ID NO 54
<211> LENGTH: 110
<212> TYPE: PRT
<213> ORGANISM: Homo sapiens

<400> SEQUENCE: 54

Asp Ile Glu Leu Thr Gln Pro Pro Ser Val Ser Val Ser Pro Gly Gln
1               5                   10                  15

Thr Ala Ser Ile Thr Cys Ser Gly Asp Asn Ile Arg Ser Tyr Tyr Val
            20                  25                  30

Ser Trp Tyr Gln Gln Lys Pro Gly Gln Ala Pro Val Leu Val Ile Tyr
        35                  40                  45

Asp Asp Ser Asp Arg Pro Ser Gly Ile Pro Glu Arg Phe Ser Gly Ser
50                  55                  60
```

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Gly Ser His Ser Asn Phe
                85                  90                  95

Val Val Phe Gly Gly Gly Thr Lys Leu Thr Val Leu Gly Gln
            100                 105                 110

<210> SEQ ID NO 55
<211> LENGTH: 121
<212> TYPE: PRT
<213> ORGANISM: Homo sapiens

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Met Ile Gly Pro His Gly Glu Ala Ile Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Ser Thr Asp Ser Asp Glu Ser Pro Phe Asp Tyr Trp Gly
            100                 105                 110

Gln Gly Thr Leu Val Thr Val Ser Ser
        115                 120

<210> SEQ ID NO 56
<211> LENGTH: 110
<212> TYPE: PRT
<213> ORGANISM: Homo sapiens

<400> SEQUENCE: 56

Ser Tyr Glu Leu Thr Gln Pro Leu Ser Val Ser Val Ala Leu Gly Gln
1               5                   10                  15

Thr Ala Arg Ile Thr Cys Ser Gly Asp Asn Ile Arg Ser Tyr Tyr Val
                20                  25                  30

Ser Trp Tyr Gln Gln Lys Pro Gly Gln Ala Pro Val Leu Val Ile Tyr
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Ser Tyr Gly Ser His Ser Asn Phe
                85                  90                  95

Val Val Phe Gly Gly Gly Thr Lys Leu Thr Val Leu Gly Gln
            100                 105                 110

<210> SEQ ID NO 57
<211> LENGTH: 451
<212> TYPE: PRT
<213> ORGANISM: Homo sapiens

<400> SEQUENCE: 57

```
Gln Val Gln Leu Val Glu Ser Gly Gly Val Val Pro Gly Arg
  1               5                  10                  15

Ser Leu Arg Leu Ser Cys Ala Ala Ser Gly Phe Thr Phe Thr Ser Tyr
             20                  25                  30

Gly Met Ser Trp Val Arg Gln Ala Pro Gly Lys Gly Leu Glu Trp Val
             35                  40                  45

Ala Gly Ile Ser Tyr Ser Gly Ser Asp Thr Glu Tyr Ala Asp Ser Val
         50                  55                  60

Lys Gly Arg Phe Thr Ile Ser Arg Asp Asn Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Pro Asp Tyr Ile Ile Asp Tyr Gly Phe Asp Tyr Trp Gly
            100                 105                 110

Arg Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
            210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
```

His Glu Ala Leu His Asn His Tyr Thr Gln Lys Ser Leu Ser Leu Ser
            435                 440                 445

Pro Gly Lys
    450

<210> SEQ ID NO 58
<211> LENGTH: 451
<212> TYPE: PRT
<213> ORGANISM: Homo sapiens

<400> SEQUENCE: 58

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Ser Tyr
            20                  25                  30

Gly Met Ser Trp Val Arg Gln Ala Pro Gly Lys Gly Leu Glu Trp Val
        35                  40                  45

Ala Gly Ile Ser Tyr Asp Ala Ser Asp Thr Glu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Pro Asp Tyr Ile Ile Asp Tyr Gly Phe Asp Tyr Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

```
Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 59
<211> LENGTH: 451
<212> TYPE: PRT
<213> ORGANISM: Homo sapiens

<400> SEQUENCE: 59

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Met Ile Gly Pro Gln His Gly Glu Ala Ile Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Glu Ser Thr Asp Ser Asp Glu Ser Pro Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255
```

-continued

```
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
        290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 60
<211> LENGTH: 451
<212> TYPE: PRT
<213> ORGANISM: Homo sapiens

<400> SEQUENCE: 60

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
            20                  25                  30
Tyr Met His Trp Val Arg Gln Ala Pro Gly Gln Gly Leu Glu Trp Met
        35                  40                  45
Gly Met Ile Gly Pro Gln His Gly Glu Ala Ile Tyr Ala Gln Lys Phe
    50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Glu Ser Thr Asp Ser Asp Glu Ser Pro Phe Asp Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
```

165                 170                 175
Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Glu Glu Met Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly Lys
    450

<210> SEQ ID NO 61
<211> LENGTH: 451
<212> TYPE: PRT
<213> ORGANISM: Homo sapiens

<400> SEQUENCE: 61

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Ser Tyr
            20                  25                  30

Gly Met Ser Trp Val Arg Gln Ala Pro Gly Lys Gly Leu Glu Trp Val
        35                  40                  45

Ala Gly Ile Ser Tyr Ser Gly Ser Asp Thr Glu Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95
Ala Arg Ser Pro Asp Tyr Ile Ile Asp Tyr Gly Phe Asp Tyr Trp Gly
            100                 105                 110
Arg Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Arg Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Ala Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 62
<211> LENGTH: 451
<212> TYPE: PRT
<213> ORGANISM: Homo sapiens

<400> SEQUENCE: 62
```

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Thr Ser Tyr
            20                  25                  30

Gly Met Ser Trp Val Arg Gln Ala Pro Gly Lys Gly Leu Glu Trp Val
        35                  40                  45

Ala Gly Ile Ser Tyr Asp Ala Ser Asp Thr Glu Tyr Ala Asp Ser Val
    50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Arg Ser Pro Asp Tyr Ile Ile Asp Tyr Gly Phe Asp Tyr Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ala Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415
```

```
Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 63
<211> LENGTH: 451
<212> TYPE: PRT
<213> ORGANISM: Homo sapiens

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Met Ile Gly Pro Gln His Gly Glu Ala Ile Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Glu Ser Thr Asp Ser Asp Glu Ser Pro Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ala Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335
```

```
Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 64
<211> LENGTH: 451
<212> TYPE: PRT
<213> ORGANISM: Homo sapiens

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
            35                  40                  45

Gly Met Ile Gly Pro Gln His Gly Glu Ala Ile Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Glu Ser Thr Asp Ser Asp Glu Ser Pro Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
```

```
            245                 250                 255
Ile Ser Arg Thr Pro Glu Val Thr Cys Val Val Val Ala Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
450

<210> SEQ ID NO 65
<211> LENGTH: 451
<212> TYPE: PRT
<213> ORGANISM: Homo sapiens

<400> SEQUENCE: 65

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Ser Tyr
            20                  25                  30

Gly Met Ser Trp Val Arg Gln Ala Pro Gly Lys Gly Leu Glu Trp Val
        35                  40                  45

Ala Gly Ile Ser Tyr Ser Gly Ser Asp Thr Glu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Pro Asp Tyr Ile Ile Asp Tyr Gly Phe Asp Tyr Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160
```

-continued

```
Ser Trp Asn Ser Gly Ala Leu Thr Ser Gly Val His Thr Phe Pro Ala
            165                 170                 175
Val Leu Gln Ser Ser Gly Leu Tyr Ser Leu Ser Ser Val Val Thr Val
        180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Arg Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Ala Ser Thr Tyr
        290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 66
<211> LENGTH: 451
<212> TYPE: PRT
<213> ORGANISM: Homo sapiens

<400> SEQUENCE: 66

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Thr Ser Tyr
            20                  25                  30
Gly Met Ser Trp Val Arg Gln Ala Pro Gly Lys Gly Leu Glu Trp Val
        35                  40                  45
Ala Gly Ile Ser Tyr Asp Ala Ser Asp Thr Glu Tyr Ala Asp Ser Val
    50                  55                  60
Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Ser Pro Asp Tyr Ile Ile Asp Tyr Gly Phe Asp Tyr Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 67
<211> LENGTH: 451
<212> TYPE: PRT
<213> ORGANISM: Homo sapiens
```

```
<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Met Ile Gly Pro Gln His Gly Glu Ala Ile Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Glu Ser Thr Asp Ser Asp Glu Ser Pro Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415
```

```
Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 68
<211> LENGTH: 451
<212> TYPE: PRT
<213> ORGANISM: Homo sapiens

<400> SEQUENCE: 68

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Met Ile Gly Pro His Gly Glu Ala Ile Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Ser Thr Asp Ser Asp Glu Ser Pro Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
```

```
            325                 330                 335
Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
        450

<210> SEQ ID NO 69
<211> LENGTH: 214
<212> TYPE: PRT
<213> ORGANISM: Homo sapiens

<400> SEQUENCE: 69

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Asp
            20                  25                  30

Leu Ala Trp Tyr Gln Gln Lys Pro Gly Lys Ala Pro Lys Leu Leu Ile
            35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Ile Tyr Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 70
<211> LENGTH: 214
```

<212> TYPE: PRT
<213> ORGANISM: Homo sapiens

<400> SEQUENCE: 70

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Asp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Trp Tyr Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 71
<211> LENGTH: 214
<212> TYPE: PRT
<213> ORGANISM: Homo sapiens

<400> SEQUENCE: 71

Asp Ile Glu Leu Thr Gln Pro Pro Ser Val Ser Val Ser Pro Gly Gln
1               5                   10                  15

Thr Ala Ser Ile Thr Cys Ser Gly Asp Asn Ile Arg Ser Tyr Tyr Val
            20                  25                  30

Ser Trp Tyr Gln Gln Lys Pro Gly Gln Ala Pro Val Leu Val Ile Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Gly Ser His Ser Asn Phe
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

```
Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 72
<211> LENGTH: 214
<212> TYPE: PRT
<213> ORGANISM: Homo sapiens

<400> SEQUENCE: 72

Ser Tyr Glu Leu Thr Gln Pro Leu Ser Val Ser Val Ala Leu Gly Gln
1               5                   10                  15

Thr Ala Arg Ile Thr Cys Ser Gly Asp Asn Ile Arg Ser Tyr Tyr Val
            20                  25                  30

Ser Trp Tyr Gln Gln Lys Pro Gly Gln Ala Pro Val Leu Val Ile Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Ser Tyr Gly Ser His Ser Asn Phe
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 73
<211> LENGTH: 1353
<212> TYPE: DNA
<213> ORGANISM: Homo sapiens

<400> SEQUENCE: 73
caggtgcaat tggtggaaag cggcggaggc gtggtgcagc ctggcagaag cctgagactg     60
agctgtgccg ccagcggctt caccttcacc agctacggca tgagctgggt ccgacaggcc    120
```

```
cctggcaagg gcctggaatg ggtggccggc atcagctaca gcggcagcga caccgagtac    180
gccgacagcg tgaagggccg gttcaccatc agccgggaca cagcaagaa  cccctgtac    240 ctgcagatga acagcctgcg ggccgaggac accgccgtgt actactgcgc agaagcccc    300 gactacatca tcgactacgg cttcgactac tggggcagag gcaccctggt caccgtcagc    360
tcagcctcca ccaagggtcc atcggtcttc ccctggcac  cctcctccaa gagcacctct    420
gggggcacag cggccctggg ctgcctggtc aaggactact ccccgaacc  ggtgacggtg    480 tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gagagttgag    660
cccaaatctt gtgacaaaac tcacacatgc ccaccgtgcc cagcacctga agcagcgggg    720
ggaccgtcag tcttcctctt ccccccaaaa cccaaggaca ccctcatgat ctcccggacc    780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgggtggt cagcgtcctc accgtcctgc accaggactg gctgaatggc    960
aaggagtaca agtgcaaggt ctccaacaaa gccctcccag cccccatcga gaaaaccatc   1020
tccaaagcca aagggcagcc ccgagaacca caggtgtaca ccctgccccc atcccgggag   1080
gagatgacca agaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tacagcaagc tcaccgtgga caagagcagg   1260
tggcagcagg ggaacgtctt ctcatgctcc gtgatgcatg aggctctgca caaccactac   1320
acgcagaaga gcctctccct gtctccgggt aaa                                1353
```

```
<210> SEQ ID NO 74
<211> LENGTH: 1353
<212> TYPE: DNA
<213> ORGANISM: Homo sapiens

<400> SEQUENCE: 74
```

```
caggtgcaat tggtggaaag cggcggaggc gtggtgcagc ctggcagaag cctgagactg     60
agctgtgccg ccagcggctt caccttcacc agctacggca tgagctgggt ccgacaggcc    120
cctggcaagg gcctggaatg ggtggccggc atcagctacg acgccagcga caccgagtac    180
gccgacagcg tgaagggccg gttcaccatc agccgggaca cagcaagaa  cccctgtac    240 ctgcagatga acagcctgcg ggccgaggac accgccgtgt actactgcgc agaagcccc    300 gactacatca tcgactacgg cttcgactac tggggcagag gcaccctggt caccgtcagc    360
tcagcctcca ccaagggtcc atcggtcttc ccctggcac  cctcctccaa gagcacctct    420
gggggcacag cggccctggg ctgcctggtc aaggactact ccccgaacc  ggtgacggtg    480 tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gagagttgag    660
cccaaatctt gtgacaaaac tcacacatgc ccaccgtgcc cagcacctga agcagcgggg    720
ggaccgtcag tcttcctctt ccccccaaaa cccaaggaca ccctcatgat ctcccggacc    780
cctgaggtca catgcgtggt ggtggacgtg agccacgaag accctgaggt caagttcaac    840
```

| | |
|---|---|
| tggtacgtgg acggcgtgga ggtgcataat gccaagacaa agccgcggga ggagcagtac | 900 |
| aacagcacgt accgggtggt cagcgtcctc accgtcctgc accaggactg gctgaatggc | 960 |
| aaggagtaca agtgcaaggt ctccaacaaa gccctcccag cccccatcga gaaaaccatc | 1020 |
| tccaaagcca aagggcagcc ccgagaacca caggtgtaca ccctgccccc atcccgggag | 1080 |
| gagatgacca agaaccaggt cagcctgacc tgcctggtca aaggcttcta tcccagcgac | 1140 |
| atcgccgtgg agtgggagag caatgggcag ccggagaaca actacaagac cacgcctccc | 1200 |
| gtgctggact ccgacggctc cttcttcctc tacagcaagc tcaccgtgga caagagcagg | 1260 |
| tggcagcagg ggaacgtctt ctcatgctcc gtgatgcatg aggctctgca caaccactac | 1320 |
| acgcagaaga gcctctccct gtctccgggt aaa | 1353 |

<210> SEQ ID NO 75
<211> LENGTH: 1353
<212> TYPE: DNA
<213> ORGANISM: Homo sapiens

<400> SEQUENCE: 75

| | |
|---|---|
| caggtgcaat tggtgcagtc tggcgccgaa gtgaagaaac ctggggctag tgtgaaggtg | 60 |
| tcctgcaagg ccagcggcta caccttcacc ggctactaca tgcactgggt ccgacaggcc | 120 |
| cctggacagg gcctggaatg gatgggcatg atcggccccc agcacggcga ggccatctac | 180 |
| gcccagaaat ccagggcag agtgaccatg acccgggaca ccagcatcag caccgcctac | 240 |
| atggaactga gccggctgcg gagcgaggac accgccgtgt actactgcgc cagagagagc | 300 |
| accgacagcg acgagagccc cttcgactac tggggccagg gcaccctggt caccgtcagc | 360 |
| tcagcctcca ccaagggtcc atcggtcttc ccctggcac cctcctccaa gagcacctct | 420 |
| gggggcacag cggccctggg ctgcctggtc aaggactact tccccgaacc ggtgacggtg | 480 |
| tcgtggaact caggcgccct gaccagcggc gtgcacacct tcccggctgt cctacagtcc | 540 |
| tcaggactct actccctcag cagcgtggtg accgtgccct ccagcagctt gggcacccag | 600 |
| acctacatct gcaacgtgaa tcacaagccc agcaacacca aggtggacaa gagagttgag | 660 |
| cccaaatctt gtgacaaaac tcacacatgc ccaccgtgcc cagcacctga gcagcgggg | 720 |
| ggaccgtcag tcttcctctt ccccccaaaa cccaaggaca ccctcatgat ctcccggacc | 780 |
| cctgaggtca catgcgtggt ggtggacgtg agccacgaag accctgaggt caagttcaac | 840 |
| tggtacgtgg acggcgtgga ggtgcataat gccaagacaa agccgcggga ggagcagtac | 900 |
| aacagcacgt accgggtggt cagcgtcctc accgtcctgc accaggactg gctgaatggc | 960 |
| aaggagtaca agtgcaaggt ctccaacaaa gccctcccag cccccatcga gaaaaccatc | 1020 |
| tccaaagcca aagggcagcc ccgagaacca caggtgtaca ccctgccccc atcccgggag | 1080 |
| gagatgacca agaaccaggt cagcctgacc tgcctggtca aaggcttcta tcccagcgac | 1140 |
| atcgccgtgg agtgggagag caatgggcag ccggagaaca actacaagac cacgcctccc | 1200 |
| gtgctggact ccgacggctc cttcttcctc tacagcaagc tcaccgtgga caagagcagg | 1260 |
| tggcagcagg ggaacgtctt ctcatgctcc gtgatgcatg aggctctgca caaccactac | 1320 |
| acgcagaaga gcctctccct gtctccgggt aaa | 1353 |

<210> SEQ ID NO 76
<211> LENGTH: 1353
<212> TYPE: DNA
<213> ORGANISM: Homo sapiens

<400> SEQUENCE: 76

```
caggtgcaat tggtgcagtc tggcgccgaa gtgaagaaac ctggggccag cgtgaaggtg      60
tcctgcaagg ccagcggcta caccttcacc ggctactaca tgcactgggt ccgacaggcc     120
cctggacagg gcctggaatg gatgggcatg atcggccccc agcacggcga ggccatctac     180
gcccagaaat tccagggcag agtgaccatg acccgggaca ccagcatcag caccgcctac     240
atggaactga gccggctgcg gagcgacgac accgccgtgt actactgcgc cagagagagc     300
accgacagcg acgagagccc cttcgactac tgggggcagg gcaccctggt caccgtcagc     360
tcagcctcca ccaagggtcc atcggtcttc cccctggcac cctcctccaa gagcacctct     420
gggggcacag cggccctggg ctgcctggtc aaggactact ccccgaaccc ggtgacggtg     480
tcgtggaact caggcgccct gaccagcggc gtgcacacct tcccggctgt cctacagtcc     540
tcaggactct actccctcag cagcgtggtg accgtgccct ccagcagctt gggcacccag     600
acctacatct gcaacgtgaa tcacaagccc agcaacacca aggtggacaa gagagttgag     660
cccaaatctt gtgacaaaac tcacacatgc ccaccgtgcc cagcacctga gcagcgggg      720 ggaccgtcag tcttcctctt ccccccaaaa cccaaggaca cctcatgat ctcccggacc     780 cctgaggtca catgcgtggt ggtggacgtg agccacgaag accctgaggt caagttcaac     840
tggtacgtgg acggcgtgga ggtgcataat gccaagacaa agccgcggga ggagcagtac     900
aacagcacgt accgggtggt cagcgtcctc accgtcctgc accaggactg gctgaatggc     960
aaggagtaca agtgcaaggt ctccaacaaa gccctcccag cccccatcga gaaaaccatc    1020
tccaaagcca aagggcagcc ccgagaacca caggtgtaca ccctgccccc atcccgggag    1080
gagatgacca agaaccaggt cagcctgacc tgcctggtca aaggcttcta tcccagcgac    1140
atcgccgtgg agtgggagag caatgggcag ccggagaaca actacaagac cacgcctccc    1200
gtgctggact ccgacggctc cttcttcctc tacagcaagc tcaccgtgga caagagcagg    1260
tggcagcagg ggaacgtctt ctcatgctcc gtgatgcatg aggctctgca caaccactac    1320
acgcagaaga gcctctccct gtctccgggt aaa                                1353
```

<210> SEQ ID NO 77
<211> LENGTH: 1353
<212> TYPE: DNA
<213> ORGANISM: Homo sapiens

<400> SEQUENCE: 77

```
caggtgcaat tggtggaaag cggcggaggc gtggtgcagc ctggcagaag cctgagactg      60
agctgtgccg ccagcggctt caccttcacc agctacggca tgagctgggt ccgacaggcc     120
cctggcaagg gcctggaatg ggtggccggc atcagctaca gcggcagcga caccgagtac     180
gccgacagcg tgaagggccg gttcaccatc agccgggaca acagcaagaa caccctgtac     240
ctgcagatga acagcctgcg ggccgaggac accgccgtgt actactgcgc cagaagcccc     300
gactacatca tcgactacgg cttcgactac tgggggcagag gcaccctggt caccgtcagc     360
tcagcctcca ccaagggtcc atcggtcttc cccctggcac cctcctccaa gagcacctct     420
gggggcacag cggccctggg ctgcctggtc aaggactact ccccgaaccc ggtgacggtg     480
tcgtggaact caggcgccct gaccagcggc gtgcacacct tcccggctgt cctacagtcc     540
tcaggactct actccctcag cagcgtggtg accgtgccct ccagcagctt gggcacccag     600
acctacatct gcaacgtgaa tcacaagccc agcaacacca aggtggacaa gagagttgag     660
cccaaatctt gtgacaaaac tcacacatgc ccaccgtgcc cagcacctga actcctgggg     720
```

| | |
|---|---:|
| ggaccgtcag tcttcctctt cccccaaaa cccaaggaca ccctcatgat ctcccggacc | 780 |
| cctgaggtca catgcgtggt ggtggccgtg agccacgaag accctgaggt caagttcaac | 840 |
| tggtacgtgg acggcgtgga ggtgcataat gccaagacaa agccgcggga ggagcagtac | 900 |
| aacagcacgt accgggtggt cagcgtcctc accgtcctgc accaggactg gctgaatggc | 960 |
| aaggagtaca agtgcaaggt ctccaacaaa gccctcccag cccccatcga gaaaaccatc | 1020 |
| tccaaagcca agggcagcc ccgagaacca caggtgtaca ccctgccccc atcccgggag | 1080 |
| gagatgacca agaaccaggt cagcctgacc tgcctggtca aaggcttcta tcccagcgac | 1140 |
| atcgccgtgg agtgggagag caatgggcag ccggagaaca actacaagac cacgcctccc | 1200 |
| gtgctggact ccgacggctc cttcttcctc tacagcaagc tcaccgtgga caagagcagg | 1260 |
| tggcagcagg ggaacgtctt ctcatgctcc gtgatgcatg aggctctgca caaccactac | 1320 |
| acgcagaaga gcctctccct gtctccgggt aaa | 1353 |

<210> SEQ ID NO 78
<211> LENGTH: 1353
<212> TYPE: DNA
<213> ORGANISM: Homo sapiens

<400> SEQUENCE: 78

| | |
|---|---:|
| caggtgcaat tggtggaaag cggcggaggc gtggtgcagc ctggcagaag cctgagactg | 60 |
| agctgtgccg ccagcggctt caccttcacc agctacggca tgagctgggt ccgacaggcc | 120 |
| cctggcaagg gcctggaatg ggtggccggc atcagctacg acggcagcga caccgagtac | 180 |
| gccgacagcg tgaagggccg gttcaccatc agccgggaca cagcaagaa caccctgtac | 240 |
| ctgcagatga acagcctgcg ggccgaggac accgccgtgt actactgcgc cagaagcccc | 300 |
| gactacatca tcgactacgg cttcgactac tggggcagag gcaccctggt caccgtcagc | 360 |
| tcagcctcca ccaagggtcc atcggtcttc ccctggcac cctcctccaa gagcacctct | 420 |
| gggggcacag cggccctggg ctgcctggtc aaggactact tccccgaacc ggtgacggtg | 480 |
| tcgtggaact caggcgccct gaccagcggc gtgcacacct tcccggctgt cctacagtcc | 540 |
| tcaggactct actccctcag cagcgtggtg accgtgccct ccagcagctt gggcacccag | 600 |
| acctacatct gcaacgtgaa tcacaagccc agcaacacca aggtggacaa gagagttgag | 660 |
| cccaaatctt gtgacaaaac tcacacatgc ccaccgtgcc cagcacctga actcctgggg | 720 |
| ggaccgtcag tcttcctctt cccccaaaa cccaaggaca ccctcatgat ctcccggacc | 780 |
| cctgaggtca catgcgtggt ggtggccgtg agccacgaag accctgaggt caagttcaac | 840 |
| tggtacgtgg acggcgtgga ggtgcataat gccaagacaa agccgcggga ggagcagtac | 900 |
| aacagcacgt accgggtggt cagcgtcctc accgtcctgc accaggactg gctgaatggc | 960 |
| aaggagtaca agtgcaaggt ctccaacaaa gccctcccag cccccatcga gaaaaccatc | 1020 |
| tccaaagcca agggcagcc ccgagaacca caggtgtaca ccctgccccc atcccgggag | 1080 |
| gagatgacca agaaccaggt cagcctgacc tgcctggtca aaggcttcta tcccagcgac | 1140 |
| atcgccgtgg agtgggagag caatgggcag ccggagaaca actacaagac cacgcctccc | 1200 |
| gtgctggact ccgacggctc cttcttcctc tacagcaagc tcaccgtgga caagagcagg | 1260 |
| tggcagcagg ggaacgtctt ctcatgctcc gtgatgcatg aggctctgca caaccactac | 1320 |
| acgcagaaga gcctctccct gtctccgggt aaa | 1353 |

<210> SEQ ID NO 79
<211> LENGTH: 1353

```
<212> TYPE: DNA
<213> ORGANISM: Homo sapiens

<400> SEQUENCE: 79
caggtgcaat tggtgcagtc tggcgccgaa gtgaagaaac ctggggctag tgtgaaggtg      60
tcctgcaagg ccagcggcta caccttcacc ggctactaca tgcactgggt ccgacaggcc     120
cctggacagg gcctggaatg gatgggcatg atcggccccc agcacggcga ggccatctac     180
gcccagaaat tccagggcag agtgaccatg acccgggaca ccagcatcag caccgcctac     240
atggaactga ccggctgcg gagcgaggac accgccgtgt actactgcgc cagagagagc     300
accgacagcg acgagagccc cttcgactac tggggccagg gcaccctggt caccgtcagc     360
tcagcctcca ccaagggtcc atcggtcttc ccctggcac cctcctccaa gagcacctct     420
ggggccacag cggccctggg ctgcctggtc aaggactact cccccgaacc ggtgacggtg     480
tcgtggaact caggcgccct gaccagcggc gtgcacacct tcccggctgt cctacagtcc     540
tcaggactct actccctcag cagcgtggtg accgtgccct ccagcagctt gggcacccag     600
acctacatct gcaacgtgaa tcacaagccc agcaacacca aggtggacaa gagagttgag     660
cccaaatctt gtgacaaaac tcacacatgc ccaccgtgcc cagcacctga actcctgggg     720
ggaccgtcag tcttcctctt ccccccaaaa cccaaggaca cctcatgat ctcccggacc     780
cctgaggtca catgcgtggt ggtggccgtg agccacgaag accctgaggt caagttcaac     840
tggtacgtgg acggcgtgga ggtgcataat gccaagacaa agccgcggga ggagcagtac     900
aacagcacgt accgggtggt cagcgtcctc accgtcctgc accaggactg gctgaatggc     960
aaggagtaca agtgcaaggt ctccaacaaa gccctcccag cccccatcga gaaaaccatc    1020
tccaaagcca agggcagccc cgagaaccca caggtgtaca ccctgccccc atcccgggag    1080
gagatgacca agaaccaggt cagcctgacc tgcctggtca aaggcttcta tcccagcgac    1140
atcgccgtgg agtgggagag caatgggcag ccggagaaca actacaagac cacgcctccc    1200
gtgctggact ccgacggctc cttcttcctc tacagcaagc tcaccgtgga caagagcagg    1260
tggcagcagg ggaacgtctt ctcatgctcc gtgatgcatg aggctctgca caaccactac    1320
acgcagaaga gcctctccct gtctccgggt aaa                                  1353

<210> SEQ ID NO 80
<211> LENGTH: 1353
<212> TYPE: DNA
<213> ORGANISM: Homo sapiens

<400> SEQUENCE: 80
caggtgcaat tggtgcagtc tggcgccgaa gtgaagaaac ctggggccag cgtgaaggtg      60
tcctgcaagg ccagcggcta caccttcacc ggctactaca tgcactgggt ccgacaggcc     120
cctggacagg gcctggaatg gatgggcatg atcggccccc agcacggcga ggccatctac     180
gcccagaaat tccagggcag agtgaccatg acccgggaca ccagcatcag caccgcctac     240
atggaactga ccggctgcg gagcgacgac accgccgtgt actactgcgc cagagagagc     300
accgacagcg acgagagccc cttcgactac tgggggcagg gcaccctggt caccgtcagc     360
tcagcctcca ccaagggtcc atcggtcttc ccctggcac cctcctccaa gagcacctct     420
ggggccacag cggccctggg ctgcctggtc aaggactact cccccgaacc ggtgacggtg     480
tcgtggaact caggcgccct gaccagcggc gtgcacacct tcccggctgt cctacagtcc     540
tcaggactct actccctcag cagcgtggtg accgtgccct ccagcagctt gggcacccag     600
```

| | |
|---|---|
| acctacatct gcaacgtgaa tcacaagccc agcaacacca aggtggacaa gagagttgag | 660 |
| cccaaatctt gtgacaaaac tcacacatgc ccaccgtgcc cagcacctga actcctgggg | 720 |
| ggaccgtcag tcttcctctt ccccccaaaa cccaaggaca ccctcatgat ctcccggacc | 780 |
| cctgaggtca catgcgtggt ggtggccgtg agccacgaag accctgaggt caagttcaac | 840 |
| tggtacgtgg acggcgtgga ggtgcataat gccaagacaa agccgcggga ggagcagtac | 900 |
| aacagcacgt accgggtggt cagcgtcctc accgtcctgc accaggactg gctgaatggc | 960 |
| aaggagtaca agtgcaaggt ctccaacaaa gccctcccag cccccatcga gaaaaccatc | 1020 |
| tccaaagcca agggcagccc cgagaaccac aggtgtaca ccctgccccc atcccgggag | 1080 |
| gagatgacca agaaccaggt cagcctgacc tgcctggtca aaggcttcta tcccagcgac | 1140 |
| atcgccgtgg agtgggagag caatgggcag ccggagaaca actacaagac cacgcctccc | 1200 |
| gtgctggact ccgacggctc cttcttcctc tacagcaagc tcaccgtgga caagagcagg | 1260 |
| tggcagcagg ggaacgtctt ctcatgctcc gtgatgcatg aggctctgca caaccactac | 1320 |
| acgcagaaga gcctctccct gtctccgggt aaa | 1353 |

<210> SEQ ID NO 81
<211> LENGTH: 1353
<212> TYPE: DNA
<213> ORGANISM: Homo sapiens

<400> SEQUENCE: 81

| | |
|---|---|
| caggtgcaat tggtggaaag cggcggaggc gtggtgcagc ctggcagaag cctgagactg | 60 |
| agctgtgccg ccagcggctt caccttcacc agctacggca tgagctgggt ccgacaggcc | 120 |
| cctggcaagg gcctggaatg ggtggccggc atcagctaca gcggcagcga caccgagtac | 180 |
| gccgacagcg tgaagggccg gttcaccatc agccgggaca cagcaagaa caccctgtac | 240 |
| ctgcagatga acagcctgcg ggccgaggac accgccgtgt actactgcgc cagaagcccc | 300 |
| gactacatca tcgactacgg cttcgactac tggggcagag gcaccctggt caccgtcagc | 360 |
| tcagcctcca ccaagggtcc atcggtcttc cccctggcac cctcctccaa gagcacctct | 420 |
| gggggcacag cggccctggg ctgcctggtc aaggactact tccccgaacc ggtgacggtg | 480 |
| tcgtggaact caggcgccct gaccagcggc gtgcacacct tcccggctgt cctacagtcc | 540 |
| tcaggactct actccctcag cagcgtggtg accgtgccct ccagcagctt gggcacccag | 600 |
| acctacatct gcaacgtgaa tcacaagccc agcaacacca aggtggacaa gagagttgag | 660 |
| cccaaatctt gtgacaaaac tcacacatgc ccaccgtgcc cagcacctga actcctgggg | 720 |
| ggaccgtcag tcttcctctt ccccccaaaa cccaaggaca ccctcatgat ctcccggacc | 780 |
| cctgaggtca catgcgtggt ggtggacgtg agccacgaag accctgaggt caagttcaac | 840 |
| tggtacgtgg acggcgtgga ggtgcataat gccaagacaa agccgcggga ggagcagtac | 900 |
| gccagcacgt accgggtggt cagcgtcctc accgtcctgc accaggactg gctgaatggc | 960 |
| aaggagtaca agtgcaaggt ctccaacaaa gccctcccag cccccatcga gaaaaccatc | 1020 |
| tccaaagcca agggcagccc cgagaaccac aggtgtaca ccctgccccc atcccgggag | 1080 |
| gagatgacca agaaccaggt cagcctgacc tgcctggtca aaggcttcta tcccagcgac | 1140 |
| atcgccgtgg agtgggagag caatgggcag ccggagaaca actacaagac cacgcctccc | 1200 |
| gtgctggact ccgacggctc cttcttcctc tacagcaagc tcaccgtgga caagagcagg | 1260 |
| tggcagcagg ggaacgtctt ctcatgctcc gtgatgcatg aggctctgca caaccactac | 1320 |
| acgcagaaga gcctctccct gtctccgggt aaa | 1353 |

<210> SEQ ID NO 82
<211> LENGTH: 1353
<212> TYPE: DNA
<213> ORGANISM: Homo sapiens

<400> SEQUENCE: 82

| | | | | | |
|---|---|---|---|---|---|
| caggtgcaat | tggtggaaag | cggcggaggc | gtggtgcagc | ctggcagaag | cctgagactg | 60 |
| agctgtgccg | ccagcggctt | caccttcacc | agctacggca | tgagctgggt | ccgacaggcc | 120 |
| cctggcaagg | gcctggaatg | ggtggccggc | atcagctacg | acgccagcga | caccgagtac | 180 |
| gccgacagcg | tgaagggccg | gttcaccatc | agcggggaca | acagcaagaa | caccctgtac | 240 |
| ctgcagatga | acagcctgcg | ggccgaggac | accgccgtgt | actactgcgc | cagaagcccc | 300 |
| gactacatca | tcgactacgg | cttcgactac | tggggcagag | gcaccctggt | caccgtcagc | 360 |
| tcagcctcca | ccaagggtcc | atcggtcttc | cccctggcac | cctcctccaa | gagcacctct | 420 |
| gggggcacag | cggccctggg | ctgcctggtc | aaggactact | tccccgaacc | ggtgacggtg | 480 |
| tcgtggaact | caggcgccct | gaccagcggc | gtgcacacct | tcccggctgt | cctacagtcc | 540 |
| tcaggactct | actccctcag | cagcgtggtg | accgtgccct | ccagcagctt | gggcacccag | 600 |
| acctacatct | gcaacgtgaa | tcacaagccc | agcaacacca | aggtggacaa | gagagttgag | 660 |
| cccaaatctt | gtgacaaaac | tcacacatgc | ccaccgtgcc | cagcacctga | actcctgggg | 720 |
| ggaccgtcag | tcttcctctt | ccccccaaaa | cccaaggaca | cctcatgat | ctcccggacc | 780 |
| cctgaggtca | catgcgtggt | ggtggacgtg | agccacgaag | accctgaggt | caagttcaac | 840 |
| tggtacgtgg | acggcgtgga | ggtgcataat | gccaagacaa | agccgcggga | ggagcagtac | 900 |
| gccagcacgt | accgggtggt | cagcgtcctc | accgtcctgc | accaggactg | gctgaatggc | 960 |
| aaggagtaca | agtgcaaggt | ctccaacaaa | gccctcccag | cccccatcga | gaaaaccatc | 1020 |
| tccaaagcca | aagggcagcc | ccgagaacca | caggtgtaca | ccctgccccc | atcccgggag | 1080 |
| gagatgacca | agaaccaggt | cagcctgacc | tgcctggtca | aaggcttcta | tcccagcgac | 1140 |
| atcgccgtgg | agtgggagag | caatgggcag | ccggagaaca | actacaagac | cacgcctccc | 1200 |
| gtgctggact | ccgacggctc | cttcttcctc | tacagcaagc | tcaccgtgga | caagagcagg | 1260 |
| tggcagcagg | ggaacgtctt | ctcatgctcc | gtgatgcatg | aggctctgca | caaccactac | 1320 |
| acgcagaaga | gcctctccct | gtctccgggt | aaa | | | 1353 |

<210> SEQ ID NO 83
<211> LENGTH: 1353
<212> TYPE: DNA
<213> ORGANISM: Homo sapiens

<400> SEQUENCE: 83

| | | | | | |
|---|---|---|---|---|---|
| caggtgcaat | tggtgcagtc | tggcgccgaa | gtgaagaaac | ctggggctag | tgtgaaggtg | 60 |
| tcctgcaagg | ccagcggcta | caccttcacc | ggctactaca | tgcactgggt | ccgacaggcc | 120 |
| cctggacagg | gcctggaatg | gatgggcatg | atcggccccc | agcacggcga | ggccatctac | 180 |
| gcccagaaat | tccagggcag | agtgaccatg | accgggaca | ccagcatcag | caccgcctac | 240 |
| atggaactga | gccggctgcg | gagcgaggac | accgccgtgt | actactgcgc | cagagagagc | 300 |
| accgacagcg | acgagagccc | cttcgactac | tggggccagg | gcaccctggt | caccgtcagc | 360 |
| tcagcctcca | ccaagggtcc | atcggtcttc | cccctggcac | cctcctccaa | gagcacctct | 420 |
| gggggcacag | cggccctggg | ctgcctggtc | aaggactact | tccccgaacc | ggtgacggtg | 480 |

| | |
|---|---|
| tcgtggaact caggcgccct gaccagcggc gtgcacacct tcccggctgt cctacagtcc | 540 |
| tcaggactct actccctcag cagcgtggtg accgtgccct ccagcagctt gggcacccag | 600 |
| acctacatct gcaacgtgaa tcacaagccc agcaacacca aggtggacaa gagagttgag | 660 |
| cccaaatctt gtgacaaaac tcacacatgc ccaccgtgcc cagcacctga actcctgggg | 720 |
| ggaccgtcag tcttcctctt ccccccaaaa cccaaggaca ccctcatgat ctcccggacc | 780 |
| cctgaggtca catgcgtggt ggtggacgtg agccacgaag accctgaggt caagttcaac | 840 |
| tggtacgtgg acggcgtgga ggtgcataat gccaagacaa agccgcggga ggagcagtac | 900 |
| gccagcacgt accgggtggt cagcgtcctc accgtcctgc accaggactg gctgaatggc | 960 |
| aaggagtaca agtgcaaggt ctccaacaaa gccctcccag cccccatcga gaaaaccatc | 1020 |
| tccaaagcca agggcagccc cgagaaccca ggtgtacacc cctgcccc atcccgggag | 1080 |
| gagatgacca agaaccaggt cagcctgacc tgcctggtca aaggcttcta tcccagcgac | 1140 |
| atcgccgtgg agtgggagag caatgggcag ccggagaaca actacaagac cacgcctccc | 1200 |
| gtgctggact ccgacggctc cttcttcctc tacagcaagc tcaccgtgga caagagcagg | 1260 |
| tggcagcagg ggaacgtctt ctcatgctcc gtgatgcatg aggctctgca caaccactac | 1320 |
| acgcagaaga gcctctccct gtctccgggt aaa | 1353 |

<210> SEQ ID NO 84
<211> LENGTH: 1353
<212> TYPE: DNA
<213> ORGANISM: Homo sapiens

<400> SEQUENCE: 84

| | |
|---|---|
| caggtgcaat tggtgcagtc tggcgccgaa gtgaagaaac ctggggccag cgtgaaggtg | 60 |
| tcctgcaagg ccagcggcta caccttcacc ggctactaca tgcactgggt ccgacaggcc | 120 |
| cctggacagg gcctggaatg gatgggcatg atcggccccc agcacggcga ggccatctac | 180 |
| gcccagaaat tcagggcag agtgaccatg acccgggaca ccagcatcag caccgcctac | 240 |
| atggaactga gccggctgcg gagcgacgac accgccgtgt actactgcgc cagagagagc | 300 |
| accgacagcg acgagagccc cttcgactac tgggggcagg gcaccctggt caccgtcagc | 360 |
| tcagcctcca ccaagggtcc atcggtcttc cccctggcac cctcctccaa gagcacctct | 420 |
| gggggcacag cggccctggg ctgcctggtc aaggactact tccccgaacc ggtgacggtg | 480 |
| tcgtggaact caggcgccct gaccagcggc gtgcacacct tcccggctgt cctacagtcc | 540 |
| tcaggactct actccctcag cagcgtggtg accgtgccct ccagcagctt gggcacccag | 600 |
| acctacatct gcaacgtgaa tcacaagccc agcaacacca aggtggacaa gagagttgag | 660 |
| cccaaatctt gtgacaaaac tcacacatgc ccaccgtgcc cagcacctga actcctgggg | 720 |
| ggaccgtcag tcttcctctt ccccccaaaa cccaaggaca ccctcatgat ctcccggacc | 780 |
| cctgaggtca catgcgtggt ggtggacgtg agccacgaag accctgaggt caagttcaac | 840 |
| tggtacgtgg acggcgtgga ggtgcataat gccaagacaa agccgcggga ggagcagtac | 900 |
| gccagcacgt accgggtggt cagcgtcctc accgtcctgc accaggactg gctgaatggc | 960 |
| aaggagtaca agtgcaaggt ctccaacaaa gccctcccag cccccatcga gaaaaccatc | 1020 |
| tccaaagcca agggcagccc cgagaaccca ggtgtacacc cctgcccc atcccgggag | 1080 |
| gagatgacca agaaccaggt cagcctgacc tgcctggtca aaggcttcta tcccagcgac | 1140 |
| atcgccgtgg agtgggagag caatgggcag ccggagaaca actacaagac cacgcctccc | 1200 |
| gtgctggact ccgacggctc cttcttcctc tacagcaagc tcaccgtgga caagagcagg | 1260 |

```
tggcagcagg ggaacgtctt ctcatgctcc gtgatgcatg aggctctgca caaccactac    1320
acgcagaaga gcctctccct gtctccgggt aaa                                 1353

<210> SEQ ID NO 85
<211> LENGTH: 642
<212> TYPE: DNA
<213> ORGANISM: Homo sapiens

<400> SEQUENCE: 85
gccatccaga tgacccagag ccccagcagc ctgagcgcca gcgtgggcga cagagtgacc      60
atcacctgtc gggccagcca gggcatcagc agcgacctgg cctggtatca gcagaagccc     120
ggcaaggccc ccaagctgct gatctacgac gccagctccc tgcagagcgg cgtgcccagc     180
agattttccg gcagcggctc cggcaccgac ttcaccctga ccatcagcag cctgcagccc     240
gaggacttcg ccacctacta ctgccagcag tactggatct accccttcac cttcggccag     300
ggcaccaagg tggaaatcaa gcgtacggtg gccgctccca gcgtgttcat cttcccccc      360 agcgacgagc agctgaagag cggcaccgcc agcgtggtgt gcctgctgaa caacttctac     420
ccccgggagg ccaaggtgca gtggaaggtg gacaacgccc tgcagagcgg caacagccag     480
gaaagcgtca ccgagcagga cagcaaggac tccacctaca gcctgagcag caccctgacc     540
ctgagcaagg ccgactacga aagcacaag gtgtacgcct gcgaggtgac ccaccagggc     600
ctgtccagcc ccgtgaccaa gagcttcaac cggggcgagt gt                       642

<210> SEQ ID NO 86
<211> LENGTH: 642
<212> TYPE: DNA
<213> ORGANISM: Homo sapiens

<400> SEQUENCE: 86
gccatccaga tgacccagag ccccagcagc ctgagcgcca gcgtgggcga cagagtgacc      60
atcacctgtc gggccagcca gggcatcagc agcgacctgg cctggtatca gcagaagccc     120
ggcaaggccc ccaagctgct gatctacgac gccagctccc tgcagagcgg cgtgcccagc     180
agattttccg gcagcggctc cggcaccgac ttcaccctga ccatcagcag cctgcagccc     240
gaggacttcg ccacttacta ctgccagcag tactggtggt atcccttcac cttcggccag     300
ggcaccaagg tggaaatcaa gcgtacggtg gccgctccca gcgtgttcat cttcccccc      360 agcgacgagc agctgaagag cggcaccgcc agcgtggtgt gcctgctgaa caacttctac     420
ccccgggagg ccaaggtgca gtggaaggtg gacaacgccc tgcagagcgg caacagccag     480
gaaagcgtca ccgagcagga cagcaaggac tccacctaca gcctgagcag caccctgacc     540
ctgagcaagg ccgactacga aagcacaag gtgtacgcct gcgaggtgac ccaccagggc     600
ctgtccagcc ccgtgaccaa gagcttcaac cggggcgagt gt                       642

<210> SEQ ID NO 87
<211> LENGTH: 642
<212> TYPE: DNA
<213> ORGANISM: Homo sapiens

<400> SEQUENCE: 87
gacatcgagc tgacccagcc ccctagcgtg tccgtgtctc ctggccagac cgccagcatc      60
acctgtagcg gcgacaacat cagatcctac tacgtgtcct ggtatcagca gaagcccggc     120
caggcccccg tgctggtcat ctacgacgac agcgaccggc ccagcggcat ccccgagaga     180
```

-continued

```
ttcagcggca gcaacagcgg caacaccgcc accctgacca tcagcggcac ccaggccgag      240
gacgaggccg actactactg ccagagctac ggcagccaca gcaacttcgt ggtgttcggc      300
ggaggcacca agttaaccgt cctaggtcag cccaaggctg cccctcggt cactctgttc       360 ccgccctcct ctgaggagct tcaagccaac aaggccacac tggtgtgtct cataagtgac      420
ttctacccgg gagccgtgac agtggcctgg aaggcagata gcagcccgt caaggcggga      480 gtggagacca ccacaccctc aaacaaagc aacaacaagt acgcggccag cagctatctg       540
agcctgacgc ctgagcagtg aagtcccac agaagctaca gctgccaggt cacgcatgaa       600
gggagcaccg tggagaagac agtggcccct acagaatgtt ca                        642
```

<210> SEQ ID NO 88
<211> LENGTH: 642
<212> TYPE: DNA
<213> ORGANISM: Homo sapiens

<400> SEQUENCE: 88

```
tcttacgagc tgactcagcc cctgtccgtg tctgtggctc tgggccagac cgcccggatc       60
acatgcagcg gcgacaacat cagatcctac tacgtgtcct ggtatcagca gaagcctgga      120
caggcccccg tgctggtcat ctacgacgac agcgaccggc ccagcggcat ccccgagaga      180
ttcagcggaa gcaacagcgg caacaccgcc accctgacca tctccagagc ccaggccggc      240
gacgaggccg actactactg ccagagctac ggcagccaca gcaacttcgt ggtgttcggc      300
ggaggcacca agttaaccgt cctaggtcag cccaaggctg cccctcggt cactctgttc       360 ccgccctcct ctgaggagct tcaagccaac aaggccacac tggtgtgtct cataagtgac      420
ttctacccgg gagccgtgac agtggcctgg aaggcagata gcagcccgt caaggcggga      480 gtggagacca ccacaccctc aaacaaagc aacaacaagt acgcggccag cagctatctg       540
agcctgacgc ctgagcagtg aagtcccac agaagctaca gctgccaggt cacgcatgaa       600
gggagcaccg tggagaagac agtggcccct acagaatgtt ca                        642
```

<210> SEQ ID NO 89
<211> LENGTH: 662
<212> TYPE: PRT
<213> ORGANISM: Homo sapiens

<400> SEQUENCE: 89

```
Met Glu Pro Leu Val Thr Trp Val Val Pro Leu Leu Phe Leu Phe Leu
1               5                   10                  15

Leu Ser Arg Gln Gly Ala Ala Cys Arg Thr Ser Glu Cys Cys Phe Gln
            20                  25                  30

Asp Pro Pro Tyr Pro Asp Ala Asp Ser Gly Ser Ala Ser Gly Pro Arg
        35                  40                  45

Asp Leu Arg Cys Tyr Arg Ile Ser Ser Asp Arg Tyr Glu Cys Ser Trp
    50                  55                  60

Gln Tyr Glu Gly Pro Thr Ala Gly Val Ser His Phe Leu Arg Cys Cys
65                  70                  75                  80

Leu Ser Ser Gly Arg Cys Cys Tyr Phe Ala Ala Gly Ser Ala Thr Arg
                85                  90                  95

Leu Gln Phe Ser Asp Gln Ala Gly Val Ser Val Leu Tyr Thr Val Thr
            100                 105                 110

Leu Trp Val Glu Ser Trp Ala Arg Asn Gln Thr Glu Lys Ser Pro Glu
        115                 120                 125

Val Thr Leu Gln Leu Tyr Asn Ser Val Lys Tyr Glu Pro Pro Leu Gly
```

```
           130                 135                 140
Asp Ile Lys Val Ser Lys Leu Ala Gly Gln Leu Arg Met Glu Trp Glu
145                 150                 155                 160

Thr Pro Asp Asn Gln Val Gly Ala Glu Val Gln Phe Arg His Arg Thr
                165                 170                 175

Pro Ser Ser Pro Trp Lys Leu Gly Asp Cys Gly Pro Gln Asp Asp Asp
            180                 185                 190

Thr Glu Ser Cys Leu Cys Pro Leu Glu Met Asn Val Ala Gln Glu Phe
        195                 200                 205

Gln Leu Arg Arg Arg Gln Leu Gly Ser Gln Gly Ser Ser Trp Ser Lys
    210                 215                 220

Trp Ser Ser Pro Val Cys Val Pro Glu Asn Pro Pro Gln Pro Gln
225                 230                 235                 240

Val Arg Phe Ser Val Glu Gln Leu Gly Gln Asp Gly Arg Arg Leu
                245                 250                 255

Thr Leu Lys Glu Gln Pro Thr Gln Leu Glu Leu Pro Glu Gly Cys Gln
            260                 265                 270

Gly Leu Ala Pro Gly Thr Glu Val Thr Tyr Arg Leu Gln Leu His Met
        275                 280                 285

Leu Ser Cys Pro Cys Lys Ala Lys Ala Thr Arg Thr Leu His Leu Gly
    290                 295                 300

Lys Met Pro Tyr Leu Ser Gly Ala Ala Tyr Asn Val Ala Val Ile Ser
305                 310                 315                 320

Ser Asn Gln Phe Gly Pro Gly Leu Asn Gln Thr Trp His Ile Pro Ala
                325                 330                 335

Asp Thr His Thr Glu Pro Val Ala Leu Asn Ile Ser Val Gly Thr Asn
            340                 345                 350

Gly Thr Thr Met Tyr Trp Pro Ala Arg Ala Gln Ser Met Thr Tyr Cys
        355                 360                 365

Ile Glu Trp Gln Pro Val Gly Gln Asp Gly Gly Leu Ala Thr Cys Ser
    370                 375                 380

Leu Thr Ala Pro Gln Asp Pro Asp Pro Ala Gly Met Ala Thr Tyr Ser
385                 390                 395                 400

Trp Ser Arg Glu Ser Gly Ala Met Gly Gln Glu Lys Cys Tyr Tyr Ile
                405                 410                 415

Thr Ile Phe Ala Ser Ala His Pro Glu Lys Leu Thr Leu Trp Ser Thr
            420                 425                 430

Val Leu Ser Thr Tyr His Phe Gly Gly Asn Ala Ser Ala Ala Gly Thr
        435                 440                 445

Pro His His Val Ser Val Lys Asn His Ser Leu Asp Ser Val Ser Val
    450                 455                 460

Asp Trp Ala Pro Ser Leu Leu Ser Thr Cys Pro Gly Val Leu Lys Glu
465                 470                 475                 480

Tyr Val Val Arg Cys Arg Asp Glu Asp Ser Lys Gln Val Ser Glu His
                485                 490                 495

Pro Val Gln Pro Thr Glu Thr Gln Val Thr Leu Ser Gly Leu Arg Ala
            500                 505                 510

Gly Val Ala Tyr Thr Val Gln Val Arg Ala Asp Thr Ala Trp Leu Arg
        515                 520                 525

Gly Val Trp Ser Gln Pro Gln Arg Phe Ser Ile Glu Val Gln Val Ser
    530                 535                 540

Asp Trp Leu Ile Phe Phe Ala Ser Leu Gly Ser Phe Leu Ser Ile Leu
545                 550                 555                 560
```

Leu Val Gly Val Leu Gly Tyr Leu Gly Leu Asn Arg Ala Ala Arg His
                565                 570                 575

Leu Cys Pro Pro Leu Pro Thr Pro Cys Ala Ser Ser Ala Ile Glu Phe
                580                 585                 590

Pro Gly Gly Lys Glu Thr Trp Gln Trp Ile Asn Pro Val Asp Phe Gln
                595                 600                 605

Glu Glu Ala Ser Leu Gln Glu Ala Leu Val Val Glu Met Ser Trp Asp
                610                 615                 620

Lys Gly Glu Arg Thr Glu Pro Leu Glu Lys Thr Glu Leu Pro Glu Gly
625                 630                 635                 640

Ala Pro Glu Leu Ala Leu Asp Thr Glu Leu Ser Leu Glu Asp Gly Asp
                645                 650                 655

Arg Cys Lys Ala Lys Met
                660

<210> SEQ ID NO 90
<211> LENGTH: 451
<212> TYPE: PRT
<213> ORGANISM: Homo sapiens

<400> SEQUENCE: 90

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Ser Tyr
                20                  25                  30

Gly Met Ser Trp Val Arg Gln Ala Pro Gly Lys Gly Leu Glu Trp Val
            35                  40                  45

Ala Gly Ile Ser Tyr Ser Gly Ser Asp Thr Glu Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Pro Asp Tyr Ile Ile Asp Tyr Gly Phe Asp Tyr Trp Gly
                100                 105                 110

Arg Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His

```
                    260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
        290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 91
<211> LENGTH: 451
<212> TYPE: PRT
<213> ORGANISM: Homo sapiens

<400> SEQUENCE: 91

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Thr Ser Tyr
            20                  25                  30
Gly Met Ser Trp Val Arg Gln Ala Pro Gly Lys Gly Leu Glu Trp Val
        35                  40                  45
Ala Gly Ile Ser Tyr Asp Ala Ser Asp Thr Glu Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ser Pro Asp Tyr Ile Ile Asp Tyr Gly Phe Asp Tyr Trp Gly
            100                 105                 110
Arg Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
```

```
Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 92
<211> LENGTH: 451
<212> TYPE: PRT
<213> ORGANISM: Homo sapiens

<400> SEQUENCE: 92

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Met Ile Gly Pro Gln His Gly Glu Ala Ile Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95
```

Ala Arg Glu Ser Thr Asp Ser Asp Glu Ser Pro Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 93
<211> LENGTH: 451
<212> TYPE: PRT
<213> ORGANISM: Homo sapiens

<400> SEQUENCE: 93

Gln Val Gln Leu Val Gln Ser Gly Ala Glu Val Lys Lys Pro Gly Ala

-continued

```
1               5                   10                  15
Ser Val Lys Val Ser Cys Lys Ala Ser Gly Tyr Thr Phe Thr Gly Tyr
                20                  25                  30
Tyr Met His Trp Val Arg Gln Ala Pro Gly Gln Gly Leu Glu Trp Met
                35                  40                  45
Gly Met Ile Gly Pro Gln His Gly Glu Ala Ile Tyr Ala Gln Lys Phe
            50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Thr Ala Val Tyr Tyr Cys
                    85                  90                  95
Ala Arg Glu Ser Thr Asp Ser Asp Glu Ser Pro Phe Asp Tyr Trp Gly
                100                 105                 110
Gln Gly Thr Leu Val Thr Val Ser Ser Ala Ser Thr Lys Gly Pro Ser
                115                 120                 125
Val Phe Pro Leu Ala Pro Ser Ser Lys Ser Thr Ser Gly Gly Thr Ala
            130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
                195                 200                 205
Lys Pro Ser Asn Thr Lys Val Asp Lys Arg Val Glu Pro Lys Ser Cys
210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
        290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Glu Glu Met Thr Lys Asn Gln Val Ser
            355                 360                 365
Leu Thr Cys Leu Val Lys Gly Phe Tyr Pro Ser Asp Ile Ala Val Glu
        370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
```

His Glu Ala Leu His Asn His Tyr Thr Gln Lys Ser Leu Ser Leu Ser
            435                 440                 445

Pro Gly Lys
    450

<210> SEQ ID NO 94
<211> LENGTH: 1353
<212> TYPE: DNA
<213> ORGANISM: Homo sapiens

<400> SEQUENCE: 94

| | | |
|---|---|---|
| caggtgcaat tggtggaaag cggcggaggc gtggtgcagc ctggcagaag cctgagactg | 60 |
| agctgtgccg ccagcggctt caccttcacc agctacggca tgagctgggt ccgacaggcc | 120 |
| cctggcaagg gcctggaatg gtggccggc atcagctaca gcggcagcga caccgagtac | 180 |
| gccgacagcg tgaagggccg gttcaccatc agccgggaca cagcaagaa caccctgtac | 240 |
| ctgcagatga acagcctgcg ggccgaggac accgccgtgt actactgcgc cagaagcccc | 300 |
| gactacatca tcgactacgg cttcgactac tggggcagag gcaccctggt caccgtcagc | 360 |
| tcagcctcca ccaagggtcc atcggtcttc cccctggcac cctcctccaa gagcacctct | 420 |
| gggggcacag cggccctggg ctgcctggtc aaggactact ccccgaaacc ggtgacggtg | 480 |
| tcgtggaact caggcgccct gaccagcggc gtgcacacct tcccggctgt cctacagtcc | 540 |
| tcaggactct actccctcag cagcgtggtg accgtgccct ccagcagctt gggcacccag | 600 |
| acctacatct gcaacgtgaa tcacaagccc agcaacacca aggtggacaa gagagttgag | 660 |
| cccaaatctt gtgacaaaac tcacacatgc ccaccgtgcc cagcacctga actcctgggg | 720 |
| ggaccgtcag tcttcctctt ccccccaaaa cccaaggaca cccctcatgat ctccccggacc | 780 |
| cctgaggtca catgcgtggt ggtggacgtg agccacgaag accctgaggt caagttcaac | 840 |
| tggtacgtgg acggcgtgga ggtgcataat gccaagacaa agccgcggga ggagcagtac | 900 |
| aacagcacgt accgggtggt cagcgtcctc accgtcctgc accaggactg gctgaatggc | 960 |
| aaggagtaca agtgcaaggt ctccaacaaa gccctcccag cccccatcga gaaaaccatc | 1020 |
| tccaaagcca aagggcagcc ccgagaacca caggtgtaca ccctgccccc atcccgggag | 1080 |
| gagatgacca agaaccaggt cagcctgacc tgcctggtca aaggcttcta tcccagcgac | 1140 |
| atcgccgtgg agtgggagag caatgggcag ccggagaaca actacaagac cacgcctccc | 1200 |
| gtgctggact ccgacggctc cttcttcctc tacagcaagc tcaccgtgga caagagcagg | 1260 |
| tggcagcagg ggaacgtctt ctcatgctcc gtgatgcatg aggctctgca caaccactac | 1320 |
| acgcagaaga gcctctccct gtctccgggt aaa | 1353 |

<210> SEQ ID NO 95
<211> LENGTH: 1353
<212> TYPE: DNA
<213> ORGANISM: Homo sapiens

<400> SEQUENCE: 95

| | | |
|---|---|---|
| caggtgcaat tggtggaaag cggcggaggc gtggtgcagc ctggcagaag cctgagactg | 60 |
| agctgtgccg ccagcggctt caccttcacc agctacggca tgagctgggt ccgacaggcc | 120 |
| cctggcaagg gcctggaatg gtggccggc atcagctacg acgccagcga caccgagtac | 180 |
| gccgacagcg tgaagggccg gttcaccatc agccgggaca cagcaagaa caccctgtac | 240 |
| ctgcagatga acagcctgcg ggccgaggac accgccgtgt actactgcgc cagaagcccc | 300 |

| | |
|---|---|
| gactacatca tcgactacgg cttcgactac tggggcagag gcaccctggt caccgtcagc | 360 |
| tcagcctcca ccaagggtcc atcggtcttc cccctggcac cctcctccaa gagcacctct | 420 |
| gggggcacag cggccctggg ctgcctggtc aaggactact tccccgaacc ggtgacggtg | 480 |
| tcgtggaact caggcgccct gaccagcggc gtgcacacct tcccggctgt cctacagtcc | 540 |
| tcaggactct actccctcag cagcgtggtg accgtgccct ccagcagctt gggcacccag | 600 |
| acctacatct gcaacgtgaa tcacaagccc agcaacacca aggtggacaa gagagttgag | 660 |
| cccaaatctt gtgacaaaac tcacacatgc ccaccgtgcc cagcacctga actcctgggg | 720 |
| ggaccgtcag tcttcctctt ccccccaaaa cccaaggaca ccctcatgat ctcccggacc | 780 |
| cctgaggtca catgcgtggt ggtggacgtg agccacgaag accctgaggt caagttcaac | 840 |
| tggtacgtgg acggcgtgga ggtgcataat gccaagacaa agccgcggga ggagcagtac | 900 |
| aacagcacgt accgggtggt cagcgtcctc accgtcctgc accaggactg gctgaatggc | 960 |
| aaggagtaca agtgcaaggt ctccaacaaa gccctcccag cccccatcga gaaaaccatc | 1020 |
| tccaaagcca aagggcagcc ccgagaacca caggtgtaca ccctgccccc atcccgggag | 1080 |
| gagatgacca agaaccaggt cagcctgacc tgcctggtca aaggcttcta tcccagcgac | 1140 |
| atcgccgtgg agtgggagag caatgggcag ccggagaaca actacaagac cacgcctccc | 1200 |
| gtgctggact ccgacggctc cttcttcctc tacagcaagc tcaccgtgga caagagcagg | 1260 |
| tggcagcagg ggaacgtctt ctcatgctcc gtgatgcatg aggctctgca caaccactac | 1320 |
| acgcagaaga gcctctccct gtctccgggt aaa | 1353 |

<210> SEQ ID NO 96
<211> LENGTH: 1353
<212> TYPE: DNA
<213> ORGANISM: Homo sapiens

<400> SEQUENCE: 96

| | |
|---|---|
| caggtgcaat tggtgcagtc tggcgccgaa gtgaagaaac ctggggctag tgtgaaggtg | 60 |
| tcctgcaagg ccagcggcta caccttcacc ggctactaca tgcactgggt ccgacaggcc | 120 |
| cctggacagg gcctggaatg gatgggcatg atcggccccc agcacggcga ggccatctac | 180 |
| gcccagaaat tccagggcag agtgaccatg acccgggaca ccagcatcag caccgcctac | 240 |
| atggaactga gccggctgcg gagcgaggac accgccgtgt actactgcgc cagagagagc | 300 |
| accgacagcg acgagagccc cttcgactac tggggccagg gcaccctggt caccgtcagc | 360 |
| tcagcctcca ccaagggtcc atcggtcttc cccctggcac cctcctccaa gagcacctct | 420 |
| gggggcacag cggccctggg ctgcctggtc aaggactact tccccgaacc ggtgacggtg | 480 |
| tcgtggaact caggcgccct gaccagcggc gtgcacacct tcccggctgt cctacagtcc | 540 |
| tcaggactct actccctcag cagcgtggtg accgtgccct ccagcagctt gggcacccag | 600 |
| acctacatct gcaacgtgaa tcacaagccc agcaacacca aggtggacaa gagagttgag | 660 |
| cccaaatctt gtgacaaaac tcacacatgc ccaccgtgcc cagcacctga actcctgggg | 720 |
| ggaccgtcag tcttcctctt ccccccaaaa cccaaggaca ccctcatgat ctcccggacc | 780 |
| cctgaggtca catgcgtggt ggtggacgtg agccacgaag accctgaggt caagttcaac | 840 |
| tggtacgtgg acggcgtgga ggtgcataat gccaagacaa agccgcggga ggagcagtac | 900 |
| aacagcacgt accgggtggt cagcgtcctc accgtcctgc accaggactg gctgaatggc | 960 |
| aaggagtaca agtgcaaggt ctccaacaaa gccctcccag cccccatcga gaaaaccatc | 1020 |
| tccaaagcca aagggcagcc ccgagaacca caggtgtaca ccctgccccc atcccgggag | 1080 |

```
gagatgacca agaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tacagcaagc tcaccgtgga caagagcagg   1260
tggcagcagg ggaacgtctt ctcatgctcc gtgatgcatg aggctctgca caaccactac   1320
acgcagaaga gcctctccct gtctccgggt aaa                                1353
```

<210> SEQ ID NO 97
<211> LENGTH: 1353
<212> TYPE: DNA
<213> ORGANISM: Homo sapiens

<400> SEQUENCE: 97

```
caggtgcaat tggtgcagtc tggcgccgaa gtgaagaaac tggggccag cgtgaaggtg     60 tcctgcaagg ccagcggcta caccttcacc ggctactaca tgcactgggt ccgacaggcc   120
cctggacagg gcctggaatg gatgggcatg atcggccccc agcacggcga ggccatctac   180
gcccagaaat tccagggcag agtgaccatg accgggaca ccagcatcag caccgcctac    240
atggaactga gccggctgcg gagcgacgac ccgccgtgt actactgcgc cagagagagc    300
accgacagcg acgagagccc cttcgactac tgggggcagg gcaccctggt caccgtcagc   360
tcagcctcca ccaagggtcc atcggtcttc cccctggcac cctcctccaa gagcacctct   420
gggggcacag cggccctggg ctgcctggtc aaggactact ccccgaacc ggtgacggtg    480 tcgtggaact caggcgccct gaccagcggc gtgcacacct tcccggctgt cctacagtcc   540
tcaggactct actccctcag cagcgtggtg accgtgccct ccagcagctt gggcacccag   600
acctacatct gcaacgtgaa tcacaagccc agcaacacca aggtggacaa gagagttgag   660
cccaaatctt gtgacaaaac tcacacatgc ccaccgtgcc cagcacctga actcctgggg   720
ggaccgtcag tcttcctctt ccccccaaaa cccaaggaca cctcatgat ctcccggacc    780 cctgaggtca catgcgtggt ggtggacgtg agccacgaag accctgaggt caagttcaac   840
tggtacgtgg acggcgtgga ggtgcataat gccaagacaa agccgcggga ggagcagtac   900
aacagcacgt accgggtggt cagcgtcctc accgtcctgc accaggactg gctgaatggc   960
aaggagtaca agtgcaaggt ctccaacaaa gccctcccag cccccatcga gaaaaccatc  1020
tccaaagcca aagggcagcc ccgagaacca caggtgtaca ccctgccccc atccgggag   1080 gagatgacca agaaccaggt cagcctgacc tgcctggtca aaggcttcta tcccagcgac  1140
atcgccgtgg agtgggagag caatgggcag ccggagaaca actacaagac cacgcctccc  1200
gtgctggact ccgacggctc cttcttcctc tacagcaagc tcaccgtgga caagagcagg  1260
tggcagcagg ggaacgtctt ctcatgctcc gtgatgcatg aggctctgca caaccactac  1320
acgcagaaga gcctctccct gtctccgggt aaa                               1353
```

<210> SEQ ID NO 98
<211> LENGTH: 662
<212> TYPE: PRT
<213> ORGANISM: Homo sapiens

<400> SEQUENCE: 98

```
Met Glu Pro Leu Val Thr Trp Val Val Pro Leu Leu Leu Leu Phe Leu
1               5                   10                  15

Arg Ser Arg Gln Gly Ala Ala Cys Gly Thr Ser Glu Cys Cys Phe Gln
            20                  25                  30
```

```
Asp Pro Pro Tyr Ser Asp Ala Asp Ser Gly Ser Ala Ser Gly Pro Arg
         35                  40                  45

Asp Leu Ser Cys Tyr Arg Ile Ser Ser Ala Gly Tyr Glu Cys Ser Trp
 50                  55                  60

Gln Tyr Glu Gly Pro Thr Ala Gly Val Ser His Phe Leu Arg Cys Cys
 65                  70                  75                  80

Leu Ser Ser Gly Arg Cys Cys Tyr Phe Ala Thr Gly Ser Ala Thr Arg
                 85                  90                  95

Leu Gln Phe Ser Asp Gln Ala Gly Val Ser Val Leu His Thr Val Thr
            100                 105                 110

Leu Trp Val Glu Ser Trp Ala Arg Asn Arg Thr Glu Lys Ser Pro Glu
        115                 120                 125

Val Thr Leu Gln Leu Tyr Lys Ser Val Lys Tyr Lys Pro Pro Leu Gly
    130                 135                 140

Asp Ile Lys Val Ser Lys Leu Ala Gly Gln Leu Arg Met Glu Trp Glu
145                 150                 155                 160

Thr Pro Asp Asn Gln Val Gly Ala Glu Val Gln Phe Arg His Arg Thr
                165                 170                 175

Pro Ser Ser Ser Trp Lys Leu Gly Asp Cys Gly Pro Gln Asp Asp Asp
            180                 185                 190

Thr Glu Ser Cys Leu Cys Pro Leu Glu Met Asn Val Ala Gln Glu Phe
        195                 200                 205

Gln Leu Arg Arg Arg Arg Leu Gly Ser Gln Gly Ser Ser Trp Ser Lys
    210                 215                 220

Trp Ser Pro Val Cys Val Pro Glu Asn Pro Pro Gln Pro Gln
225                 230                 235                 240

Val Arg Phe Ser Val Glu Gln Leu Gly Arg Asp Gly Arg Arg Arg Leu
                245                 250                 255

Thr Leu Lys Glu Gln Pro Thr Gln Leu Glu Leu Pro Glu Gly Cys Gln
            260                 265                 270

Gly Pro Ala Pro Gly Val Glu Val Thr Tyr Gln Leu Gln Leu His Met
        275                 280                 285

Leu Ser Cys Pro Cys Lys Ala Lys Ala Thr Arg Thr Leu Pro Leu Glu
    290                 295                 300

Lys Met Pro Tyr Leu Ser Gly Ala Ala Tyr Asn Val Ala Val Ile Ser
305                 310                 315                 320

Ser Asn Arg Phe Gly Pro Gly Pro Asn Gln Thr Trp His Ile Pro Ala
                325                 330                 335

Asp Thr His Thr Glu Pro Val Ala Leu Asn Ile Ser Val Gly Thr Asn
            340                 345                 350

Gly Thr Thr Met Tyr Trp Pro Ala Arg Ala Gln Ser Thr Thr Tyr Cys
        355                 360                 365

Ile Glu Trp Gln Pro Val Gly Gln Glu Gly Ser Leu Ala Thr Cys Asn
    370                 375                 380

Leu Thr Ala Pro Gln Asp Pro Asp Pro Ala Gly Met Ala Thr Tyr Ser
385                 390                 395                 400

Trp Ser Arg Glu Ser Gly Ala Met Gly Gln Glu Lys Cys Tyr His Ile
                405                 410                 415

Thr Ile Phe Ala Ser Ala His Pro Lys Lys Leu Thr Leu Trp Ser Thr
            420                 425                 430

Val Leu Ser Thr Tyr His Phe Gly Gly Asn Ala Ser Ala Ala Gly Thr
        435                 440                 445

Pro His His Val Ser Val Lys Asn His Ser Leu Asp Ser Val Ser Val
```

```
            450                 455                 460
Asp Trp Ala Pro Ser Leu Leu Ser Thr Cys Pro Gly Val Leu Lys Glu
465                 470                 475                 480

Tyr Val Val Arg Cys Arg Asp Glu Asp Ser Asn Gln Val Ser Glu His
                485                 490                 495

Pro Val Gln Pro Thr Glu Thr Gln Val Thr Leu Ser Asp Leu Arg Ala
            500                 505                 510

Gly Val Ala Tyr Thr Val Gln Val Arg Ala Asp Thr Ala Trp Leu Arg
            515                 520                 525

Gly Ala Trp Ser Gln Pro Gln Arg Phe Ser Ile Lys Val Gln Val Ser
            530                 535                 540

Asp Trp Phe Ile Phe Phe Ala Ser Leu Gly Ser Phe Leu Ser Ile Leu
545                 550                 555                 560

Leu Val Gly Val Leu Gly Tyr Leu Gly Leu Asn Arg Ala Thr Arg His
                565                 570                 575

Leu Cys Pro Pro Leu Pro Thr Pro Cys Ala Ser Ser Ala Ile Gln Phe
            580                 585                 590

Pro Ala Gly Lys Glu Thr Trp Gln Trp Ile Asn Pro Val Asp Phe Gln
            595                 600                 605

Glu Glu Ala Ser Leu Gln Glu Ala Leu Val Val Glu Met Ser Trp Asp
            610                 615                 620

Lys Gly Glu Arg Thr Glu Leu Leu Glu Lys Ala Glu Leu Pro Glu Gly
625                 630                 635                 640

Ala Pro Glu Leu Ala Leu Asp Thr Gln Leu Ser Leu Glu Asp Gly Asp
                645                 650                 655

Arg Cys Lys Ala Lys Met
                660

<210> SEQ ID NO 99
<211> LENGTH: 328
<212> TYPE: PRT
<213> ORGANISM: Homo sapiens

<400> SEQUENCE: 99

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
            35                  40                  45

Thr Cys Asp Thr Pro Glu Glu Asp Gly Ile Thr Trp Thr Leu Asp Gln
        50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
        130                 135                 140

Leu Thr Thr Ile Ser Thr Asp Leu Thr Phe Ser Val Lys Ser Ser Arg
145                 150                 155                 160
```

-continued

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 100
<211> LENGTH: 253
<212> TYPE: PRT
<213> ORGANISM: Homo sapiens

<400> SEQUENCE: 100

Met Trp Pro Pro Gly Ser Ala Ser Gln Pro Pro Pro Ser Pro Ala Ala
1               5                   10                  15

Ala Thr Gly Leu His Pro Ala Ala Arg Pro Val Ser Leu Gln Cys Arg
            20                  25                  30

Leu Ser Met Cys Pro Ala Arg Ser Leu Leu Leu Val Ala Thr Leu Val
        35                  40                  45

Leu Leu Asp His Leu Ser Leu Ala Arg Asn Leu Pro Val Ala Thr Pro
    50                  55                  60

Asp Pro Gly Met Phe Pro Cys Leu His His Ser Gln Asn Leu Leu Arg
65                  70                  75                  80

Ala Val Ser Asn Met Leu Gln Lys Ala Arg Gln Thr Leu Glu Phe Tyr
                85                  90                  95

Pro Cys Thr Ser Glu Glu Ile Asp His Glu Asp Ile Thr Lys Asp Lys
            100                 105                 110

Thr Ser Thr Val Glu Ala Cys Leu Pro Leu Glu Leu Thr Lys Asn Glu
        115                 120                 125

Ser Cys Leu Asn Ser Arg Glu Thr Ser Phe Ile Thr Asn Gly Ser Cys
    130                 135                 140

Leu Ala Ser Arg Lys Thr Ser Phe Met Met Ala Leu Cys Leu Ser Ser
145                 150                 155                 160

Ile Tyr Glu Asp Leu Lys Met Tyr Gln Val Glu Phe Lys Thr Met Asn
                165                 170                 175

Ala Lys Leu Leu Met Asp Pro Lys Arg Gln Ile Phe Leu Asp Gln Asn
            180                 185                 190

Met Leu Ala Val Ile Asp Glu Leu Met Gln Ala Leu Asn Phe Asn Ser
        195                 200                 205

```
Glu Thr Val Pro Gln Lys Ser Ser Leu Glu Glu Pro Asp Phe Tyr Lys
        210                 215                 220

Thr Lys Ile Lys Leu Cys Ile Leu Leu His Ala Phe Arg Ile Arg Ala
225                 230                 235                 240

Val Thr Ile Asp Arg Val Met Ser Tyr Leu Asn Ala Ser
                    245                 250

<210> SEQ ID NO 101
<211> LENGTH: 189
<212> TYPE: PRT
<213> ORGANISM: Homo sapiens

<400> SEQUENCE: 101

Met Leu Gly Ser Arg Ala Val Met Leu Leu Leu Leu Pro Trp Thr
1                5                   10                  15

Ala Gln Gly Arg Ala Val Pro Gly Gly Ser Ser Pro Ala Trp Thr Gln
                20                  25                  30

Cys Gln Gln Leu Ser Gln Lys Leu Cys Thr Leu Ala Trp Ser Ala His
                35                  40                  45

Pro Leu Val Gly His Met Asp Leu Arg Glu Glu Gly Asp Glu Glu Thr
            50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
                100                 105                 110

Pro Ser Leu Leu Pro Asp Ser Pro Val Gly Gln Leu His Ala Ser Leu
                115                 120                 125

Leu Gly Leu Ser Gln Leu Leu Gln Pro Glu Gly His His Trp Glu Thr
            130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
                180                 185
```